(12) United States Patent
Luo et al.

(10) Patent No.: US 11,406,714 B2
(45) Date of Patent: Aug. 9, 2022

(54) TELODENDRIMERS AND NANOCARRIERS AND METHODS OF USING SAME

(71) Applicant: The Research Foundation for the State University of New York, Syracuse, NY (US)

(72) Inventors: Juntao Luo, Jamesville, NY (US); Wenzhe Huang, Fayetteville, NY (US); Yu Shao, Syracuse, NY (US); Changying Shi, Jamesville, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 169 days.

(21) Appl. No.: 13/972,539

(22) Filed: Aug. 21, 2013

(65) Prior Publication Data
US 2015/0056139 A1 Feb. 26, 2015

(51) Int. Cl.
| A61K 47/34 | (2017.01) |
| A61K 49/00 | (2006.01) |
| A61K 9/51  | (2006.01) |
| A61K 47/55 | (2017.01) |
| A61K 47/54 | (2017.01) |

(52) U.S. Cl.
CPC ............ *A61K 47/34* (2013.01); *A61K 9/5146* (2013.01); *A61K 47/551* (2017.08); *A61K 47/554* (2017.08); *A61K 49/0054* (2013.01)

(58) Field of Classification Search
None
See application file for complete search history.

(56) References Cited

U.S. PATENT DOCUMENTS

| 8,529,681 B1* | 9/2013 | Hibbs ................. C08F 2/48 |
| | | 106/15.05 |
| 2008/0299220 A1 | 12/2008 | Tamarkin et al. |
| 2008/0312581 A1 | 12/2008 | Hardy |
| 2011/0286915 A1* | 11/2011 | Lam ..................... A61K 9/1075 |
| | | 424/1.29 |
| 2013/0164369 A1 | 6/2013 | Lam et al. |

FOREIGN PATENT DOCUMENTS

| WO | 2010039496 A2 | 4/2010 |
| WO | 2012158622 | 11/2012 |
| WO | 2013096388 | 6/2013 |

OTHER PUBLICATIONS

Gu et al. (Biomacromolecules, 9, 255-262, 2008, published on the web on Dec. 21, 2007).*
Jeong et al. (Journal of Controlled Release, 101, 49-68, 2005).*
Tomic-Vatic et al. (Int. J. Cancer, 117, 188-193, 2005, Vitamin E, amides.*
Yuanpei et al., Well-Defined, Reversible Boronate Crosslinked Nanocarriers for Targeted Drug Delivery in Response to Acidic pH-14; Values and cis-Diols, Angewandte Chemie International Edition, vol. 51, No. 12, pp. 2864-2869. Jan. 17, 2012.
Luo et al., Well-Defined, Size-Tunable, Multifunctional Micelles for Efficient Paclitaxel Delivery for Cancer Treatment, Bioconjugate Chemistry, vol. 21, No. 7, pp. 1216-1224. Jul. 21, 2010.
Xiao et al., A self-assembling nanoparticle for paclitaxel delivery in ovarian cancer, Biomaterials, vol. 30, No. 30, pp. 6006-6016. Oct. 1, 2009.
Yuanpei et al., Well-defined, reversible disulfide cross-linked micelles for on-demand paclitaxel delivery, Biomaterials, vol. 32, No. 27, pp. 6633-6645. May 16, 2011.

* cited by examiner

*Primary Examiner* — Tigabu Kassa
(74) *Attorney, Agent, or Firm* — Michael Krenicky; Lance Reich; Steven A. Wood, Jr.

(57) ABSTRACT

Provided are functional segregated telodendrimers having, for example, two or three functional segments. The telodendrimers can have one or more crosslinking groups (e.g., reversible photocrosslinking groups). The telodendrimers can aggregate to form nanocarriers. Cargo such as drugs, imaging probes, and other materials may be sequestered in the core of the aggregates via non-covalent or covalent interactions with the telodendrimers. Such nanocarriers may be used in drug delivery applications and imaging applications.

26 Claims, 57 Drawing Sheets

Telodendrimers with functionally segregated structures for efficient drug delivery

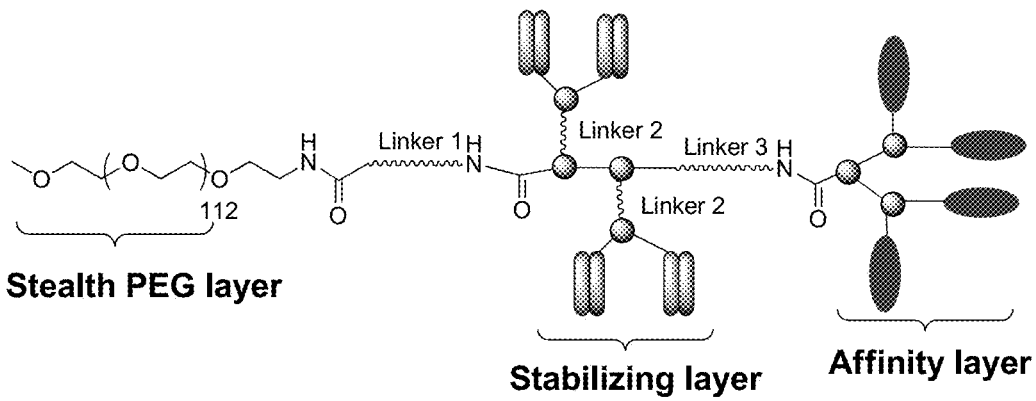

PEG layer: forms hydrophilic shell to stablize nanoparticle and avoid RES clearance *in vivo*;
Stabilizing layer: shelters the drug holding layer and further stabilizes nanoparticle;
Affinity layer: optimizes the drug loading capacity and stability.

- ⬤ Branching reagents: such as Lysine, ornithine, dihydroxyl carboxylic acid, etc.
- ▬ Stabilizing layer: facial amphiphilic building blocks (e.g. bile acids, cholic acid and its derivatives, riboflavin, etc) or photo-crosslinkable building blocks (e.g. coumarine and derivatives; cinnmic acid and derivatives, etc)
- ▬ Affinity layer: Drug like building blocks, such as cholic acid, vitamin e, coumarin, curcurmine, rhein, flavin and isoflavin derivatives, anthraquinone derivatives and xanthenone derivatives, etc
- ∿ Linker 1, 2, 3: can be amino acids, e.g alanine, glycine, or PEG linkers, or reducing labile disulfide bond linker or acidic labile linkers

Figure 1

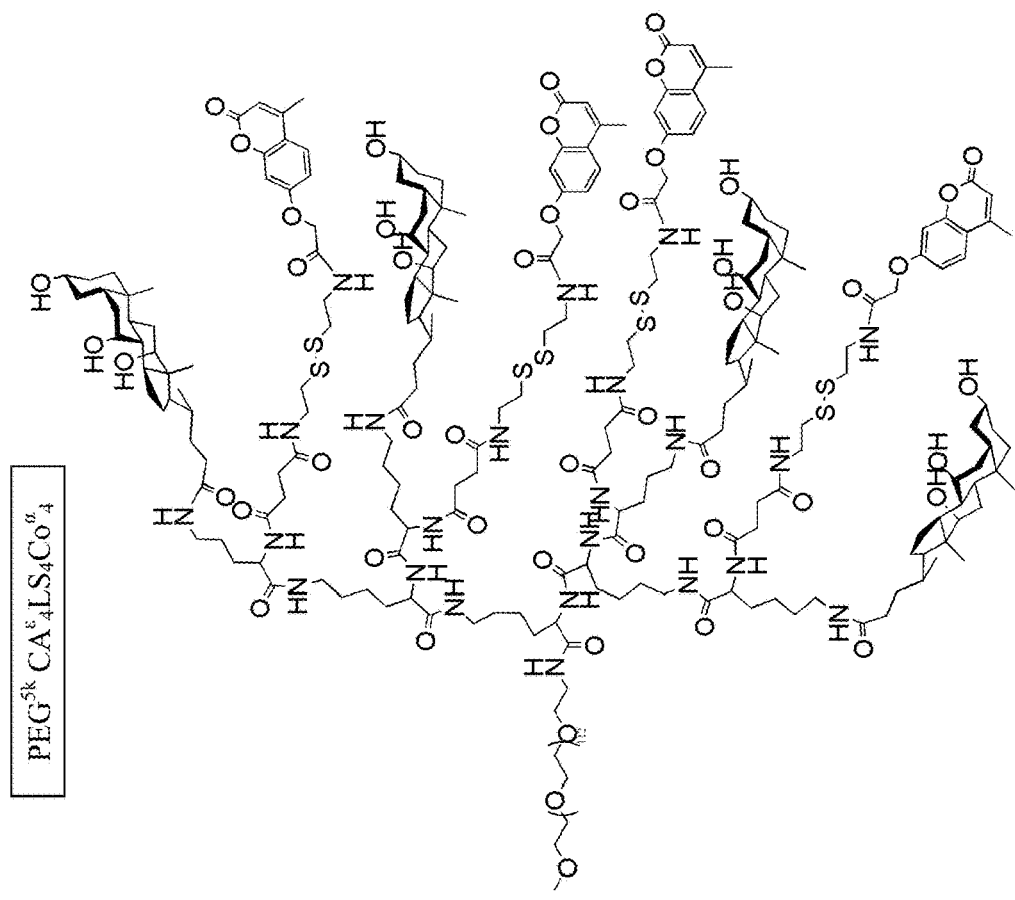
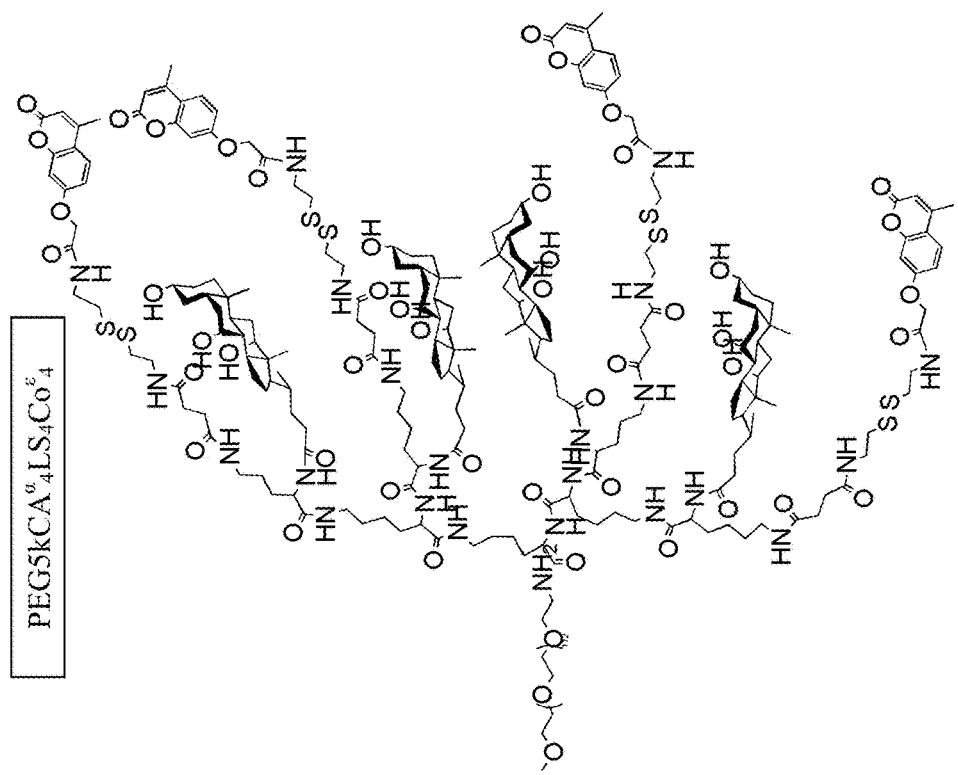
Figure 27

TELODENDRIMERS AND NANOCARRIERS AND METHODS OF USING SAME

STATEMENT REGARDING FEDERALLY SPONSORED RESEARCH

This disclosure was made with government support under contract no. 1097023-58449 awarded by the National Institutes of Health and National Cancer Institute. The government has certain rights in the disclosure.

FIELD OF THE DISCLOSURE

This disclosure generally relates to telodendrimers, and methods of making and using telodendrimers. More particularly, the disclosure relates to functional segregated telodendrimers.

BACKGROUND OF THE DISCLOSURE

Targeted drug delivery results in significant clinical benefits for disease treatment, especially for cancer. Encapsulation of cytotoxic anticancer drugs inside a nanoparticle is able to decrease side toxicity and improve the life quality of patient. In addition, passive or active targeting effect of the nanocarrier is able to deliver significantly high dose of chemodrugs to tumors and yields improved cancer treatment or even cure of the disease. Stability, drug loading capacity, reproducibility and biocompatibility are critical for the clinical translation of all drug delivery systems.

BRIEF SUMMARY OF THE DISCLOSURE

In an aspect the present disclosure provides telodendrimers that are functional segregated telodendrimers having, for example, two or three functional segments. The telodendrimers can have one or more crosslinking groups (e.g., reversible photocrosslinking groups).

In an aspect the telodendrimers are functional segregated telodendrimers having three functional segments. In an embodiment the disclosure provides a compound of formula (I):

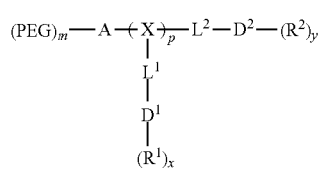

where PEG is optionally present and is a polyethylene glycol moiety, wherein PEG has a molecular weight of 44 Da to 100 kDa; A is a monomer or oligomer; X is a branched monomer unit; each $L^1$ is independently optional and is a linker group; each $L^2$ is independently optional and is a linker group; $D^1$ is optional and is a dendritic polymer moiety having one or more branched monomer units (X), a plurality of end groups, and optionally, one or more linker groups $L^1$; $D^2$ is a dendritic polymer having one or more branched monomer units (X), a plurality of end groups, and optionally, one or more linker groups ($L^3$); each $L^3$ is independently optional or a linker group linked to the focal point group of the dendritic polymer and monomer unit (X); $R^1$ and $R^2$ are the end groups of the dendritic polymer and are independently at each occurrence in the compound selected from the group consisting of a hydrophobic group, a hydrophilic group, an amphiphilic group, a reversible photocrosslinking group, and a drug; subscript x is an integer from 1 to 64, wherein subscript x is equal to the number of end groups on the dendritic polymer; subscript y is an integer from 2 to 64, wherein subscript y is equal to the number of end groups on the dendritic polymer; subscript p is an integer from 1 to 32; and subscript m is an integer from 0 to 32.

In an aspect, the disclosure provides telodendrimers having two functional moieties and one or more cross-linkable groups. For example, the cross-linkable groups are photocrosslinkable groups. In an embodiment, the telodendrimer is a compound of formula (II):

$$(PEG)_m\text{-A-L-D-}(R^3)_n \qquad (II)$$

where D is a dendritic polymer having a single focal point group, a plurality of branched monomer units X, at least one cleavable linking group, and a plurality of end groups; L is optional or a linker group linked to the focal point group of the dendritic polymer; PEG is optionally present or a polyethylene glycol, wherein PEG has a molecular weight of 44 Da to 100 kDa, including all integer kDa values and ranges therebetween; A is a monomer or oligomer linked to the PEG group; each $R^3$ are the end groups of the dendritic polymer and are independently at each occurrence in the compound selected from the group consisting of a hydrophobic group, a hydrophilic groups, an amphiphilic group, a reversible photocrosslinking group, and a drug such that at least half the number of $R^3$ groups are a reversible photocrosslinking group; subscript n is an integer from 2 to 32, including all integer values and ranges therebetween, wherein subscript n is equal to the number of end groups on the dendritic polymer, and wherein at least half the number n of $R^3$ groups are each independently selected from the group consisting of a hydrophobic group, a hydrophilic group, an amphiphilic group, reversible photocrosslinking group and a drug; and subscript m is an integer from 0 to 32, including all integer values and ranges therebetween.

In an aspect, the disclosure provides telodendrimers having 2 functional moieties and where half but not all of the end groups of the dendritic polymer are cholic acid, riboflavin, or a combination thereof. In an embodiment, the telodendrimer is a compound of formula (III):

$$(PEG)_m\text{-A-L-D-}(R^3)_n \qquad (III)$$

where D is a dendritic polymer having a single focal point group, a plurality of branched monomer units (X) and a plurality of end groups; L is optional or a linker group linked to the focal point group of the dendritic polymer; PEG is optional or a polyethylene glycol, wherein PEG has a molecular weight of 44 Da to 100 kDa, including all integer kDa values and ranges therebetween; A is a monomer or oligomer linked to the PEG group; each $R^3$ are the end groups of the dendritic polymer and are independently at each occurrence in the compound selected from the group consisting of a cholic acid moiety or derivative or analog thereof, a coumarin moiety or derivative or analog thereof, a Vitamin E moiety or derivative or analog thereof, a riboflavin moiety or derivative or analog thereof, such that at least half but not all of the number of $R^3$ groups is a cholic acid moiety or riboflavin moiety; subscript n is an integer from 2 to 64, including all integer values and ranges therebetween, wherein subscript n is equal to the number of end groups on the dendritic polymer, and wherein at least half the number n of $R^3$ groups are each independently selected from the group consisting of a cholic acid moiety or derivative or analog thereof, a coumarin moiety or derivative or analog thereof, a Vitamin E moiety or derivative or analog thereof, and a riboflavin moiety or derivative or analog thereof; and subscript m is an integer from 0 to 32, including all integer values and ranges therebetween.

In an aspect, the present disclosure provides telodendrimers where the end groups of the dendritic polymer is selected from a coumarin moiety or derivative or analog thereof, curcurmine moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, Vitamin E moiety or derivative or analog thereof, and D-α-tocopherol succinate moiety or derivative or analog thereof, Vitamins, lipids, fatty acids, Bile acids, naturally-isolated compound moieties, and drugs. In an embodiment, the telodendrimer is a compound of formula (IV):

$(PEG)_m\text{-A-L-D-}(R^3)_n$           (IV)

where D is a dendritic polymer having a single focal point group, a plurality of branched monomer units (X), at least one cleavable linking group, and a plurality of end groups; L is optional or a linker group linked to the focal point group of the dendritic polymer; PEG is optionally present or a polyethylene glycol, wherein PEG has a molecular weight of 44 Da to 100 kDa, including all integer kDa values and ranges therebetween; A is a monomer or oligomer linked to the PEG group; each $R^3$ are the end groups of the dendritic polymer and are independently at each occurrence in the compound selected from the group consisting of coumarin moiety or derivative or analog thereof, curcurmine moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, Vitamin E moiety or derivative or analog thereof, and D-α-tocopherol succinate moiety or derivative or analog thereof, Vitamins, lipids, fatty acids, Bile acids, naturally-isolated compound moieties, and drugs; subscript n is an integer from 2 to 64, including all integer values and ranges therebetween, wherein subscript n is equal to the number of end groups on the dendritic polymer, and wherein at least half the number n of $R^3$ groups are each independently selected from the group consisting of coumarin moiety or derivative or analog thereof, curcurmine moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, Vitamin E moiety or derivative or analog thereof, and D-α-tocopherol succinate moiety or derivative or analog thereof, vitamins, lipids, fatty acids, bile acids, naturally-isolated compound moieties, and drugs; and subscript m is an integer from 0 to 32, including all integer values and ranges therebetween.

In an aspect the present disclosure provides nanocarriers comprising the telodendrimers. In an embodiment, a composition comprises an aggregate of a plurality of the telodendrimers that form a nanocarrier having a hydrophobic core and a hydrophilic exterior.

In an aspect, the present disclosure provides methods of using the telodendrimers. In an embodiment, compositions comprising the telodendrimers are used in a method for treating a disease. In another embodiment, compositions comprising the telodendrimers are used in imaging methods.

DESCRIPTION OF THE DRAWINGS

FIG. 1. An example of a telodendrimer of the present disclosure.

DETAILED DESCRIPTION OF THE DISCLOSURE

Definitions

Figure 2:
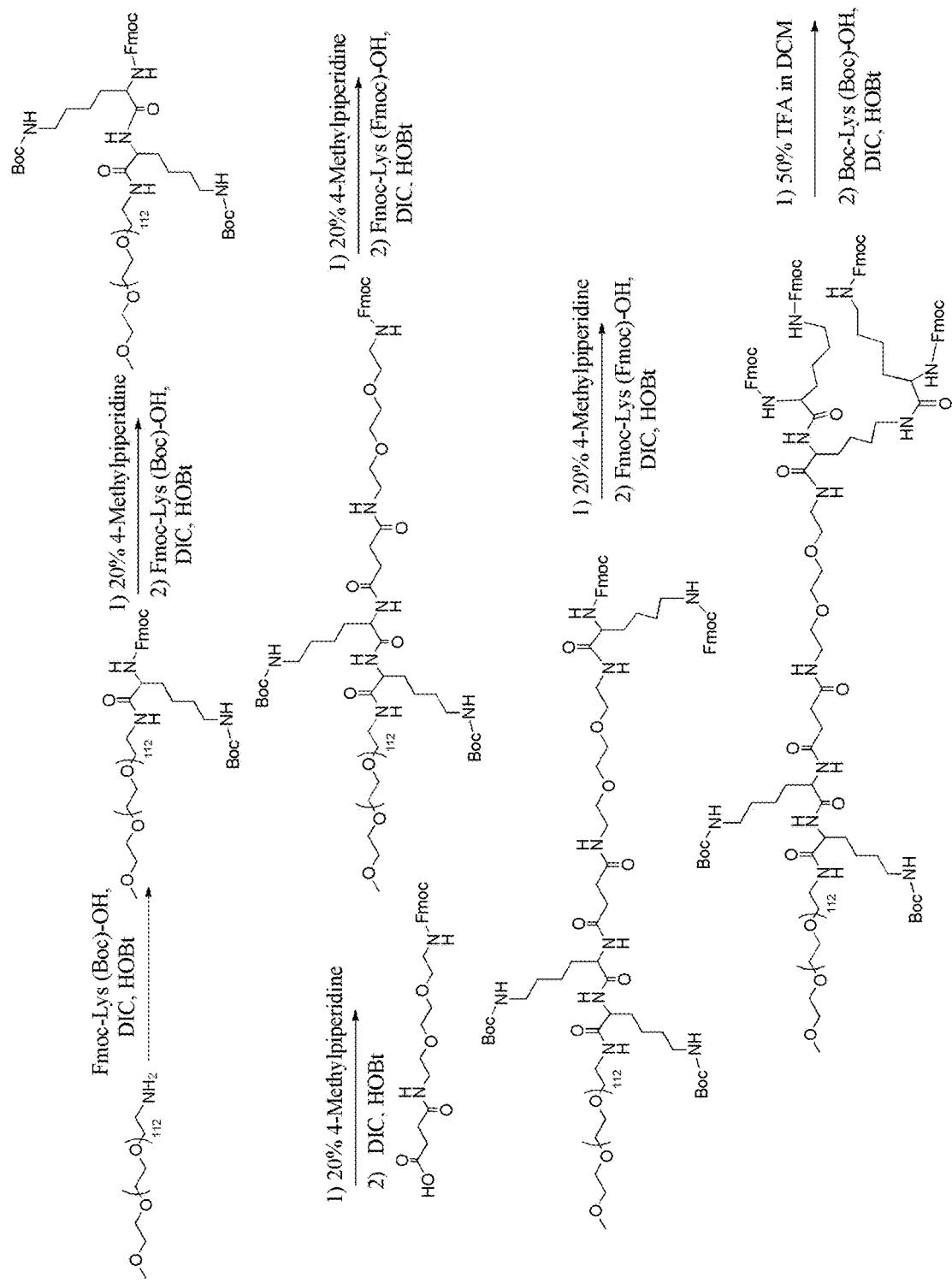
FIG. 2. An example of a synthetic route for trilayered telodendrimers with one PEG linker containing D-α-tocopherol succinate and rhein as peripheral groups, respectively, e.g., $PEG^{5k}\text{-}CA_4\text{-L-}VE_4$ and $PEG^{5k}\text{-}CA_4\text{-L-}VE_4$.
Figure 2:
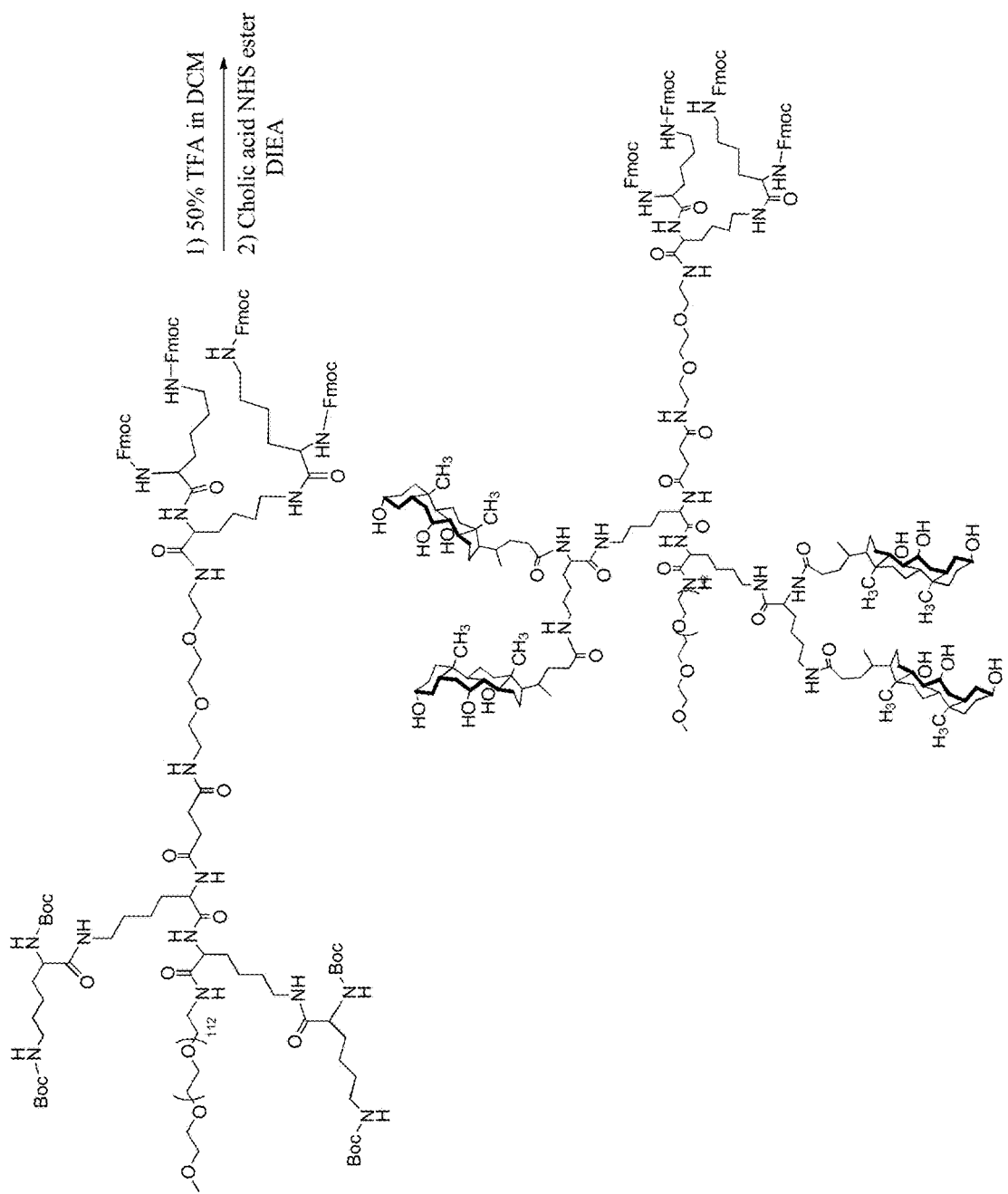
Figure 2:
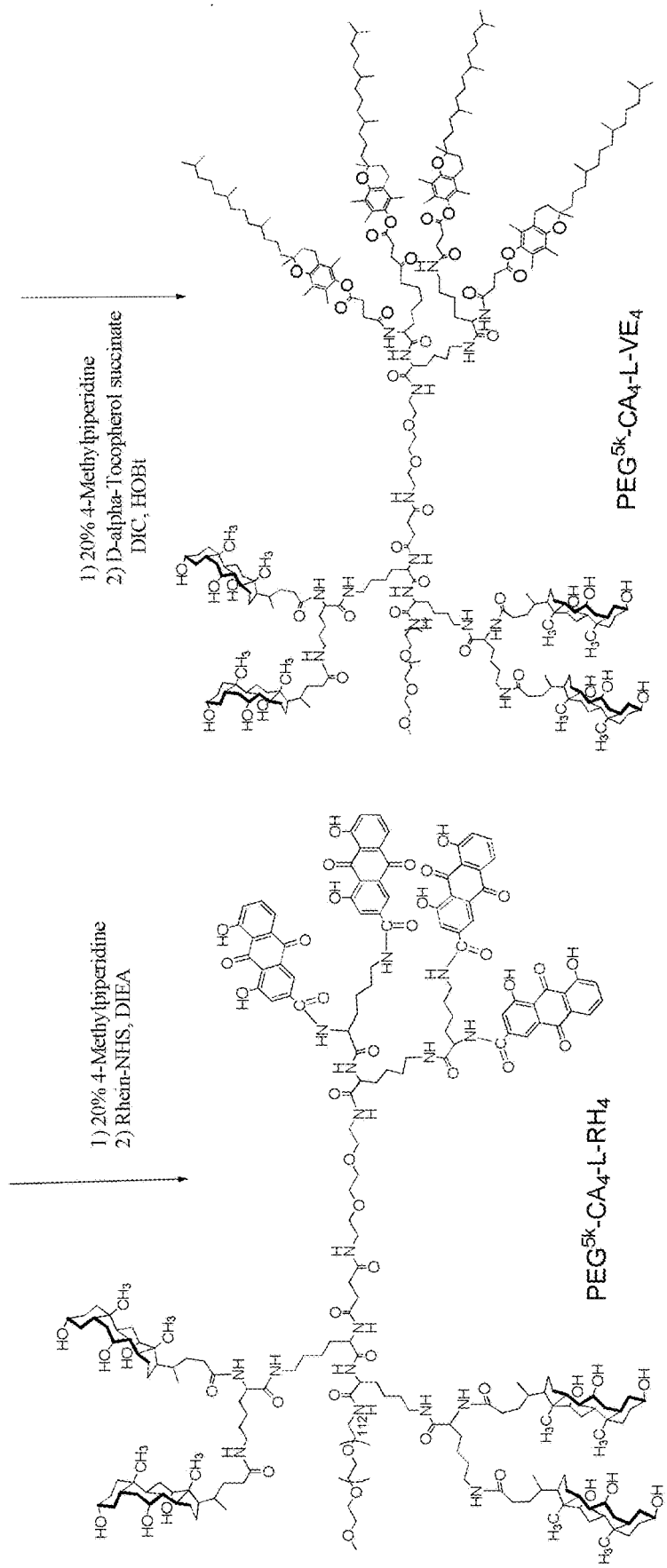
Figure 3:
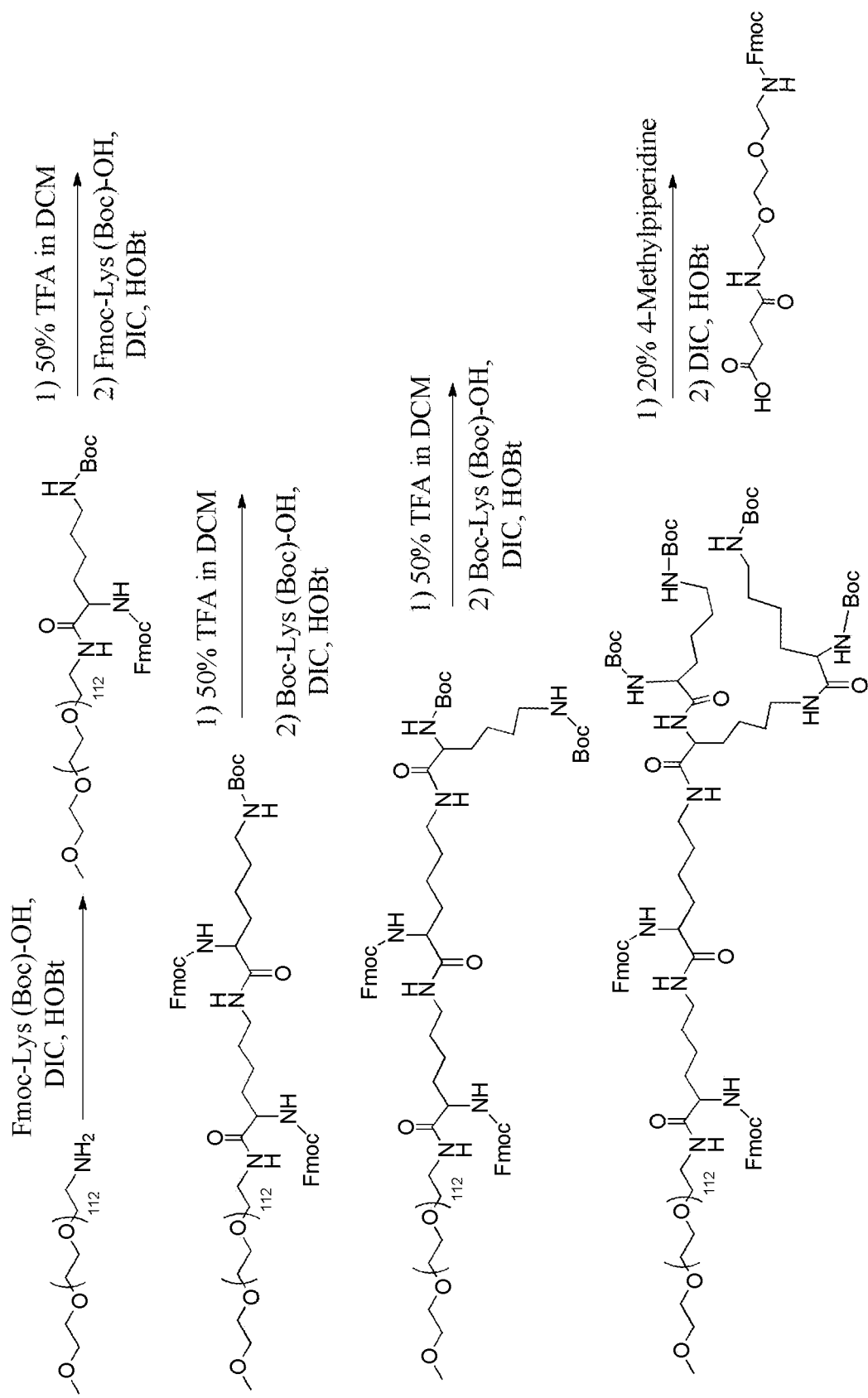
FIG. 3. An example of a synthetic route for trilayered telodendrimers with two PEG linkers containing D-α-tocopherol succinate, e.g., $PEG^{5k}\text{-}CA_4\text{-L2-}VE_4$.
Figure 3:
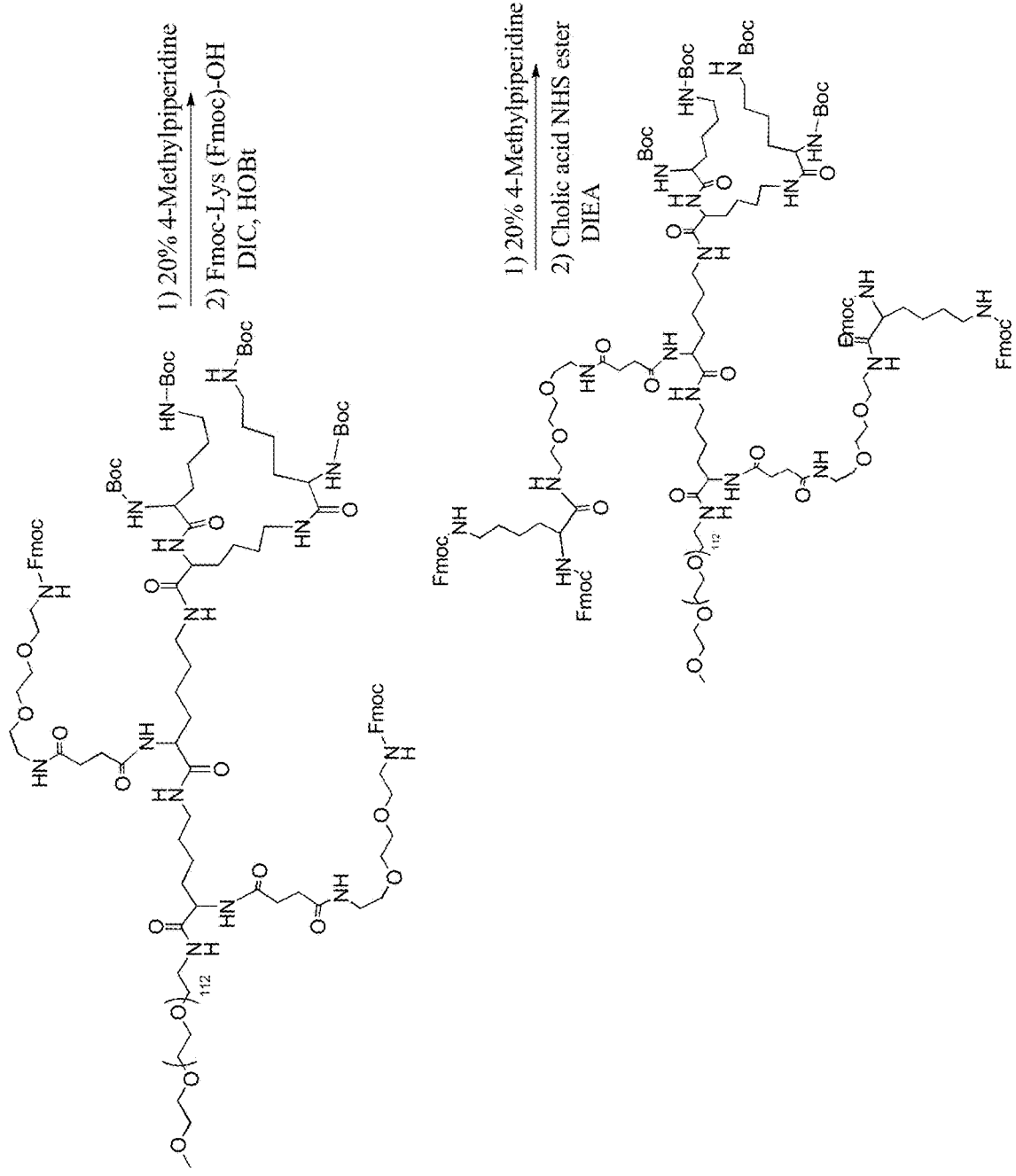
Figure 3:
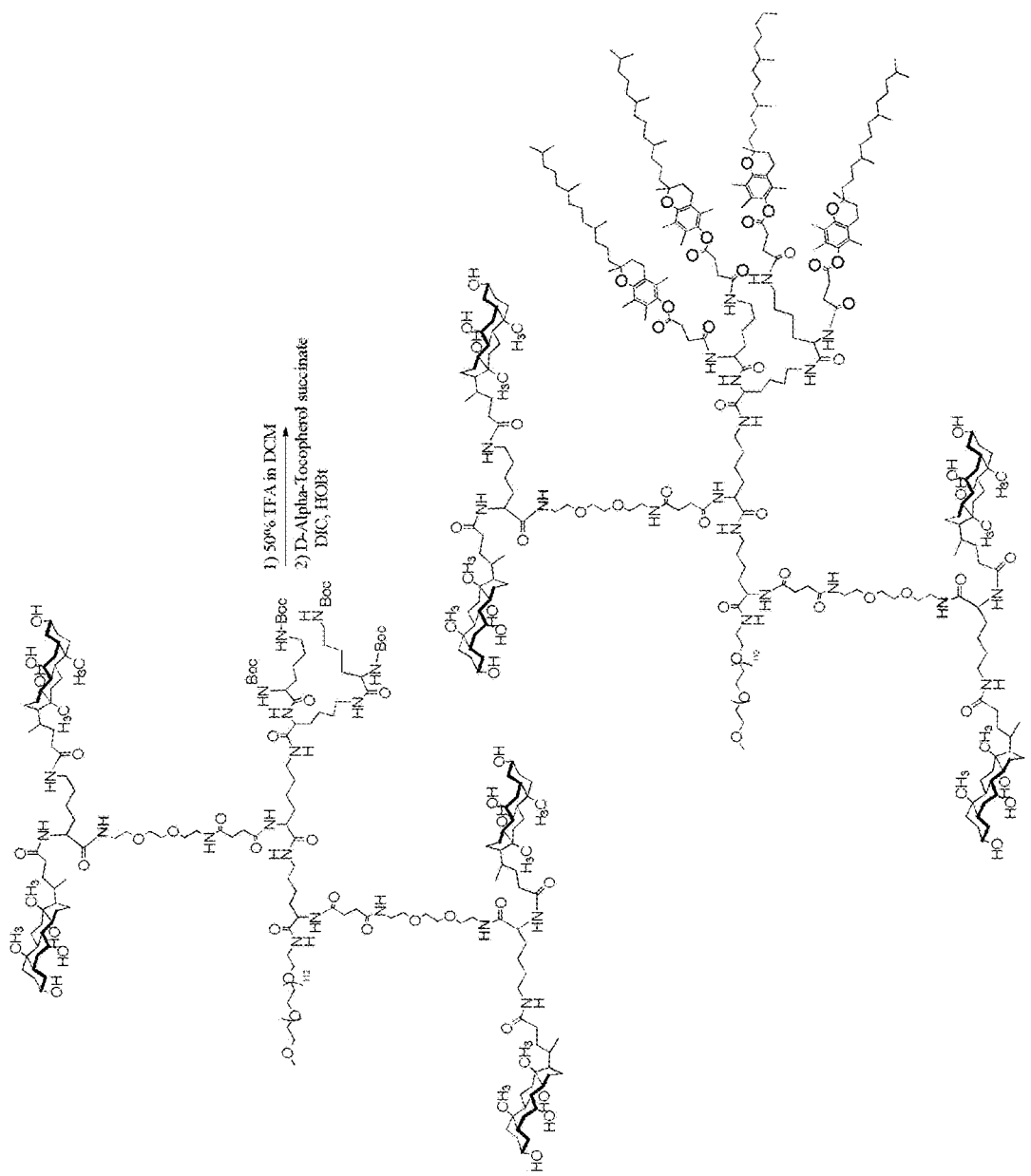

As used herein, the term "telodendrimer" refers to a linear-dendritic copolymer, containing an optional hydrophilic segment (i.e., PEG moiety) and one or more chemical moieties covalently bonded to one or more end groups of the dendron. Suitable moieties include, but are not limited to, hydrophobic groups, hydrophilic groups, amphiphilic compounds, and drugs. Different moieties may be selectively installed at selected end groups using orthogonal protecting group strategies.

As used herein, the term "moiety" refers to a part (substructure) or functional group of a molecule that is part of the telodendrimer structure. For example,

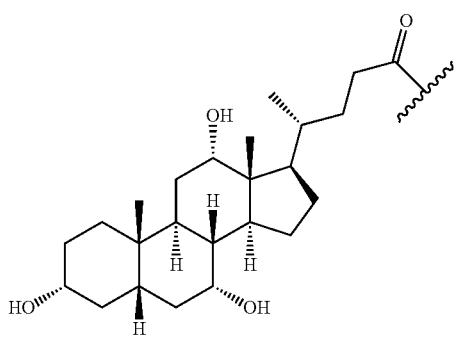

refers to a cholic acid moiety,

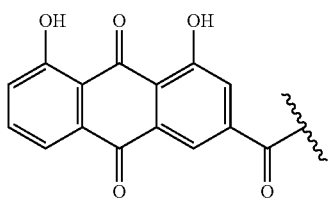 [SMILES: *C(=O)c1cc(O)c2c(c1)C(=O)c1cccc(O)c1C2=O]

refers to a rhein moiety,

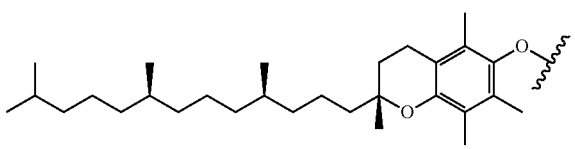 [SMILES: *Oc1c(C)c(C)c2c(c1C)CC[C@@](C)(CCC[C@H](C)CCC[C@H](C)CCCC(C)C)O2]

refers to a vitamin E moiety.

As used herein, the terms "dendritic polymer" refer to branched polymers containing a focal point, a plurality of branched monomer units, and a plurality of end groups. The monomers are linked together to form arms (or "dendritic polymer") extending from the focal point and terminating at the end groups. The focal point of the dendritic polymer can be attached to other segments of the compounds of the disclosure, and the end groups may be further functionalized with additional chemical moieties.

As used herein, the term "nanocarrier" refers to a micelle resulting from aggregation of telodendrimer conjugates of the present disclosure. The nanocarrier has a hydrophobic core and a hydrophilic exterior.

As used herein, the terms "monomer" and "monomer unit" refer to a diamino carboxylic acid, a dihydroxy carboxylic acid, or a hydroxylamino carboxylic acid. Examples of diamino carboxylic acid groups of the present disclosure include, but are not limited to, 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present disclosure include, but are not limited to, glyceric acid, 2,4-dihydroxybutyric acid, glyceric acid, 2,4-dihydroxybutyric acid, 2,2-bis(hydroxymethyl)propionic acid, and 2,2-bis(hydroxymethyl)butyric acid. Examples of hydroxyl amino carboxylic acids include, but are not limited to, serine and homoserine. One of skill in the art will appreciate that other monomer units can be used in the present disclosure.

As used herein, the term "linker" refers to a chemical moiety that links (e.g., via covalent bonds) one segment of a dendritic conjugate to another segment of the dendritic conjugate. The types of bonds used to link the linker to the segments of the telodendrimers include, but are not limited to, amides, amines, esters, carbamates, ureas, thioethers, thiocarbamates, thiocarbonate, and thioureas. For example, the linker (L, $L^1$, $L^2$, and/or $L^3$), individually at each occurrence in the telodendrimer, can be a polyethylene glycol moiety, polyserine moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. The linker can also be a cleavable linker. In certain embodiments, combinations of linkers can be used. For example, the linker can be an enzyme cleavable peptide moiety, disulfide bond moiety or an acid labile moiety. One of skill in the art will appreciate that other types of bonds can be used in the present disclosure. In certain embodiments, the linker L, $L^1$, $L^2$, and/or $L^3$ can be

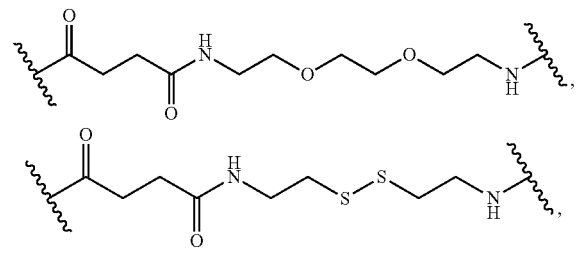

or a combination thereof.

As used herein, the term "reversible photocrosslinking group" refers to a chemical moiety that can be reversible reacted with another chemical moiety that will crosslink and decrosslink when exposed to certain conditions (e.g., UV light of varying wavelength). For example, a coumarin derivative moiety, can be photocrosslinked at >300 nm and decrosslinked at ~265 nm. The degree of crosslinking can be controlled by the amount of time the reversible photocrosslinkable groups are exposed to UV light.

As used herein, the term "oligomer" refers to fifteen or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as, for example, cholesterol, and certain polymers such as, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as, for example, PEG.

As used herein, the term "amphiphilic compound" refers to a compound having both hydrophobic portions and hydrophilic portions. For example, the amphiphilic compounds of the present disclosure can have one hydrophilic face of the compound and one hydrophobic face of the compound.

As used herein, the terms "drug" or "therapeutic agent" refers to an agent capable of treating and/or ameliorating a condition or disease. A drug may be a hydrophobic drug, which is any drug that repels water. Hydrophobic drugs useful in the present disclosure include, but are not limited to, paclitaxel, doxorubicin, etoposide, irinotecan, SN-38, cyclosporin A, podophyllotoxin, Carmustine, Amphotericin (Amphotericin B), Ixabepilone, Patupilone (epothelone class), rapamycin, bortezomib, gambogic acid, oridonin, norcantharidin, triptolide, camptothecin, docetaxel, daunorubicin, VP 16, prednisone, methotrexate, dexamethasone, vincristine, vinblastine, temsirolimus, and platinum drugs (e.g., cisplatin, carboplatin, oxaplatin). The drugs of the present disclosure also include prodrug forms and drug-like compounds. One of skill in the art will appreciate that other drugs can be used in the present disclosure.

As used herein, the term "imaging agent" refers to chemicals that allow body organs, tissue or systems to be imaged. Exemplary imaging agents include, but are not limited to, paramagnetic agents, optical probes, and radionuclides.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals. Suitable examples of mammals include, but are not limited to, primates (e.g., humans), cows, sheep, goats, horses, dogs, cats, rabbits, rats, mice, and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

Telodendrimers.

In an aspect the present disclosure provides telodendrimers. The telodendrimers are functional segregated telodendrimers having, for example, two or three functional segments. The telodendrimers can have one or more crosslinking groups (e.g., reversible photocrosslinking groups).

The telodendrimers may have a PEG groups. Without intending to be bound by any particular theory, it is considered that the PEG layer serves as a stealth hydrophilic shell to stabilize the nanoparticle and to avoid systemic clearance by the reticuloendothelial system (RES); the intermediate layer contains for example, optional crosslinkable functional group(s), amphiphilic oligo-cholic acid, riboflavin, or chlorogenic acid and can further stabilize nanoparticle and cage drug molecules in the core of nanoparticle; the interior layer contains drug-binding building blocks, such as vitamins (α-tocopherol, riboflavin, folic acid, retinoic acid, etc.) functional lipids (ceramide), chemical extracts (rhein, coumarin, curcurmine, etc) from herbal medicine to increase the affinity to drug molecules.

In an aspect, the present disclosure provides telodendrimers having three functional segments. In an embodiment, the telodendrimer is a tri-block telodendrimer system with segregated functional regions.

In an embodiment, the disclosure provides a compound of formula (I):

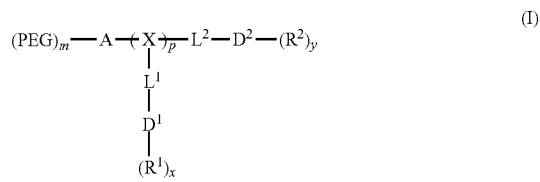

where PEG is optionally present and is a polyethylene glycol, where the PEG has a molecular weight of 44 Da to 100 kDa, including all integer kDa values and ranges therebetween; A is a monomer or oligomer linked to the PEG group; X is a branched monomer unit; each $L^1$ is independently optional and is a linker group linked to the focal point group of the dendritic polymer and monomer unit X; each $L^2$ is independently optional and is a linker group linked to the focal point group of the dendritic polymer and monomer unit X; $D^1$ is optional or a dendritic polymer having a single focal point group, one or more branched monomer units X, a plurality of end groups, and optionally, one or more linker groups $L^1$; $D^2$ is a dendritic polymer having a single focal point group, one or more branched monomer units X, a plurality of end groups, and optionally, one or more linker groups ($L^3$); each $L^3$ is independently optional or a linker group linked to the focal point group of the dendritic polymer and monomer unit (X); $R^1$ and $R^2$ are the end groups of the dendritic polymer and are independently at each occurrence in the compound selected from the group consisting of a hydrophobic group, a hydrophilic group, an amphiphilic group, a reversible photocrosslinking group, and a drug; subscript x is an integer from 1 to 64, including all integer values and ranges therebetween, wherein subscript x is equal to the number of end groups on the dendritic polymer; subscript y is an integer from 2 to 64, including all integer values and ranges therebetween, wherein subscript y is equal to the number of end groups on the dendritic polymer; subscript p is an integer from 1 to 32, including all integer values and ranges therebetween; and subscript m is an integer from 0 to 32, including all integer values and ranges therebetween.

In an embodiment, at each occurrence in the compound the branched monomer unit (X) in the compound of formula (I) is independently selected from the group consisting of a diamino carboxylic acid moiety, a dihydroxy carboxylic acid moiety, and a hydroxylamino carboxylic acid moiety.

In an embodiment, at each occurrence in the compound the diamino carboxylic acid in the compound of formula (I) is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl)pentanoic acid. In an embodiment, the diamino carboxylic acid moiety in the compound of formula (I) is an amino acid moiety. In an embodiment, each branched monomer unit (X) in the compound of formula (I) is a lysine moiety.

In various embodiments, the telodendrimer compound of the present disclosure has the following structure:

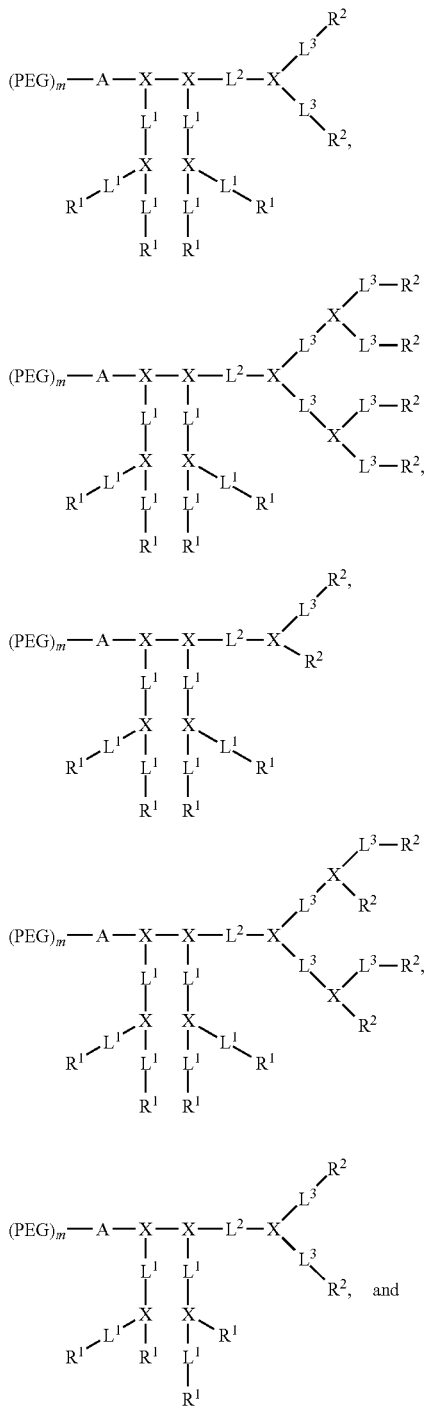

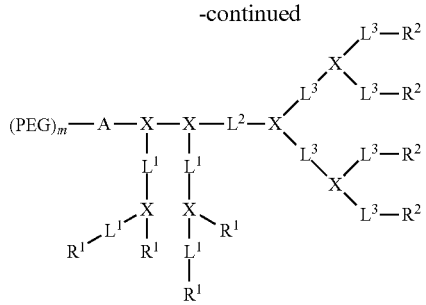

where each branched monomer unit is lysine moiety.

In an embodiment, at each occurrence in the compound the linker $L^1$, $L^2$, and $L^3$ in the compound of formula (I) are independently at each occurrence selected from the group consisting of a polyethylene glycol moiety, polyserine moiety, enzyme cleavable peptide moiety, disulfide bond moiety, acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. In an embodiment, at each occurrence in the compound the linker $L^1$, $L^2$, and $L^3$ independently at each occurrence selected from the group consisting of:

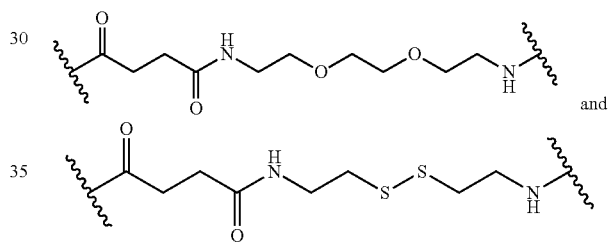

in the compound of formula (I). In an embodiment, the linker $L^1$, $L^2$, $L^3$, or a combination thereof comprises a cleavable group in the compound of formula (I). In an embodiment, the cleavable group is a disulfide cleavable moiety in the compound of formula (I).

In an embodiment, the $(PEG)_m$-A- portion of the compound is selected from the group consisting of:

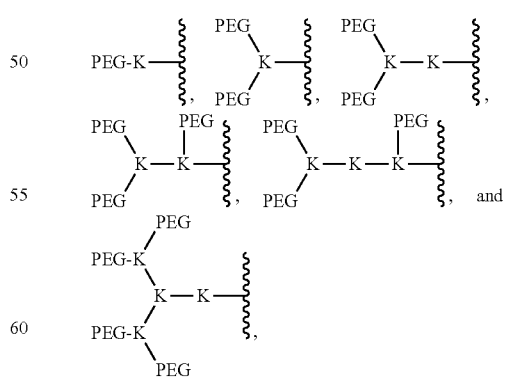

where each K is lysine in the compound of formula (I).

In an embodiment, each $R^1$ and each $R^2$ is independently selected from a rhein moiety or derivative or analog thereof, cholic acid moiety or derivative or analog thereof, moiety or derivative or analog thereof, coumarin moiety or derivative or analog thereof, curcurmine moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, Vitamin E moiety or derivative or analog thereof, D-α-tocopherol succinate moiety or derivative or analog thereof, vitamins, lipids, fatty acids, bile acids, naturally-isolated compound moieties, and drugs, and combinations thereof in the compound of formula (I). In another embodiment, each $R^1$ and/or each $R^2$ is a reversible photocrosslinking group. For example, the reversible photocrosslinking group is coumarin moiety, 4-methylcoumarin moiety, cinnamic acid moiety, chlorogenic acid moiety or derivative or analog thereof, or a combination thereof.

In an embodiment, the telodendrimer is a compound of formula (I) where x=4; y=4, m=1, PEG is 5 kDa; $R^1$ is a coumarin moiety; each $R^2$ is independently selected from the group consisting of cholic acid moiety or derivative or analog thereof, cholesterol moiety or derivative or analog thereof, rhein moiety or derivative or analog thereof, Vitamin E moiety or derivative or analog thereof, coumarin moiety or derivative or analog thereof, curcurmin moiety or derivative or analog thereof, riboflavin moiety or derivative or analog thereof, and chlorogenic acid moiety or derivative or analog thereof; $L^1$ is optional or a disulfide bond moiety; $L^2$ is an ethylene glycol linker; and $L^3$ is optional or an ethylene glycol linker.

In an embodiment, the telodendrimer is a compound of formula (I) where x=2 to 16; y=2 to 64, m=1 to 8, PEG is 1 to 40 kDa; $R^1$ is a coumarin moiety or derivative or analog thereof or cinnamic acid moiety or derivative or analog thereof; each $R^2$ is independently selected from the group consisting of cholic acid moiety or derivative or analog thereof, cholesterol moiety or derivative or analog thereof, rhein moiety or derivative or analog thereof, Vitamin E moiety or derivative or analog thereof, coumarin moiety or derivative or analog thereof, curcurmin moiety or derivative or analog thereof, riboflavin moiety or derivative or analog thereof, and chlorogenic acid moiety or derivative or analog thereof; $L^1$ is optional or a disulfide bond moiety; $L^2$ is an ethylene glycol linker; and $L^3$ is optional or an ethylene glycol linker.

In an embodiment, the telodendrimer is a compound of formula (I) where x=4; y=4, m=1, PEG is 5 kDa; $R^1$ is a cholic acid moiety or derivative or analog thereof; each $R^2$ is independently selected from the group consisting of cholesterol moiety or derivative or analog thereof, rhein, Vitamin E moiety or derivative or analog thereof, coumarin moiety or derivative or analog thereof, curcurmin moiety or derivative or analog thereof, riboflavin moiety or derivative or analog thereof, and retinoic acid moiety or derivative or analog thereof; $L^1$ is optional or a disulfide bond moiety; $L^2$ is an ethylene glycol linker; and $L^3$ is optional or an ethylene glycol linker.

In an embodiment, the telodendrimer is compound of formula (I) where x=2 to 16; y=2 to 64, m=1 to 8, PEG is 1 to 40 kDa; $R^1$ is a cholic acid moiety or derivative or analog thereof, riboflavin moiety or derivative or analog thereof or a combination thereof; each $R^2$ is independently selected from the group consisting of cholic acid moiety or derivative or analog thereof, cholesterol moiety or derivative or analog thereof, rhein moiety or derivative or analog thereof, Vitamin E moiety or derivative or analog thereof, coumarin moiety or derivative or analog thereof, curcurmin moiety or derivative or analog thereof, riboflavin moiety or derivative or analog thereof, retinoic acid moiety or derivative or analog thereof, and chlorogenic acid moiety or derivative or analog thereof; $L^1$ is optional or a disulfide bond moiety; $L^2$ is an ethylene glycol linker; and $L^3$ is optional or an ethylene glycol linker.

In an embodiment, the telodendrimer is generally described by the compound structure of FIG. 1. In various embodiments, the telodendrimer is selected from the compounds in FIGS. 2, 3, 4, 5, 6, 7, 19, 27, and 31.

In an aspect, the disclosure provides telodendrimers having 2 functional moieties, one or more cross-linkable groups, and at least one cleavable group. For example, the cross-linkable groups are photocrosslinkable groups.

In an embodiment, the telodendrimer is a compound of formula (II):

$$(PEG)_m\text{-}A\text{-}L\text{-}D\text{-}(R^3)_n \qquad (II)$$

where D is a dendritic polymer having a single focal point group, a plurality of branched monomer units (X), at least one cleavable linking group, and a plurality of end groups; L is optional or a linker group linked to the focal point group of the dendritic polymer; PEG is optionally present or a polyethylene glycol, wherein PEG has a molecular weight of 44 Da to 100 kDa, including all integer kDa values and ranges therebetween; A is a monomer or oligomer linked to the PEG group; each $R^3$ are the end groups of the dendritic polymer and are independently at each occurrence of the compound selected from the group consisting of a hydrophobic group, a hydrophilic groups, an amphiphilic group, a reversible photocrosslinking group, and a drug such that at least half the number of $R^3$ groups are a reversible photocrosslinking group; subscript n is an integer from 2 to 32, including all integer values and ranges therebetween, wherein subscript n is equal to the number of end groups on the dendritic polymer, and wherein at least half the number n of $R^3$ groups are each independently selected from the group consisting of a hydrophobic group, a hydrophilic group, an amphiphilic group, reversible photocrosslinking group and a drug; and subscript m is an integer from 0 to 32, including all integer values and ranges therebetween.

In an embodiment, the disclosure provides a compound of formula (II) where n=8, PEG is 5 kDa, each $R^3$ is independently selected from a cholic acid moiety or derivative or analog thereof, Vitamin E moiety or derivative or analog thereof, coumarin moiety or derivative or analog thereof, curcurmin moiety or derivative or analog thereof, riboflavin moiety or derivative or analog thereof, retinoic acid moiety or derivative or analog thereof, and chlorogenic acid moiety or derivative or analog thereof; A is optional or an amino acid linker; and L is optional or an ethylene glycol linker.

In an embodiment, the disclosure provides a compound of formula (II) where n=2 to 64, PEG is 1 to 40 kDa; each $R^3$ is independently selected from a cholic acid moiety or derivative or analog thereof, Vitamin E moiety or derivative or analog thereof, coumarin moiety or derivative or analog thereof, curcurmin moiety or derivative or analog thereof, riboflavin moiety or derivative or analog thereof, retinoic acid moiety or derivative or analog thereof, and chlorogenic acid moiety or derivative or analog thereof; A is optional or an amino acid linker; and L is optional, an ethylene glycol linker, a disulfide bond moiety, or a combination thereof.

In an embodiment, where the compound has the formula (II), the cleavable linking group is

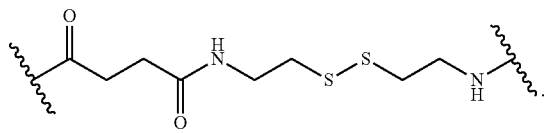 [SMILES: *NCCSSCCNC(=O)CCC(*)=O]

In an embodiment, where the compound has the formula (II), the reversible photocrosslinking group is a methylcoumarin moiety, 4-methylcoumarin moiety, cinnamic acid moiety or derivative or analog thereof, chlorogenic acid moiety or derivative or analog thereof, or a combination thereof.

In an embodiment, where the compound has the formula (II), at each occurrence of the compound the branched monomer unit (X) is independently selected from the group consisting of a diamino carboxylic acid moiety, a dihydroxy carboxylic acid moiety, and a hydroxylamino carboxylic acid moiety. In an embodiment, where the compound has the formula (II), at each occurrence of the compound the diamino carboxylic acid moiety is an amino acid moiety. In an embodiment, where the compound has the formula (II), each branched monomer unit X is lysine moiety.

In an embodiment, where the compound has the formula (II), the $(PEG)_m$-A-portion of the compound is selected from the group consisting of:

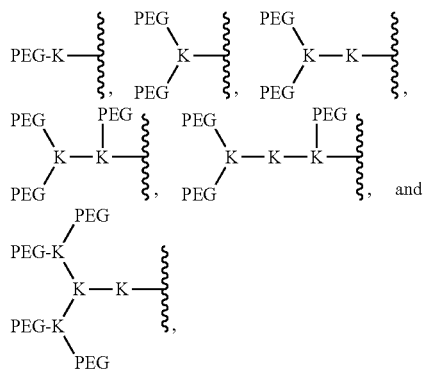

where each K is lysine.

In an aspect, the disclosure provides telodendrimers having 2 functional moieties and where half but not all of the end groups of the dendritic polymer are cholic acid, riboflavin, or a combination thereof.

In an embodiment, the telodendrimer is a compound of formula (III):

$$(PEG)_m\text{-A-L-D-}(R^3)_n \quad (III)$$

where D is a dendritic polymer having a single focal point group, a plurality of branched monomer units (X) and a plurality of end groups; L is optional or a linker group linked to the focal point group of the dendritic polymer; PEG is optional or a polyethylene glycol, wherein PEG has a molecular weight of 44 Da to 100 kDa, including all integer kDa values and ranges therebetween; A is a monomer or oligomer linked to the PEG group; each $R^3$ are the end groups of the dendritic polymer and are independently at each occurrence of the compound selected from the group consisting of a cholic acid moiety or derivative or analog thereof, a coumarin moiety or derivative or analog thereof, a Vitamin E moiety or derivative or analog thereof, a riboflavin moiety or derivative or analog thereof, and chlorogenic acid moiety or derivative or analog thereof, such that at least half but not all of the number of $R^3$ groups is a cholic acid moiety or riboflavin moiety; subscript n is an integer from 2 to 64, including all integer values and ranges therebetween, wherein subscript n is equal to the number of end groups on the dendritic polymer, and wherein at least half the number n of $R^3$ groups are each independently selected from the group consisting of a cholic acid moiety or derivative or analog thereof, a coumarin moiety or derivative or analog thereof, a Vitamin E moiety or derivative or analog thereof, a riboflavin moiety or derivative or analog thereof, and a chlorogenic acid moiety or derivative or analog thereof; and subscript m is an integer from 0 to 32, including all integer values and ranges therebetween.

In an embodiment, the telodendrimer is a compound of formula (II) where n=8 and four of the $R^3$'s are a cholic acid moiety or derivative or analog thereof and four $R^3$'s are a coumarin moiety or derivative or analog thereof. In an embodiment, the disclosure provides a compound of formula (II) where n=8 and four of the $R^3$'s are a cholic acid moiety or derivative or analog thereof and four $R^3$'s are a Vitamin E moiety or derivative or analog thereof. In an embodiment, the disclosure provides a compound of formula (II) where n=8 and four of the $R^3$'s are a cholic acid moiety or derivative or analog thereof and four $R^3$'s are a riboflavin moiety or derivative or analog thereof. In an embodiment, the disclosure provides a compound of formula (II) where n=8 and four of the $R^3$'s are a riboflavin moiety or derivative or analog thereof and four $R^3$'s are a Vitamin E moiety or derivative or analog thereof.

In an embodiment, where the telodendrimer is a compound of formula (III) where at each occurrence in the compound the branched monomer unit (X) is independently selected from the group consisting of a diamino carboxylic acid moiety, a dihydroxy carboxylic acid moiety, and a hydroxyl amino carboxylic acid moiety. In an embodiment, where the compound has the formula (III), at each occurrence in the compound the diamino carboxylic acid moiety is an amino acid moiety. In an embodiment, where the compound has the formula (III), each branched monomer unit (X) is a lysine moiety.

In an embodiment, where the telodendrimer is a compound of formula (III) where each diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl)pentanoic acid.

In an embodiment, where the telodendrimer is a compound of formula (III) where the $(PEG)_m$-A- portion of the compound is selected from the group consisting of:

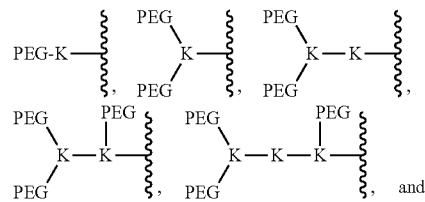

-continued

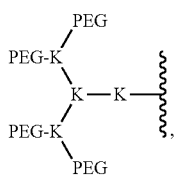

where each K is lysine.

In an aspect, the present disclosure provides telodendrimers where the end groups of the dendritic polymer are selected from a coumarin moiety or derivative or analog thereof, curcurmine moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, anthraquinone moiety or derivative or analog thereof, xanthenone moiety or derivative or analog thereof, Vitamin E moiety or derivative or analog thereof, and D-α-tocopherol succinate moiety or derivative or analog thereof, vitamins, lipids, fatty acids, bile acids, naturally-isolated compound moieties, and drugs.

In an embodiment, the telodendrimer is a compound of formula (IV):

where D is a dendritic polymer having a single focal point group, a plurality of branched monomer units (X), at least one cleavable linking group, and a plurality of end groups; L is optional or a linker group linked to the focal point group of the dendritic polymer; PEG is optionally present or a polyethylene glycol, wherein PEG has a molecular weight of 44 Da to 100 kDa, including all integer kDa values and ranges therebetween; A is a monomer or oligomer linked to the PEG group; each $R^3$ are the end groups of the dendritic polymer and are independently at each occurrence in the compound selected from the group consisting of a coumarin moiety or derivative or analog thereof, curcurmine moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, Vitamin E moiety or derivative or analog thereof, and D-α-tocopherol succinate moiety or derivative or analog thereof, vitamins, lipids, fatty acids, bile acids, naturally-isolated compound moieties, and drugs; subscript n is an integer from 2 to 64, including all integer values and ranges therebetween, wherein subscript n is equal to the number of end groups on the dendritic polymer, and wherein at least half the number n of $R^3$ groups are each independently selected from the group consisting of a coumarin moiety or derivative or analog thereof, curcurmine moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, Vitamin E moiety or derivative or analog thereof, and D-α-tocopherol succinate moiety or derivative or analog thereof, vitamins, lipids, fatty acids, bile acids, naturally-isolated compound moieties, and drugs; and subscript m is an integer from 0 to 32, including all integer values and ranges therebetween.

In an embodiment, the telodendrimer is a compound of formula (IV) where at each occurrence in the compound the branched monomer unit (X) is independently selected from the group consisting of a diamino carboxylic acid moiety, a dihydroxy carboxylic acid moiety, and a hydroxyl amino carboxylic acid moiety.

In an embodiment, the telodendrimer is a compound of formula (IV) where each diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl)pentanoic acid. In an embodiment, where the compound has the formula (IV), the diamino carboxylic acid moiety is an amino acid moiety. In an embodiment, where the compound has the formula (IV), each branched monomer unit X is lysine moiety.

In an embodiment, the telodendrimer is a compound of formula (IV) where PEG is 1 to 40 kDa; each $R^3$ is independently selected from a Vitamin E moiety or derivative or analog thereof, coumarin moiety or derivative or analog thereof, curcurmin moiety or derivative or analog thereof, riboflavin moiety or derivative or analog thereof, and retinoic acid moiety or derivative or analog thereof; A is optional or an amino acid linker; and L is optional, an ethylene glycol linker, a disulfide bond moiety, or a combination thereof.

In an embodiment, the telodendrimer is a compound of formula (IV) where the $(PEG)_m$-A- portion of the compound is selected from the group consisting of:

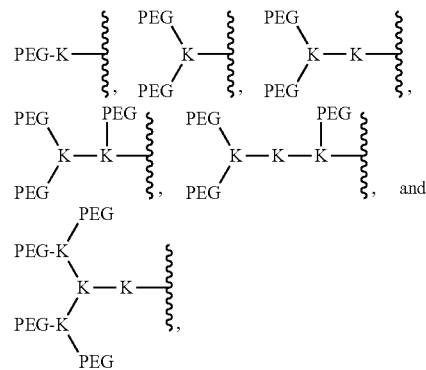

wherein each K is lysine.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit (X) can be a diamino carboxylic acid, a dihydroxy carboxylic acid and a hydroxylamino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2- aminomethyl propanoic acid, 3-amino-2-aminomethyl-2-methyl propanoic acid, 4-amino-2-(2-aminoethyl) butyric acid, or 5-amino-2-(3-aminopropyl)pentanoic acid. In some embodiments, each dihydroxy carboxylic acid can be glyceric acid, 2,4-dihydroxybutyric acid, 2,2-bis(hydroxymethyl)propionic acid, 2,2-bis(hydroxymethyl)butyric acid, serine, or threonine. In some embodiments, each hydroxyl amino carboxylic acid can be serine or homoserine. In some embodiments, the diamino carboxylic acid is an amino acid. In some embodiments, each branched monomer unit X is lysine.

The dendritic polymer of the telodendrimer can be any suitable generation of dendritic polymer, including generation 1, 2, 3, 4, 5, or more, where each "generation" of dendritic polymer refers to the number of branch points encountered between the focal point and the end group following one branch of the dendritic polymer. The dendritic polymer of the telodendrimer can also include partial-generations such as 1.5, 2.5, 3.5, 4.5, 5.5, etc., where a branch point of the dendritic polymer has only a single branch. The various architectures of the dendritic polymer can provide any suitable number of end groups, including, but not limited to, 2 to 128 end groups and all integer value of end groups and ranges therebetween.

The focal point of a dendritic polymer, telodendrimer, dendritic polymer segment, or telodendrimer segment may be any suitable functional group. In some embodiments, the focal point includes a functional group that allows for attachment of dendritic polymer, telodendrimer, dendritic polymer segment, or telodendrimer segment to another segment. The focal point functional group can be a nucleophilic group including, but not limited to, an alcohol, an amine, a thiol, or a hydrazine. The focal point functional group may also be an electrophile such as an aldehyde, a carboxylic acid, or a carboxylic acid derivative including an acid chloride or an N-hydroxysuccinimidyl ester.

The $R^1$, $R^2$, $R^3$ groups installed at the telodendrimer periphery can be any suitable chemical moiety, including hydrophilic groups, hydrophobic groups, amphiphilic compounds, or photocrosslinking groups. Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

In certain embodiments, each $R^1$ and $R^2$ is independently selected from a rhein moiety or derivative or analog thereof, cholic acid moiety or derivative or analog thereof, coumarin moiety or derivative or analog thereof, curcurmine moiety or derivative or analog thereof, flavin moiety or derivative or analog thereof, isoflavin moiety or derivative or analog thereof, retinol moiety or derivative or analog thereof, retinoic acid moiety or derivative or analog thereof, anthraquinone moiety or derivative or analog thereof, xanthenone moiety or derivative or analog thereof, Vitamin E moiety or derivative or analog thereof, D-α-tocopherol succinate moiety or derivative or analog thereof, Vitamins, lipids, fatty acids, Bile acids, naturally-isolated compound moieties, and drugs. In certain embodiments, $R^1$ and/or $R^2$ is a reversible photocrosslinking group. Examples of reversible photocrosslinking group moities include methylcoumarin moiety, 4-methylcoumarin moiety, or cinnamic acid moiety or derivatives or analogs thereof.

In certain embodiments, each $R^3$ is independently selected from a rhein moiety or derivative or analog thereof, cholic acid moiety or derivative or analog thereof, coumarin moiety or derivative or analog thereof, curcurmine moiety or derivative or analog thereof, flavin moiety or derivative or analog thereof, isoflavin moiety or derivative or analog thereof, retinol moiety or derivative or analog thereof, retinoic acid moiety or derivative or analog thereof, anthraquinone moiety or derivative or analog thereof, xanthenone moiety or derivative or analog thereof, Vitamin E moiety or derivative or analog thereof, D-α-tocopherol succinate moiety or derivative or analog thereof, vitamins, lipids, fatty acids, bile acids, naturally-isolated compound moieties, and drugs. In certain embodiments, $R^3$ is a reversible photocrosslinking group moiety. Examples of reversible photocrosslinking group moities include methylcoumarin moiety, 4-methylcoumarin moiety, or cinnamic acid moiety or derivatives or analogs thereof.

In certain embodiments, the end groups of the telodendrimer can alternate between groups. For example, $R^1$ can be a cholic acid moiety and a rhein moiety and adjacent $R^1$'s can alternate between these two moieties. This can be applied to $R^2$ and $R^3$.

The telodendrimers of the present disclosure can be synthesized via peptide chemistry, which can control the chemical structure and the architecture of the telodendrimers. Efficient stepwise peptide chemistry allows for reproducibility and scaling up for clinical development. In addition, given their structure, the telodendrimers can self-assemble into micelle nanoparticles with controlled and tunable properties, such as particle size, drug loading capacity and stability. Cholic acid is a facial amphiphilic biomolecule. As a core-forming building block, cholic acid can play a role in stabilizing nanoparticle and the drug molecules loaded in the nanoparticles. Drug-binding bioactive and biocompatible molecules can be introduced into telodendrimer in the core of the micelle to improve the drug loading capacity and stability.

With the aid of computational approaches, a number of natural bioactive compounds for design and synthesis of telodendrimers with segregated functional layers for efficient delivery of specific drug molecules were examined, (e.g., paclitaxel, docetaxel, etopside, doxorubicin, daunorubicin, SN-38, gambogic acid, norcanthardine, oridonine and triptolide, etc). The loading capacity and stability of these nanotherapeutics have been significantly improved via engineering the topology of the telodendrimers. The particle sizes of these nanoformulations can be within the optimal range of 10-30 nm for efficient in vivo tumor targeting. In an embodiment, the core or shell photo-crosslinked nanocarrier significantly increased the stability of the nanoformulations with the capability of the reversible decrosslinking for on-demand drug release in response to the reducing intratumoral microenviorment.

Nanocarriers.

In an aspect the present disclosure provides nanocarriers comprising the telodendrimers. The empty nanocarriers were examined to be nontoxic in cell culture and the drug-loaded nanoformulations exhibited the similar potency in killing cancer cells in vitro, and better anticancer effects in vivo, due to the tumor targeted drug delivery. The in vivo maximum tolerate dose of doxorubicin has been increased 100% after loaded into nanocarriers compared with the free formulation. The resulting nanocarriers exhibit superior drug loading capacity and stability. The side toxicities of the chemodrugs were significantly reduced via nanoformulation. The optimized nanoparticle is able to target delivery of the payload chemo drugs to the cancer site. As a result, custom designed telodendrimer nanotherapeutics significantly improve the anticancer effects in vivo.

The telodendrimers of the present disclosure can aggregate to form nanocarriers with a hydrophobic core and a hydrophilic exterior. In an embodiment, a plurality of telodendrimers aggregate to form nanocarriers with a hydrophobic core and a hydrophilic exterior. In an embodiment, the disclosure provides a nanocarrier having an interior and an exterior, the nanocarrier comprising a plurality of the telodendrimer conjugates of the disclosure, wherein each compound self-assembles in an aqueous solvent to form the nanocarrier such that a hydrophobic pocket is formed in the interior of the nanocarrier, and wherein the hydrophilic segment (e.g., PEG) of each compound self-assembles on the exterior of the nanocarrier.

In an embodiment, the nanocarrier comprises a hydrophobic drug or an imaging agent, such that the hydrophobic drug or imaging agent is sequestered in the hydrophobic pocket of the nanocarrier. Hydrophobic drugs useful in the nanocarrier of the present disclosure include any drug having low water solubility. In some embodiments, the hydrophobic drug in the nanocarrier can be bortezomib, gambogic acid, oridonin, norcantharidin, triptolide, paclitaxel, SN38, amphotericin B, camptothecin, etoposide and doxorubicin, docetaxel, daunorubicin, VP 16, prednisone, methotrexate, cisplatin, carboplatin, oxapaltin, dexamethasone, vincristine, vinblastine, temsirolimus, and carmusine.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic drugs that are sequestered in the interior of the nanocarriers of the present disclosure.

Drugs that can be sequestered in the nanocarriers or linked to the conjugates of the present disclosure include, but are not limited to, cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present disclosure include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the disclosure.

Other drugs useful in the present disclosure also include radionuclides, such as $^{67}$Cu, $^{90}$Y, $^{123}$I, $^{125}$I, $^{131}$I, $^{177}$Lu, $^{188}$Re, $^{186}$Re and $^{211}$At. In some embodiments, a radionuclide can act therapeutically as a drug and as an imaging agent.

Imaging agents include paramagnetic agents, optical probes and radionuclides. Paramagnetic agents include iron particles, such as iron nanoparticles that are sequestered in the hydrophobic pocket of the nanocarrier.

Some embodiments of the present disclosure provide nanocarriers wherein each amphiphilic compound $R^1$, $R^2$, and/or $R^3$ is independently cholic acid, allocholic acid, pythocholic acid, avicholic acid, deoxycholic acid, or chenodeoxycholic acid.

Method of Treating.

The nanocarriers of the present disclosure can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier.

In some embodiments, the present disclosure provides a method of treating a disease, including administering to a subject in need of such treatment a therapeutically effective amount of a nanocarrier of the present disclosure, where the nanocarrier includes a drug. The drug can be a covalently attached to a conjugate of the nanocarrier. In some embodiments, the drug is a hydrophobic drug sequestered in the interior of the nanocarrier. In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The nanocarriers of the present disclosure can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present disclosure include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the nanocarriers of the present disclosure are useful for the treatment of infection by pathogens such as viruses, bacteria, fungi, and parasites. Other diseases can be treated using the nanocarriers of the present disclosure.

Formulations.

The nanocarriers of the present disclosure can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present disclosure (see, e.g., Remington's Pharmaceutical Sciences, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present disclosure suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the disclosure in a sustained release formulation.

Pharmaceutical preparations useful in the present disclosure also include extended-release formulations. In some embodiments, extended-release formulations useful in the present disclosure are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present disclosure, the pharmaceutical compositions can be used alone, or in combination with other therapeutic or diagnostic agents.

Administration.

The nanocarriers of the present disclosure can be administered as frequently as necessary, including hourly, daily, weekly or monthly. The compounds utilized in the pharmaceutical method of the disclosure are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present disclosure should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present disclosure, the pharmaceutical compositions can be used alone, or in combination with other therapeutic or diagnostic agents. The additional drugs used in the combination protocols of the present disclosure can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present disclosure, separately or at different times.

Method of Imaging.

In some embodiments, the present disclosure provides a method of imaging, including administering to a subject to be imaged, an effective amount of a nanocarrier of the present disclosure, wherein the nanocarrier includes an imaging agent. In other embodiments, the method of treating and the method of imaging are accomplished simultaneously using a nanocarrier having both a drug and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present disclosure include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present disclosure include, but are not limited to, $^{3}H$, $^{11}C$, $^{13}N$, $^{18}F$, $^{19}F$, $^{60}Co$, $^{64}Cu$, $^{68}Ga$, $^{82}Rb$, $^{90}Sr$, $^{90}Y$, $^{99}Tc$, $^{99m}Tc$, $^{111}In$, $^{123}I$, $^{124}I$, $^{125}I$, $^{129}I$, $^{131}I$, $^{137}Cs$, $^{177}Lu$, $^{186}Re$, $^{188}Re$, $^{211}At$, Rn, Ra, Th, U, Pu and $^{241}Am$.

The following examples are presented to illustrate the present disclosure. They are not intended to limiting in any manner.

Example 1

This example shows examples of syntheses of telodendrimers and supporting data of same of the present disclosure. The claimed functional segregated telodendrimer system (linear dendritic copolymer) allows for the customized design of the polymer architecture and structures for the efficient delivery of a specific drug with improved loading capacity and stability.

Experiments. Materials.

Monomethoxyl terminated poly(ethylene glycol) monoamine (MeO-PEG-NH$_2$, Mw: 5000 Da) was purchased from JenKem (Dallas, Tex.). (Fmoc)lys(Boc)-OH, (Boc)Lys(Boc)-OH, (Fmoc)Lys(Fmoc)-OH and (Fmoc)Ebes-COOH were purchased from AnaSpec Inc. (San Jose, Calif.). 1,1'-dioctadecyl-3,3,3',3'-tetramethylindodicarbocyanine perchlorate (DiD) were purchased from Invitrogen (Carlsbad, Calif.). GA, ORD and NCTD were purchased from Xi'an Xuhuang Bio-tech Co. Ltd. (Xian, China). Cholic acid, MTT [3-(4,5-dimethyldiazol-2-yl)-2,5diphenyl tetrazolium bromide] and all other chemicals were purchased from Sigma-Aldrich (St. Louis).

Telodendrimer Synthesis. Synthesis of PEG$^{5k}$-CA$_4$-L-VE$_4$ and PEG$^{5k}$-CA$_4$-L-RH$_4$.

Figure 8:
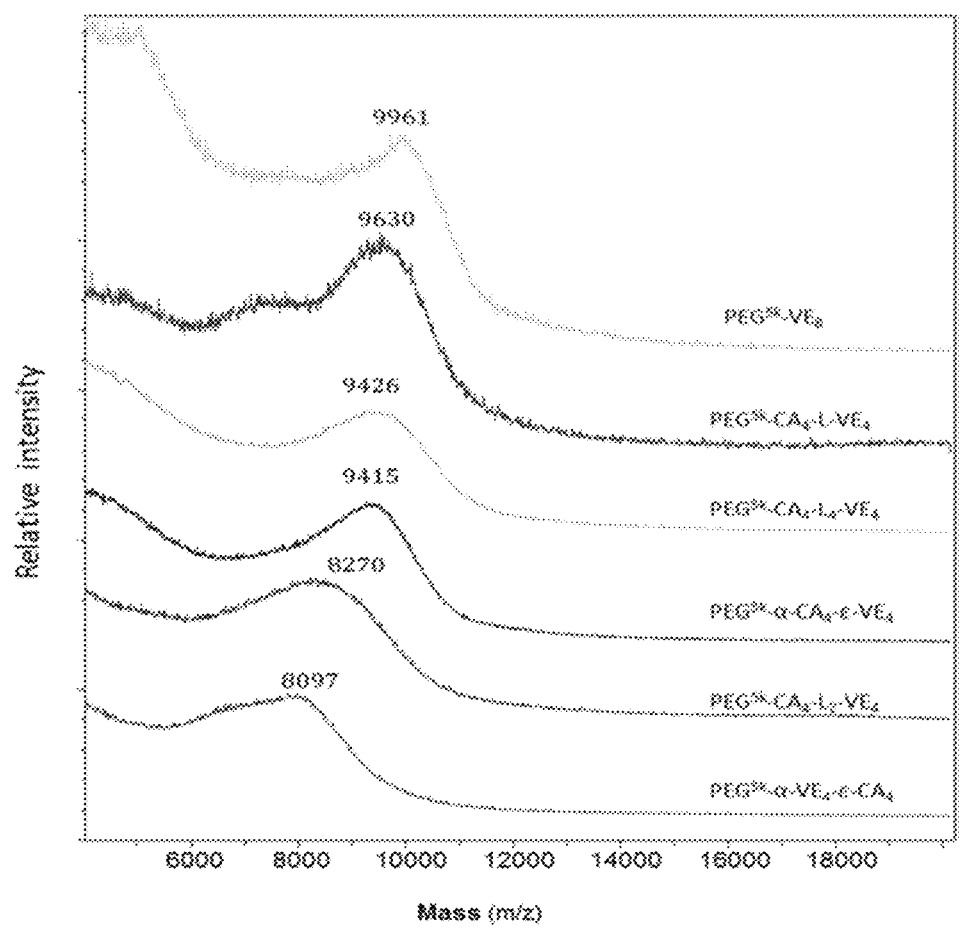
FIG. 8. MALDI-ToF mass spectra of examples of VE containing telodendrimers.

The polymer containing one PEG linker (MW: 470), four cholic acids and four D-α-tocopherol succinates (named as PEG$^{5k}$-CA$_4$-L-VE$_4$, FIG. 8) was synthesized via solution-phase condensation reactions from MeO-PEG-NH$_2$ via stepwise peptide chemistry. The typical procedure for synthesis of PEG$^{5k}$-CA$_4$-L-VE$_4$ is as follows: (Fmoc)Lys(Boc)-OH (3 eq.) was coupled onto the N terminus of PEG using DIC and HOBt as coupling reagents until a negative Kaiser test result was obtained, thereby indicating completion of the coupling reaction. PEGylated molecules were precipitated by adding cold ether and then washed with cold ether twice. Fmoc groups were removed by the treatment with 20% (v/v) 4-methylpiperidine in dimethylformamide (DMF), and the PEGylated molecules were precipitated and washed three times with cold ether. White powder precipitate was dried under vacuum, and consecutive coupling of (Fmoc)Lys(Boc)-OH, PEG linker and two couplings of (Fmoc)lys(Fmoc)-OH were performed respectively upon the removal of Fmoc groups to generate an intermediate of dendritic polylysine terminated with four Fmoc groups on the peripheral of polymer. Then (Boc)lys(Boc)-OH were coupled to the amino groups of the proximal lysines between PEG and PEG linker upon the removal of Boc groups with 50% (v/v) trifluoroacetic acid (TFA) in dichloromethane (DCM). Cholic acid NHS ester were then coupled to the amino groups of the proximal lysines upon the removal of Boc groups. After the removal of four peripheral Fmoc groups, part of the polymer was coupled with D-α-tocopherol succinates resulting in PEG$^{5k}$-CA$_4$-L-VE$_4$, and the other part of the polymer was coupled with Rhein-NHS resulting in PEG$^{5k}$-CA$_4$-L-RH$_4$ (FIG. 8).

Synthesis of PEG$^{5k}$-CA$_4$-L$_2$-VE$_4$ and PEG$^{5k}$-CA$_4$-L$_4$-VE$_4$.

Figure 9:
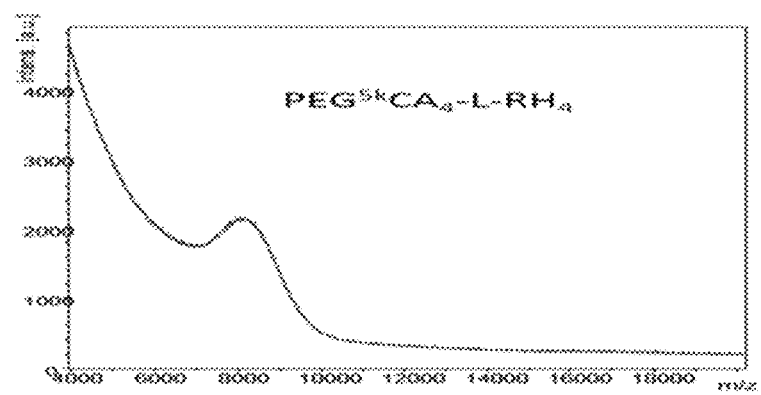
FIG. 9. The MALDI-TOF MS of examples of trilayered telodendrimers with rhein as building blocks.

The polymer containing two or four PEG linker (MW: 470), four cholic acids and four D-α-tocopherol succinates (named as PEG$^{5k}$-CA$_4$-L$_2$-VE$_4$ or PEG$^{5k}$-CA$_4$-L$_4$-VE$_4$, FIG. 9) was synthesized via solution-phase condensation reactions from MeO-PEG-NH$_2$ via stepwise peptide chemistry. The procedure was described as follows: (Fmoc)Lys(Boc)-OH (3 eq.) was reacted with the N terminus of PEG using DIC and HOBt as coupling reagents until a negative Kaiser test result was obtained, thereby indicating completion of the coupling reaction. PEGylated molecules were precipitated by the addition of cold ether and then washed with cold ether twice. Boc groups were removed via the treatment with 50% (v/v) trifluoroacetic acid (TFA) in dichloromethane (DCM). The PEGylated intermediate were precipitated and washed three times with cold ether. White powder precipitate was dried under vacuum. Then the consecutive coupling of (Fmoc)Lys(Boc)-OH and two couplings of (Boc)lys(Boc)-OH were carried out respectively upon the removal of Boc groups to generate an intermediate of dendritic polylysine terminated with four Boc groups on one end of PEG. Then two PEG linker molecules were coupled to the amino groups upon the removal of Fmoc groups with 20% (v/v) 4-methylpiperidine in dimethylformamide (DMF). Two (Fmoc)Lys(Fmoc)-OH were coupled to the amino groups upon the removal of Fmoc groups at the PEG linker. After the removal of four Fmoc groups, cholic acid NHS ester were then coupled to the free amino groups on lysines. Finally, the polymer was coupled with D-α-tocopherol succinates after the removal of Boc groups resulting in PEG$^{5k}$-CA$_4$-L$_2$-VE$_4$ (FIG. 9). The synthesis procedure of PEG$^{5k}$-CA$_4$-L$_4$-VE$_4$ is similar with the PEG$^{5k}$-CA$_4$-L$_2$-VE$_4$, the only difference is to couple (Fmoc)Lys(Boc)-OH to the amino groups of the lysines before coupling the PEG linker molecules (FIG. 9).

Synthesis of PEG$^{5k}$-VE$_8$.

Figure 10:
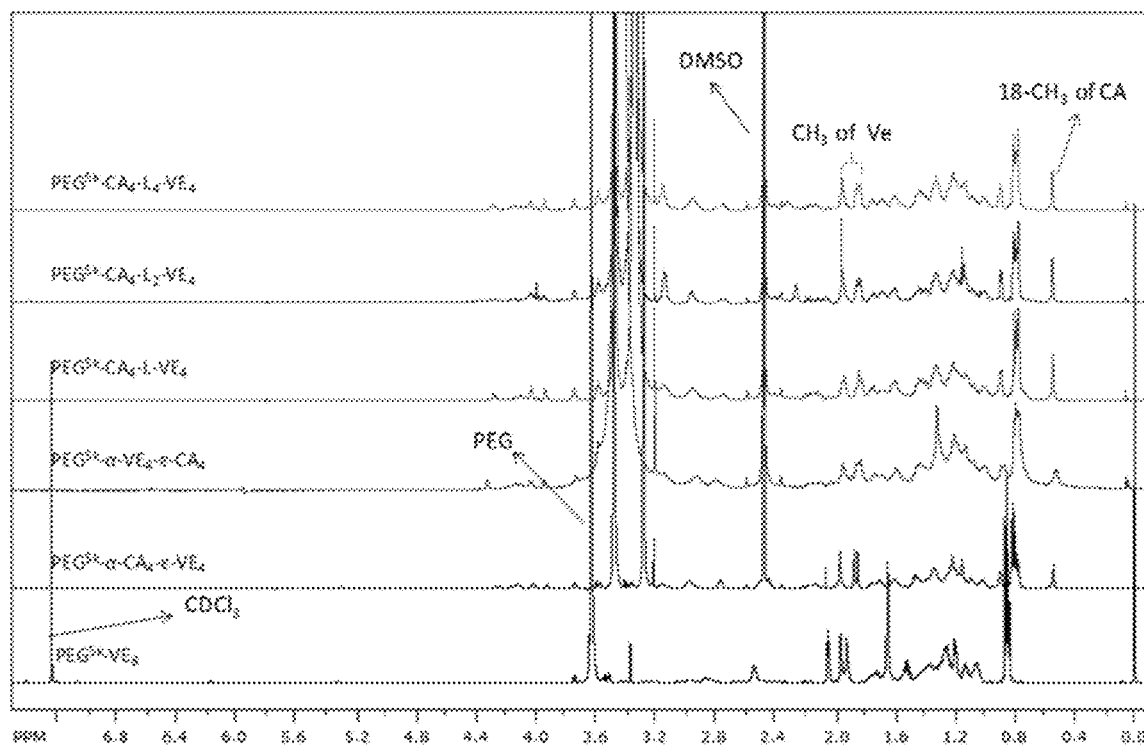
FIG. 10. $^1H$ NMR spectra of examples of VE containing polymers recorded in DMSO-$d_6$ and $CDCl_3$.

The polymer containing eight D-α-tocopherol succinates (named as PEG$^{5k}$-VE$_8$, FIG. 10) was synthesized via solution-phase condensation reactions from MeO-PEG-NH$_2$ via stepwise peptide chemistry. The procedure was as follows: (Fmoc)Lys(Fmoc)-OH (3 eq.) reacted with the N terminus of PEG using DIC and HOBt as coupling reagents until a negative Kaiser test result was obtained, thereby indicating completion of the coupling reaction. PEGylated molecules were precipitated via the addition of the cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum and two additional repeated couplings of (Fmoc)Lys(Fmoc)-OH were carried out to generate a third generation of dendritic polylysine on one end of PEG. D-α-tocopherol succinates was coupled to the terminal end of dendritic polylysine in the presence of triethylamine resulting in PEG$^{5k}$-VE$_8$ (FIG. 10).

Synthesis of PEG$^{5k}$-α-VE$_4$-ε-CA$_4$ and PEG$^{5k}$-α-CA$_4$-ε-VE$_4$.

Figure 11:
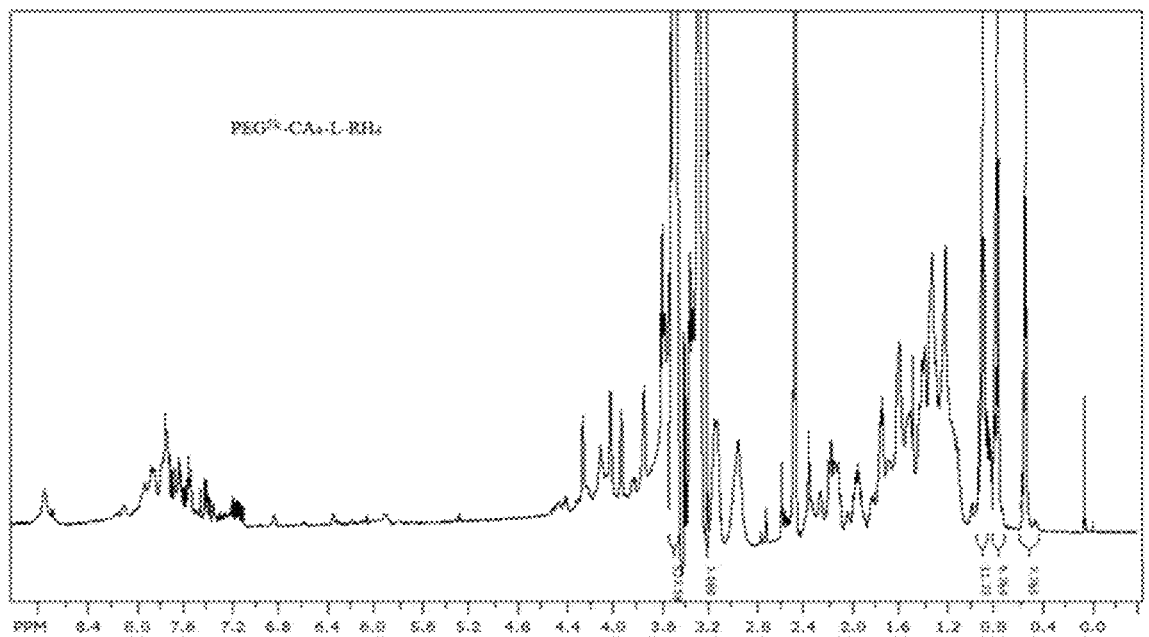
FIG. 11. $^1H$ NMR spectra of an example of a trilayered telodendrimer, $PEG^{5k}CA_4\text{-L-}RH_4$, recorded in DMSO-$d_6$.

The polymer containing four D-α-tocopherol succinates and four cholic acid (named as PEG$^{5k}$-α-VE$_4$-ε-CA$_4$ and PEG$^{5k}$-α-CA$_4$-ε-VE$_4$, FIG. 11) was synthesized via solution-phase condensation reactions from MeO-PEG-NH$_2$ via stepwise peptide chemistry. The procedure was as follows: (Fmoc)Lys(Fmoc)-OH (3 eq.) was coupled onto the N terminus of PEG using DIC and HOBt as coupling reagents until a negative Kaiser test result was obtained, thereby indicating completion of the coupling reaction. PEGylated molecules were precipitated by adding cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum, one coupling of (Fmoc)Lys(Fmoc)-OH and one coupling of (Fmoc)lys(Boc)-OH were carried out respectively upon the removal of Fmoc groups to generate an intermediate of dendritic polylysine terminated with four Boc groups and four Fmoc groups on one end of PEG. After the removal of Fmoc groups, two portions of the polymer were coupled with D-α-tocopherol succinate and cholic acid NHS, respectively. Consecutively, the Boc protecting groups were removed via the treatment with 50% TFA in DCM were coupled with cholic acid NHS and D-α-tocopherol succinate, respectively, to yield PEG$^{5k}$-α-VE$_4$-ε-CA$_4$ and PEG$^{5k}$-α-CA$_4$-ε-VE$_4$ (FIG. 11).

Characterization of Telodendrimers. MALDI-MS and $^1$H NMR of Polymers.

The mass spectra of the polymers were collected on Bruker AutoFlex III MALDI TOF/TOF mass spectrometer (linear and positive mode) using R-cyano-4-hydroxycinnamic acid as a matrix and DMSO as solvents, DMSO was removed by lyophilization.

1H NMR spectra of the polymers were recorded on a 600 MHz Bruker AVANCE III Nuclear Magnetic Resonance Spectrometer using DMSO-d$_6$ or CDCl$_3$ as solvents. The solvent residual peak was used as reference (DMSO-d$_6$: 2.49 ppm).

Size and CMC of Polymers.

The size and size distribution of the blank micelles were measured by dynamic light scattering (DLS) instruments (Zetatrac, Microtrac Inc.). The micelle concentrations were kept at 5.0 mg/mL for DLS measurements. All measurements were performed at 25° C., and data were analyzed by Microtrac FLEX Software 10.6.0. The critical micelle concentration (CMC) of the polymer micelles was measured through fluorescence spectrometry using pyrene as a hydrophobic fluorescent probe. Briefly, micelles were serially diluted in water to give the concentrations ranging from 50 ng/mL to 1 mg/mL. The stock solution of pyrene in methanol was added into the micelle solution to make a final concentration of pyrene of 2×10$^{-6}$ M. The solution was mildly shaken over night. Emission spectra were recorded ranging from 360 to 400 nm with a fixed excitation at 336 nm. The ratios of the intensity at 384 to 373 nm from the emission spectra of pyrene were plotted against the concentration of the micelles. The CMC was determined from the threshold concentration, where the intensity ratio I384/I373 begins to increase markedly.

Preparation of Drug or Dye Loaded Micelles.

Hydrophobic drugs, Gambogic acid (GA), Oridonin (ORD), Norcantharidin (NCTD) and PTX etc. were loaded into the micelles respectively by the solvent evaporation method as described in our previous studies[1]. Briefly, milligrams of drug and polymer molecules with the given weight ratios were first dissolved in chloroform in a 5.0 mL round bottom flask. The chloroform was rotaevaporated under vacuum to form a thin film, which was further dried under mechanical vacuum pump. PBS buffer (1 mL) was added to re-hydrate the thin film, followed by 5.0 min of sonication. Hydrophobic dye (Did) and GA were loaded into the micelles using the same strategy with a ratio of 10:1:0.5 (polymer:drug:dye, w/w). The size of drug or dye loaded micelles was measured by DLS.

DOX-loaded micelles were prepared, respectively, via a dry-down (evaporation) method as described briefly as following: DOX.HCl was stirred with 3 molar equivalent of triethylamine in chloroform (CHCl$_3$)/methanol (MeOH) (1:1, v/v) overnight to remove HCl from DOX.HCl. 10 mg telodendrimer was dissolved into the solution with different amount of neutralized DOX in CHCl$_3$/MeOH. Organic solvent was evaporated on rotavapor to obtain a homogeneous dry film. The film was reconstituted in 1 mL phosphate buffered solution (PBS), followed by sonication for 30 min, allowing the sample film to disperse into micelle solution.

Release Study.

GA loaded into PEG$^{5k}$-CA$_4$-L-VE$_4$ and PEG$^{5k}$-CA$_4$-L$_4$-VE$_4$ and ORD loaded into PEG$^{5k}$-CA$_4$-L-VE$_4$, PEG$^{5k}$-CA$_4$-L$_2$-VE$_4$ and PEG$^{5k}$-CA$_4$-L$_4$-VE$_4$, was prepared to determine the in vitro release profile. The GA loading for PEG$^{5k}$-CA$_4$-L-VE$_4$ and PEG$^{5k}$-CA$_4$-L$_4$-VE$_4$ were 30%, 30% (w/w, GA/micelle) and the ORD loading for PEG$^{5k}$-CA$_4$-L-VE$_4$, PEG$^{5k}$-CA$_4$-L$_2$-VE$_4$ and PEG$^{5k}$-CA$_4$-L$_4$-VE$_4$ were 10%, 10%, 10% (w/w, ORD/micelle) in the presence of total 10 mg polymers. Aliquots of drug-loaded micelle solution were injected into dialysis cartridges (Pierce Chemical Inc.) with a 3.5 kDa MWCO. The cartridges were dialyzed against 4L water at room temperature. The release medium was stirred at a speed of 100 rpm. The concentration of drug remaining in the dialysis cartridge at various time points was measured by UV-Vis (DOX, GA), fluorescence (SN-38) or by HPLC (ORD). The release medium was replaced with fresh medium at each 2 hours during the first 10 hours and then each 8 hours. Accumulated drug release was reported as the means for each triplicate sample.

Hemolysis Study.

Fresh citrated blood was obtained from healthy human volunteers. 2 mL of blood was added into 10 mL of PBS, and then red blood cells (RBCs) were separated from plasma by centrifugation at 1000×g for 10 min. The RBCs were washed three times with 10 mL of PBS solution, and resuspended in 20 mL PBS. 200 μL of diluted RBC suspension was mixed with polymers (PEG$^{5k}$-CA$_4$-L-VE$_4$, PEG$^{5k}$-α-CA$_4$-ε-VE$_4$, PEG$^{5k}$-α-VE$_4$-ε-CA$_4$ and PEG$^{5k}$-VE$_8$ respectively) at a series of concentrations (20, 100 and 1000 ug/mL) by gentle vortex and incubated at 37° C. After 0.5 h, 4 h and overnight, the mixtures were centrifuged at 1000×g for 5 min. Free hemoglobin in the supernatant was measured by the absorbance at 540 nm RBCs incubation with Triton-100 (2%) and PBS were used as the positive and negative controls, respectively. The percent hemolysis of RBCs was calculated using the following formula.

$$RBCs \text{ Hemolysis} = \frac{OD \text{ sample} - OD \text{ negative control}}{OD \text{ positive control} - OD \text{ negative control}} \times 100\%$$

Cell Culture and Cell Viability Assays.

T-cell lymphoma cell lines (Jurkat and MOLT-4) and B-cell lymphoma cell lines (Raji and Ramos) were purchased from American Type Culture Collection (ATCC; Manassas, Va., USA) and cultured in ATCC-formulated RPMI-1640 medium supplemented with 10% fetal bovine serum (FBS), 100 U/mL penicillin G, and 100 μg/mL streptomycin at 37° C. using a humidified 5% CO$_2$ incubator. MCF-7 and MCF-7 X-100 breast cancer resistant cell line and colon cancer cell line HT-29 were purchased from American Type Culture Collection (ATCC; Manassas, Va., USA) and were cultured in McCoy's 5A medium supplemented with 10% fetal bovine serum (FBS), 100 U/mL penicillin G, and 100 μg/mL streptomycin at 37° C. using a humidified 5% CO$_2$ incubator. Cancer cells were seeded in 96-well plates at a density of 10,000 cells/well 24 hrs prior to the treatment. Empty micelles and various formulations of chemodrugs with different dilutions were added to the plate and then incubated in a humidified 37° C., 5% CO$_2$ incubator. After 72 hr incubation, CellTiter 96® Aqueous Cell Proliferation Reagent, which is composed of MTS and an electron coupling reagent PMS, was added to each well according to the manufacturer's instructions. The cell viability was determined by measuring the absorbance at 490 nm using a microplate reader (SpectraMax M2, Molecular Devices, USA). Untreated cells served as a control. Results were shown as the average cell viability [(OD$_{treat}$−OD$_{blank}$)/(OD$_{control}$−OD$_{blank}$)×100%] of triplicate wells.

Animals and Tumor Models.

Female athymic nude mice (Nu/Nu strain), 6-8 weeks age, were purchased from Harlan. All animals were kept under pathogen-free conditions according to AAALAC (Association for Assessment and Accreditation of Laboratory Animal Care) guidelines and were allowed to acclimatize for at least 4 days prior to any experiments. All animal experiments were performed in compliance with institutional guidelines and according to protocol approved by the Committee for the Humane Use of Animals of State University of New York Upstate Medical University. Subcutaneous tumor xenograft mouse models were established by injecting 1×10$^7$ HT-29 or raji cancer cells in a 100 μL of mixture of PBS and Matrigel (1:1 v/v) subcutaneously at the right flank in female nude mice.

Biodistribution and Animal Imaging.

Nude mice with subcutaneous tumors of an approximate 8 to 10 mm in diameter were subjected to in vivo NIRF optical imaging. At different time points post-injection of DiD and chemodrug (PTX or DOX or GA) co-loaded micelles (the mass ratio of DiD and PTX within nanocarrier was 0.25:1:10), mice were scanned using a IVIS-200 small animal imager at cy5.5 excitation and emission channels. The mice were anaesthetized by isofluorane gas before and during each imaging. After in vivo imaging, animals were euthanized by CO$_2$ overdose after the last in vivo imaging. Tumors and major organs were excised and imaged with the IVIS-200 small animal imager.

In Vivo Cancer Treatment.

Subcutaneous Raji lymphoma xenograft mouse model was used to evaluate the therapeutic efficacy of different formulations of DOX. When tumor volume reached 150-300 mm$^3$, mice were intravenously administrated with PBS, DOX.HCl, Doxil®, DOX-PEG$^{5k}$-CA$_4$-L-Rh$_4$ at the dose of 10 mg/kg DOX equivalent (MTD of free DOX), respectively (n=5-8). The treatment was given every four days on days 0, 4 and 8 for a total of three doses. Tumor sizes were measured with a digital caliper twice per week. Tumor volume was calculated by the formula (L×W$^2$)/2, where L is the longest, and W is the shortest in tumor diameters (mm). To compare between groups, relative tumor volume (RTV) was calculated at each measurement time point (where RTV equals the tumor volume at given time point divided by the tumor volume prior to initial treatment). For humane reasons, animals were sacrificed when the implanted tumor volume reached 2000 mm$^3$, which was considered as the end point of survival data. At day 7 after the last dosage, blood samples were obtained from all the mice for the measurement of blood cell counts, hepatic or renal function tests (ALT, AST, and BUN), and serum enzyme markers of cardiotoxicity including creatine kinase (CK) and lactate dehydrogenase (LDH).

The level of significance in all statistical analyses was set at a probability of P<0.05. Data are presented as means±standard error (SEM). Statistical analysis was performed by Student's t-test for comparison of two groups, and one-way analysis of variance (ANOVA) for multiple groups, followed by Newman-Keuls test if overall P<0.05.

Results and Discussion.

Figure 4:
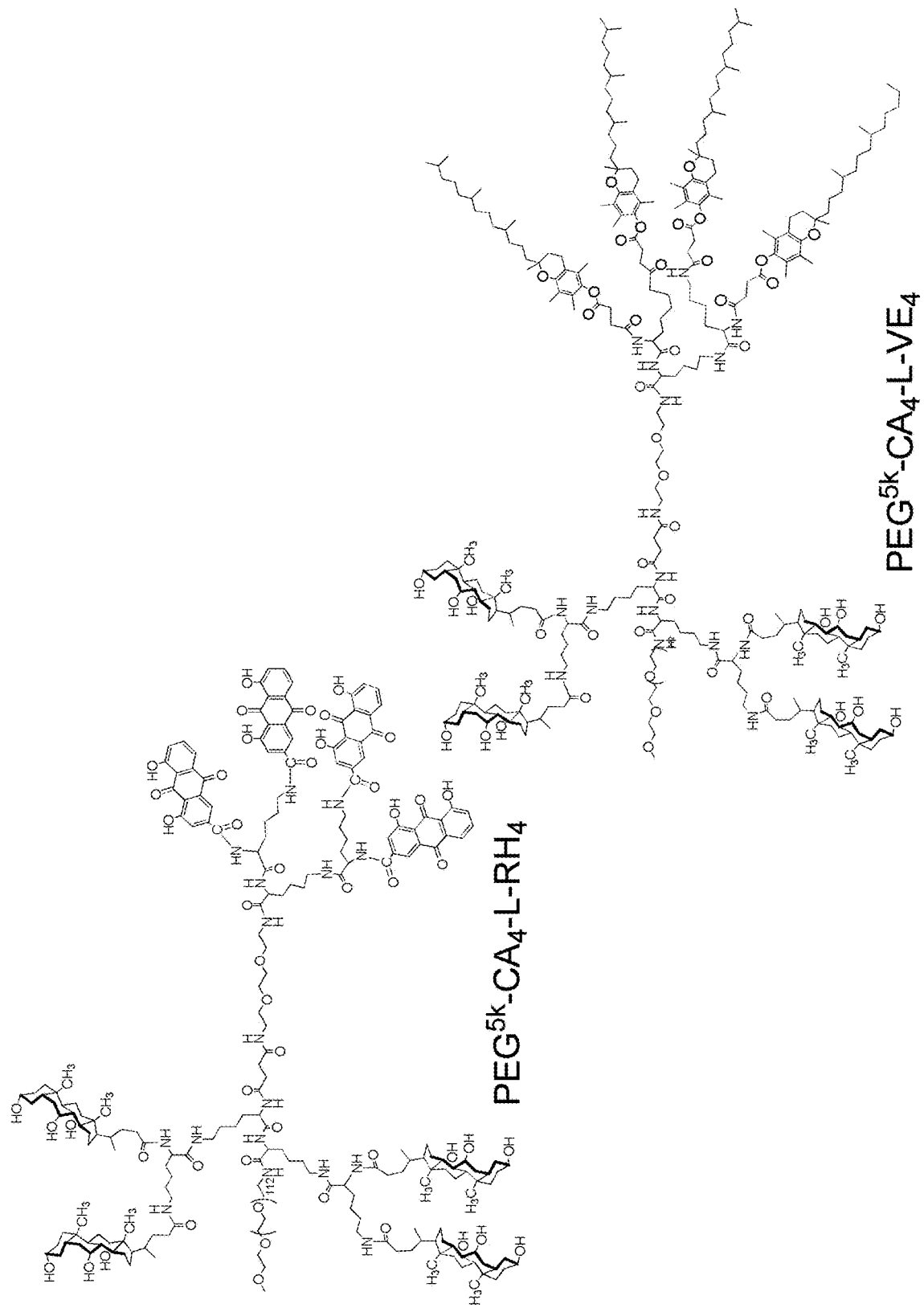
FIG. 4. Chemical structures of examples of trilayered telodendrimers with rehein and vitamin E as building blocks.
Figure 4:
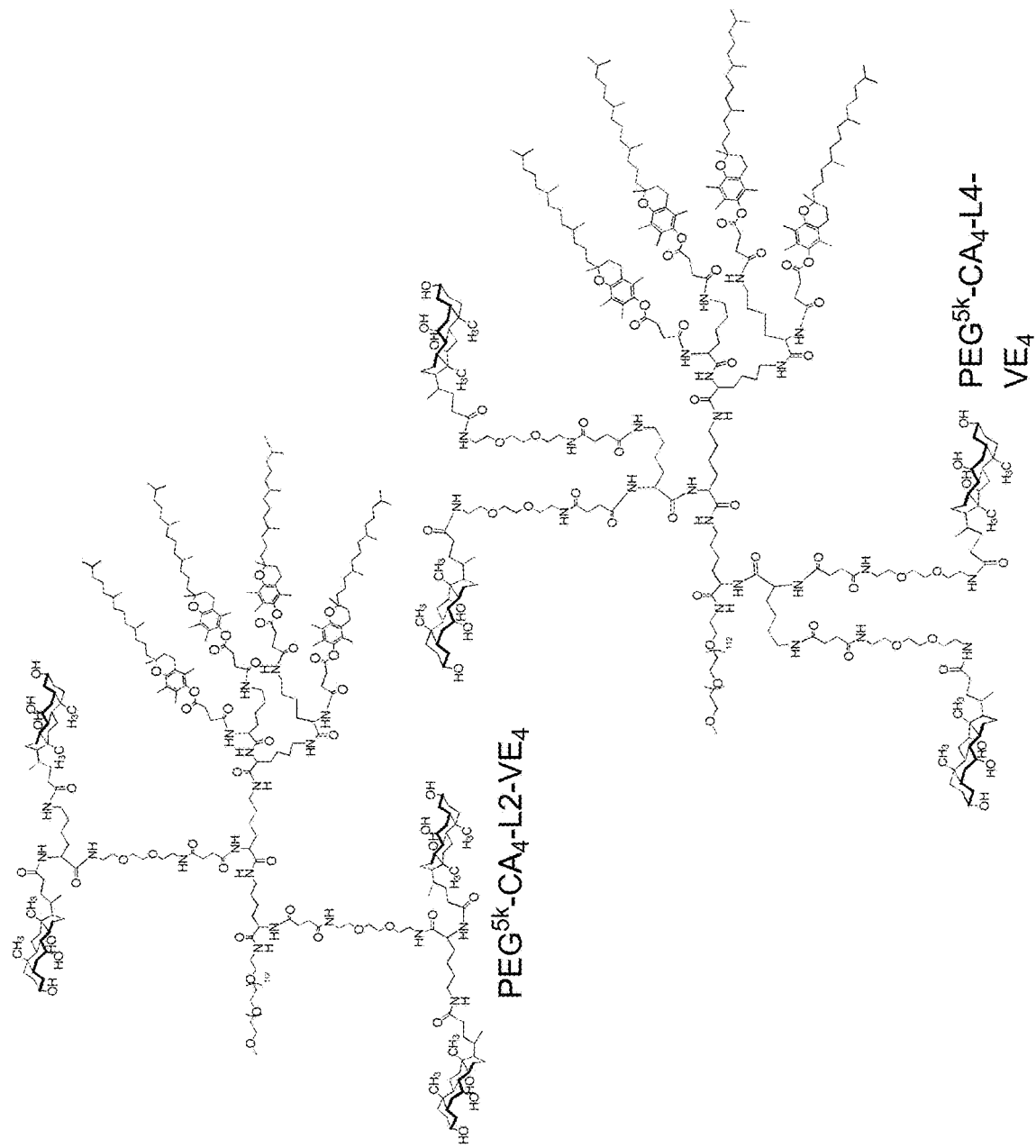
Figure 5:
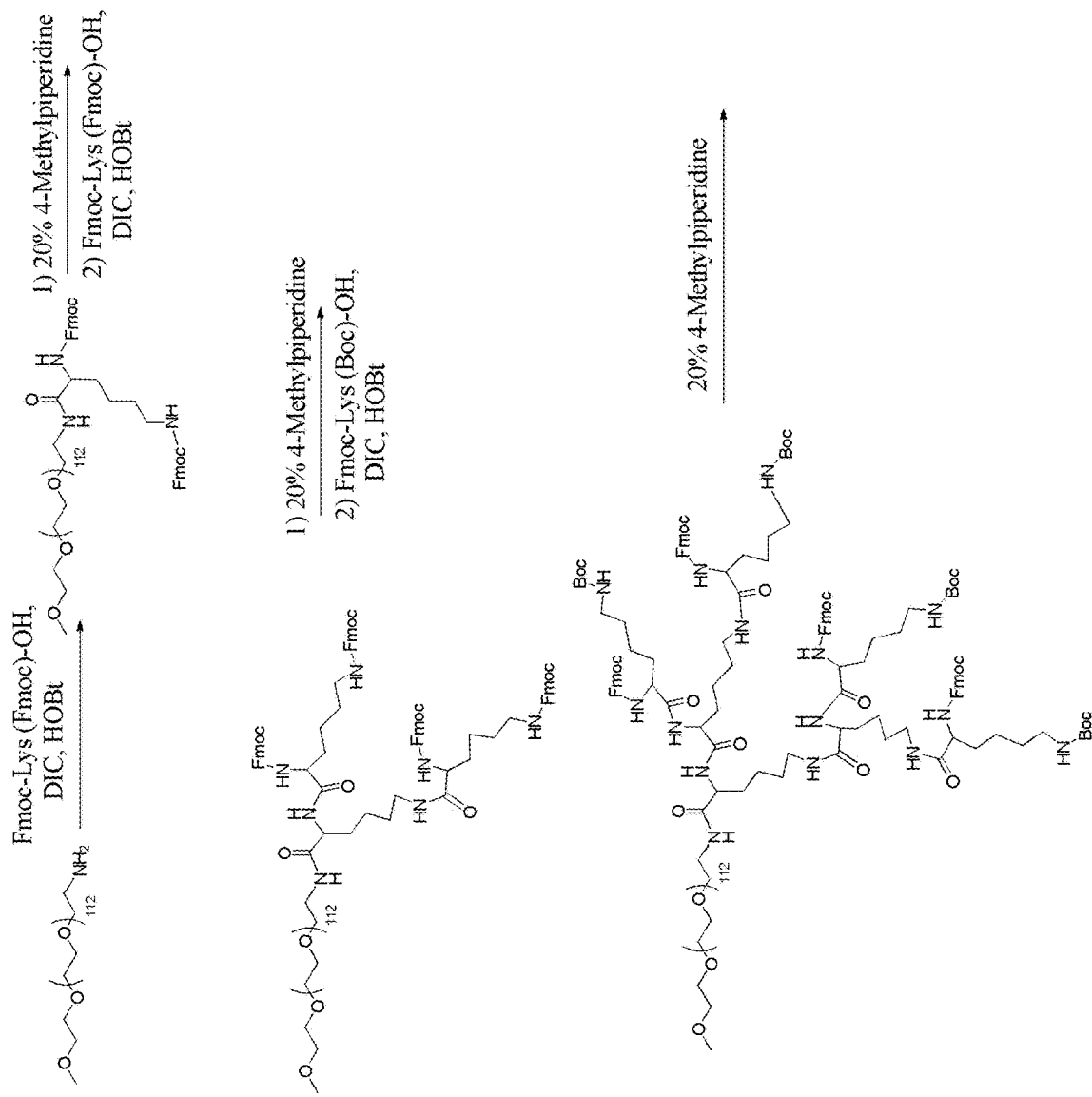
FIG. 5. Example of a synthetic route for hybrid telodendrimers with CA and VE conjugated on the different animal groups in the matrix polylysine, e.g., $PEG^{5k}\text{-}\alpha\text{-}CA_4\text{-}\varepsilon\text{-}VE_4$ and $PEG^{5k}\text{-}\alpha\text{-}VE_4\text{-}\varepsilon\text{-}CA_4$ FIG. 6. Chemical structure of examples of hybrid telodendrimers with CA and rhein conjugated on the different amino groups in the polylysine, e.g., $PEG^{5k}\text{-}\alpha\text{-}CA_4\text{-}\varepsilon\text{-}Rh_4$ and $PEG^{5k}\text{-}\alpha\text{-}Rh_4\text{-}\varepsilon\text{-}CA_4$ FIG. 7. Example of a synthetic route for a two layered telodendrimers containing D-α-tocopherol succinate, e.g., $PEG^{5k}\text{-}VE_8$ and rhein molecules, e.g., $PEG^{5k}\text{-}RH_8$.
Figure 5:
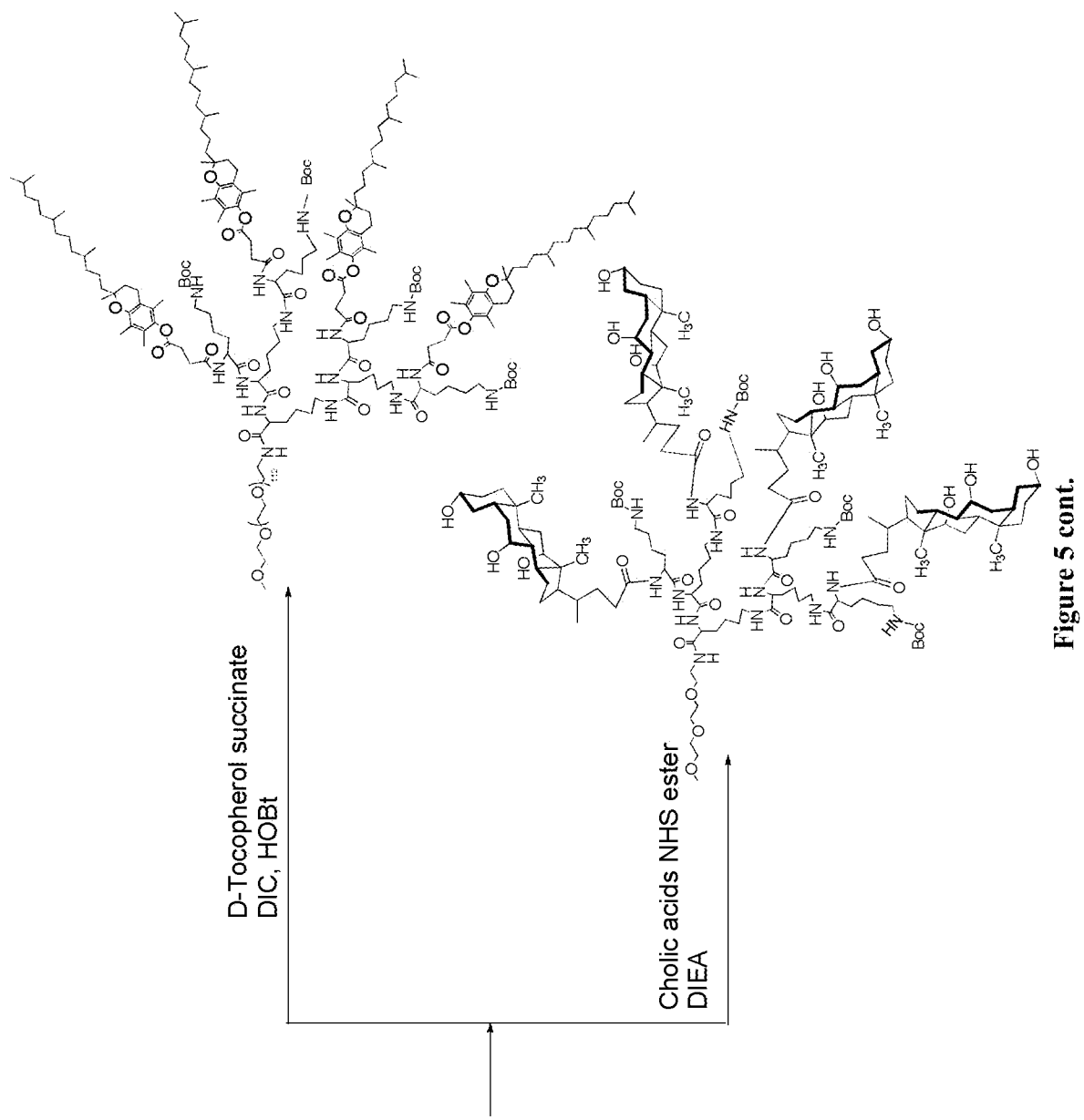
Figure 5:
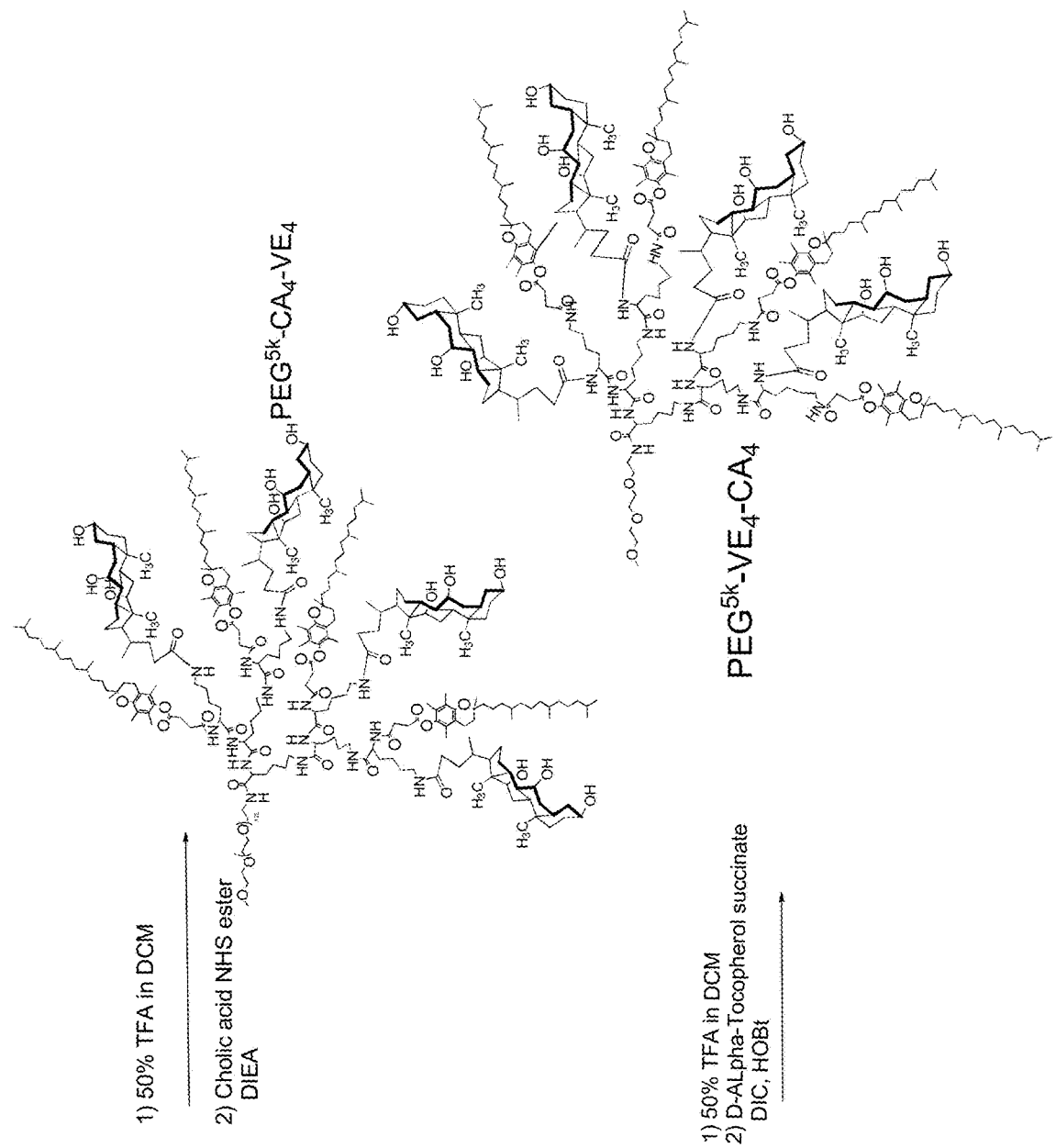

Functional segregated telodendrimer containing Vitamin E for TCM drug delivery. As shown from FIGS. 2-7, the telodendrimers were prepared via liquid phase peptide chemistry using HOBt/DIC as condensation reagents. Orthogonal protected amino acids, e.g., Fmoc-Lys-Fmoc-OH, Fmoc-Lys-Boc-OH and Boc-Lys-Boc-OH, have been used for the construction of telodendrimers with various architectures. A triethylene glycol diamine derived linker molecule (PEG linker) is used to tune the sterohindrance of the telodendrimer. As shown in FIG. 4, three-layered functional-segregated telodendrimers were prepared with numbers of linker molecules and affinity building blocks. Also synthesized were telodendrimers using other bioactive molecules, such as various vitamins, natural lipids, bioactive molecules isolated from traditional Chinese medicine, specifically including α-tocopherol, riboflavin, rhein, curcumin, coumarin, folic acid, isoflavine, cholic acid, cholesterol, polylysine, cis-aconitic anhydride, ascorbic acid, biotin, protoporphyrin, chlorine, quercetin, catechin etc. As examples, Vitamin E and rhein molecules and coumarin were introduced in the interior layer of the telodendrimer to increase the affinity specifically to nonaromatic or aromatic drugs, such as paclitaxel, docetaxel, VP-16, doxorubicin, daunorubicin, SN-38, gambogic acid, triptolide, oridonin and norcatharidin etc., respectively.

In addition to three layered functional segregated telodendrimers, a series of telodendrimers with cholic acid and functional groups, such as rhein and Vitamin E and coumarin, conjugated alternatively on the peripheral amino groups on the dendritic polylysine, respectively were also synthesized (shown in FIG. 11, 12). In addition, eight functional groups, such as rhein and vitamin e and coumarin, were introduced on to the peripheral of oligo polylysine to serve as core-forming building blocks (shown in FIG. 7). As expected the telodendrimer without cholic acid, e.g., PEG$^{5k}$Rh$_8$ and PEG$^{5k}$VE$_8$ form big aggregates in aqueous solution and precipitate, which is not suitable for drug delivery. It showed that cholic acid as a building block was critical in stabilizing micelle structures. This is due to the facial amphiphilic feature of cholic acid, which can minimize the energy at the interface of the hydrophobic core and hydrated shell structure and thereby prevent further aggregation. Therefore, in the following telodendrimer synthesis, cholic acid generally serves as a stabilizing component to shelter the functional layer. However as a exception, PEG$^{5k}$CO$_8$ with eight coumarins as the sole core forming building block has good solubility in water with monodispersed particle sizes (24.7±6.5 nm) and is able to encapsulate SN-38 efficiently with mono-dispersed particle sizes (34.8±11 nm) and good stability. This may due to the smaller size of coumarin and the high binding affinity with drug molecules.

TABLE 1

Characterization of the polymers. The mono-dispersed mass traces were detected for the polymers, and the molecular weights of the polymers from MALDI-TOF/TOF MS (FIG. 12) were almost identical to the theoretical value. The number of cholic acids and D-α-tocopherol succinate determined by $^1$H NMR for the polymers was consistent with the molecular formula of the target polymers.

| Polymers | Mw (Theo.)[a] | Mw (MS)[b] | R$_{CA/VE(RH)}$[c] (NMR) | Size (nm)[d] | CMC (μg/mL)[e] |
|---|---|---|---|---|---|
| PEG$^{5k}$-CA$_4$-L-VE$_4$ | 9470 | 9630 | 0.82 | 25 ± 6 | 3.2 |
| PEG$^{5k}$-CA$_4$-L$_2$-VE$_4$ | 10000 | 8270 | 1.06 | 20 ± 4 | 5.2 |

TABLE 1-continued

Characterization of the polymers. The mono-dispersed mass traces were detected for the polymers, and the molecular weights of the polymers from MALDI-TOF/TOF MS (FIG. 12) were almost identical to the theoretical value. The number of cholic acids and D-α-tocopherol succinate determined by $^1$H NMR for the polymers was consistent with the molecular formula of the target polymers.

| Polymers | Mw (Theo.)[a] | Mw (MS)[b] | R$_{CA/VE(RH)}$[c] (NMR) | Size (nm)[d] | CMC (μg/mL)[e] |
|---|---|---|---|---|---|
| PEG$^{5k}$-CA$_4$-L$_4$-VE$_4$ | 10500 | 9426 | 0.95 | 17 ± 3 | 3.8 |
| PEG$^{5k}$-VE$_8$ | 10100 | 9961 | 7.6[f] | multiple | 6.7 |
| PEG$^{5k}$-α-VE$_4$-ε-CA$_4$ | 9500 | 8097 | 0.88 | multiple | 1.1 |
| PEG$^{5k}$-α-CA$_4$-ε-VE$_4$ | 9500 | 9415 | 0.80 | multiple | 2.6 |
| PEG$^{5k}$-CA$_4$-L-RH$_4$ | 8784 | 8215 | — | 24 ± 5 | — |
| PEG$^{k}$-α-CA$_4$-ε-RH$_4$ | 8550 | 8368 | — | 6.8 ± 3.2 | — |

Note:
[a]Theoretical molecular weight.
[b]Obtained via MALDI-TOF/TOF MS analysis (linear positive mode);
[c]Ratio with number of cholic acids to D-α-tocopherol succinate (Ve), number of cholic acids was calculated based on the average integration of the peaks of methyl proton 18 in cholic acid at 0.54 ppm and methoxyl proton of PEG at 3.32 ppm in $^1$H NMR spectra in DMSO-d$_6$. Number of D-α-tocopherol succinate (Ve) was calculated based on the average integration of the peaks of the methyl proton of D-α-tocopherol succinate (1.95 ppm) and methoxyl proton of PEG at 3.32 ppm in $^1$H NMR spectra in DMSO-d$_6$;
[d]Measured by dynamic light scattering (DLS);
[e]Measured via fluorescent method by using pyrene as a probe;
[f]It showed the number of D-α-tocopherol succinate (Ve) in Polymer PEG$^{5k}$-Ve$_8$. Number of D-α-tocopherol succinate (Ve) was calculated based on the average integration ratio of the peaks of the methyl proton of D-α-tocopherol succinate (1.95 ppm) and methoxyl proton of PEG at 3.36 ppm in $^1$H NMR spectra in CDCl$_3$.

TABLE 2

Size of the drug or dye loaded polymers by DLS

| Size (nm) Polymers | Gambogic acid (GA) | Oridonin (ORD) | Norcantharidin (NCTD) | Triptolide (TPL) | Paclitaxel (PTX) | VP 16 |
|---|---|---|---|---|---|---|
| PEG$^{5k}$-CA$_4$-L-VE$_4$ | 29 ± 9 (5:1.5 w/w) | 18 ± 5 (5:0.5 w/w) | 30 ± 11 (5:1.5 w/w) | 47 ± 12 (5:0.5 w/w) | 30 ± 9 (10:1 w/w) | 32 ± 4 nm (5:0.5 w/w) |
| PEG$^{5k}$-CA$_4$-L$_2$-VE$_4$ | — | 19 ± 6 (5:0.5 w/w) | 22 ± 6 (5:1.5 w/w) | 20 ± 6 (5:0.5 w/w) | — | 25 ± 2 nm (5:0.5 w/w) |
| PEG$^{5k}$-CA$_4$-L$_4$-VE$_4$ | 27 ± 8 (5:1.5 w/w) | 17 ± 5 (5:0.5 w/w) | 19 ± 5 (5:1.5 w/w) | — | 20 ± 8 (10:1 w/w) | 20 ± 3 nm (5:0.5 w/w) |
| PEG$^{5k}$CA$_8$ | | | | 11 ± 2 (5:1 w/w) | 24 nm (20:4 w/w) | |

Figure 12:
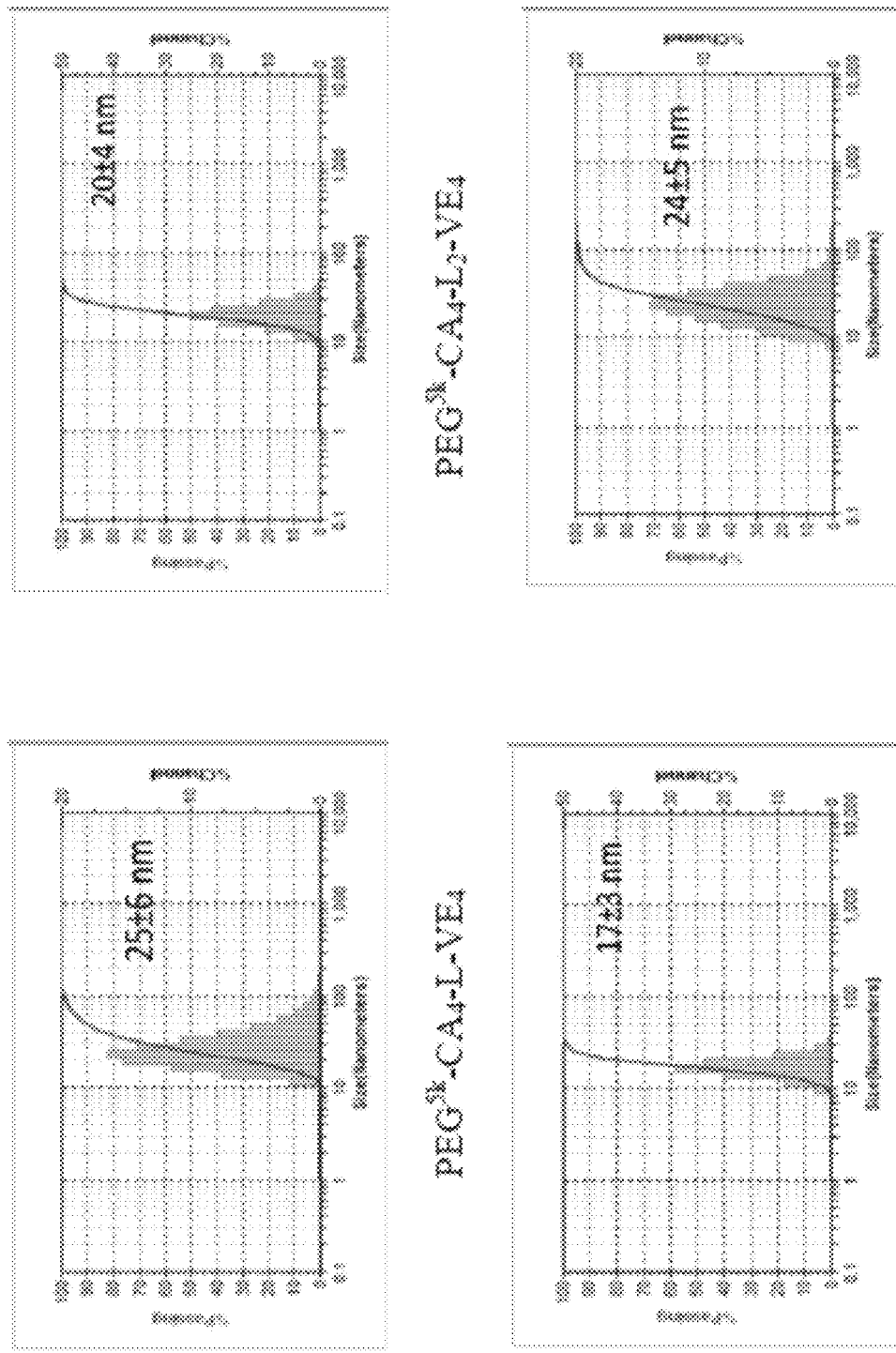
FIG. 12. Particle sizes of polymers, measured by dynamic light scattering (Zetatrac, Microtrac®).

As shown in Table 1, the molecular weights of the telodendrimers have been characterized via MALDI-ToF mass spectrometry to be very close to the theoretical values (FIGS. 8 & 9). Some variations may be due to the well-known discrimination in MALDI-TOF MS analysis on the high molecular weight molecules, especially for the highly entangled and self-assembled polymers. The numbers of the CA and the affinity building blocks have been detected by the proton NMR to be very close to the theoretical ratio (FIGS. 10 & 11). The NMR and MS study indicated the well-defined structures of these telodendrimers synthesized via peptide chemistry. The DLS particle size measurements revealed the monodispersed particle size about 20 to 30 nm for trilayered telodendrimer with VE ad affinity blocks (FIG. 12). However, the linear-dendritic two-layered telodendrimers with only VE or VE and CA in the interior layers showed multiple peaks in size distribution. However, the rhein-containing three layered or two-layered telodendrimers both showed stable particles sizes before and after doxorubicin loading.

Figure 13:
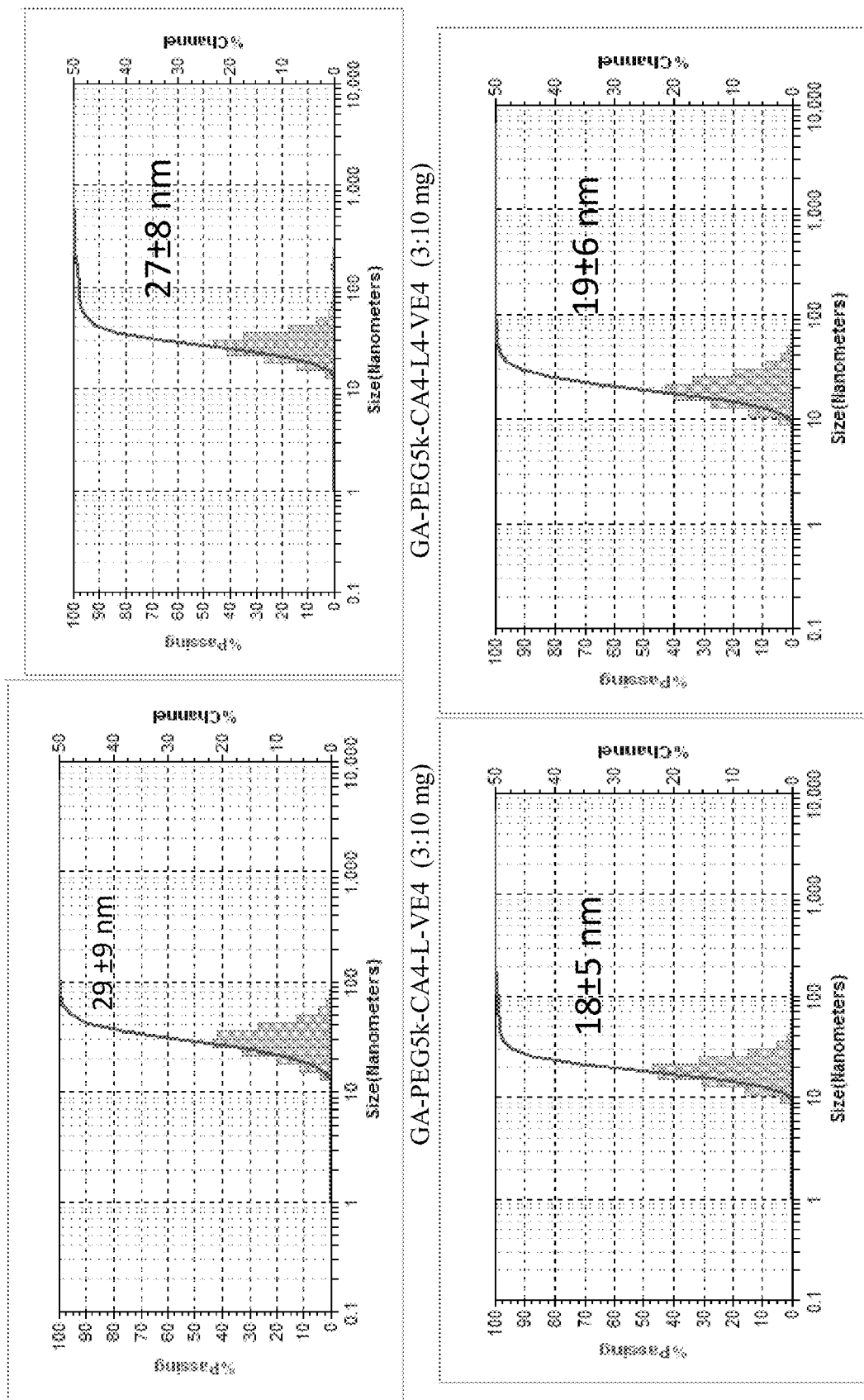
FIG. 13. Particle sizes of the drug loaded to trilayered telodendrimer micelles.
Figure 13:
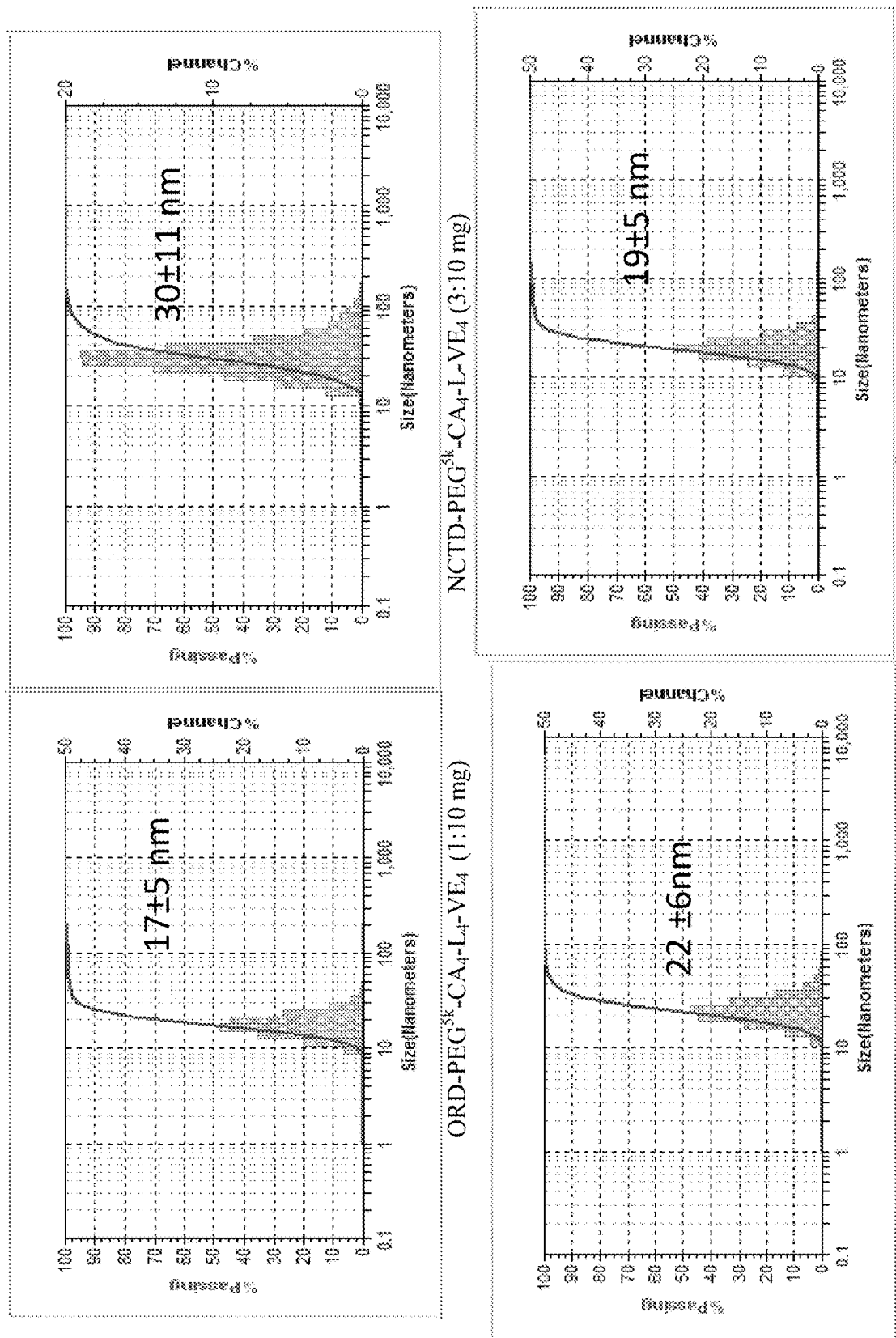
Figure 13:
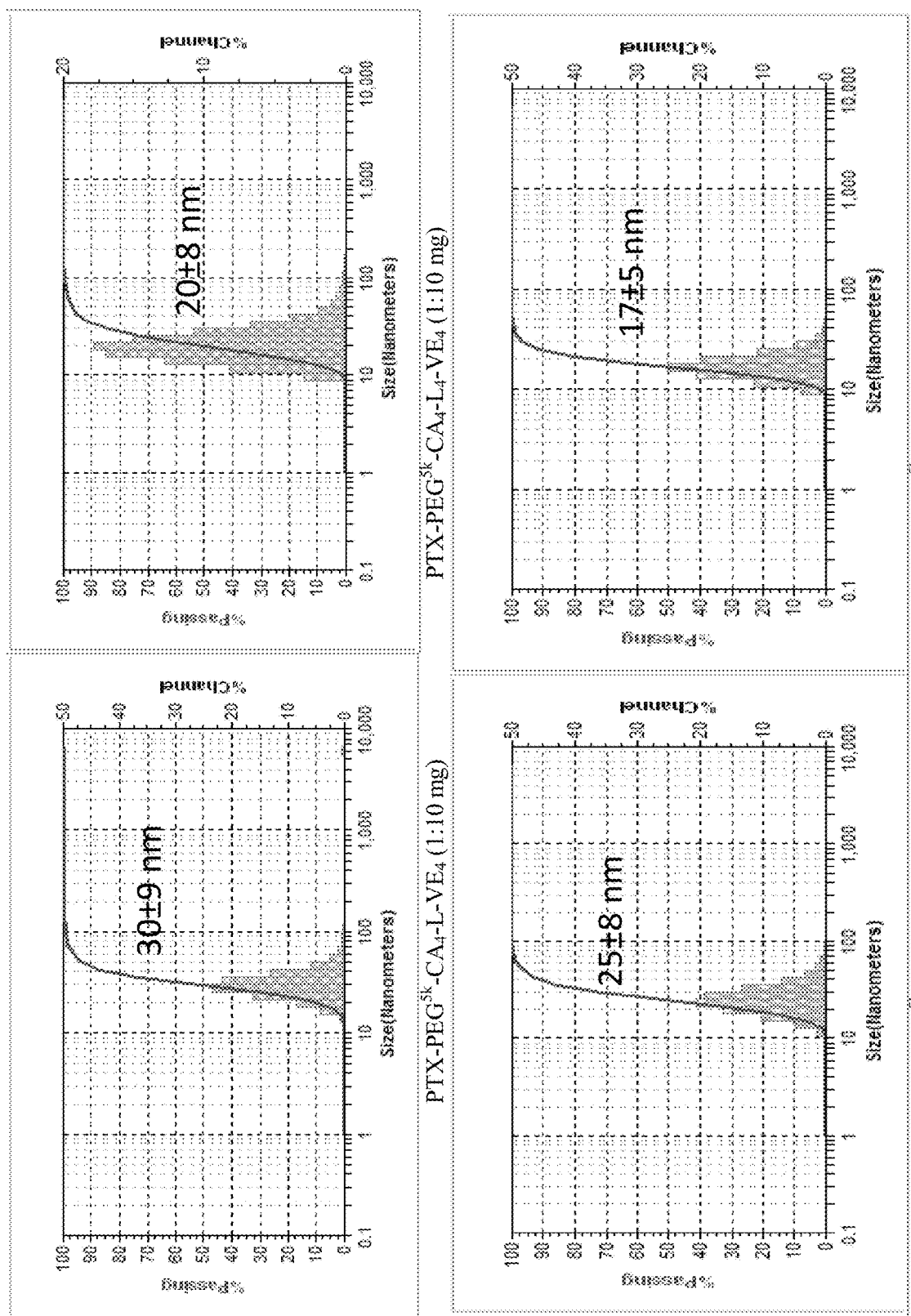
Figure 13:
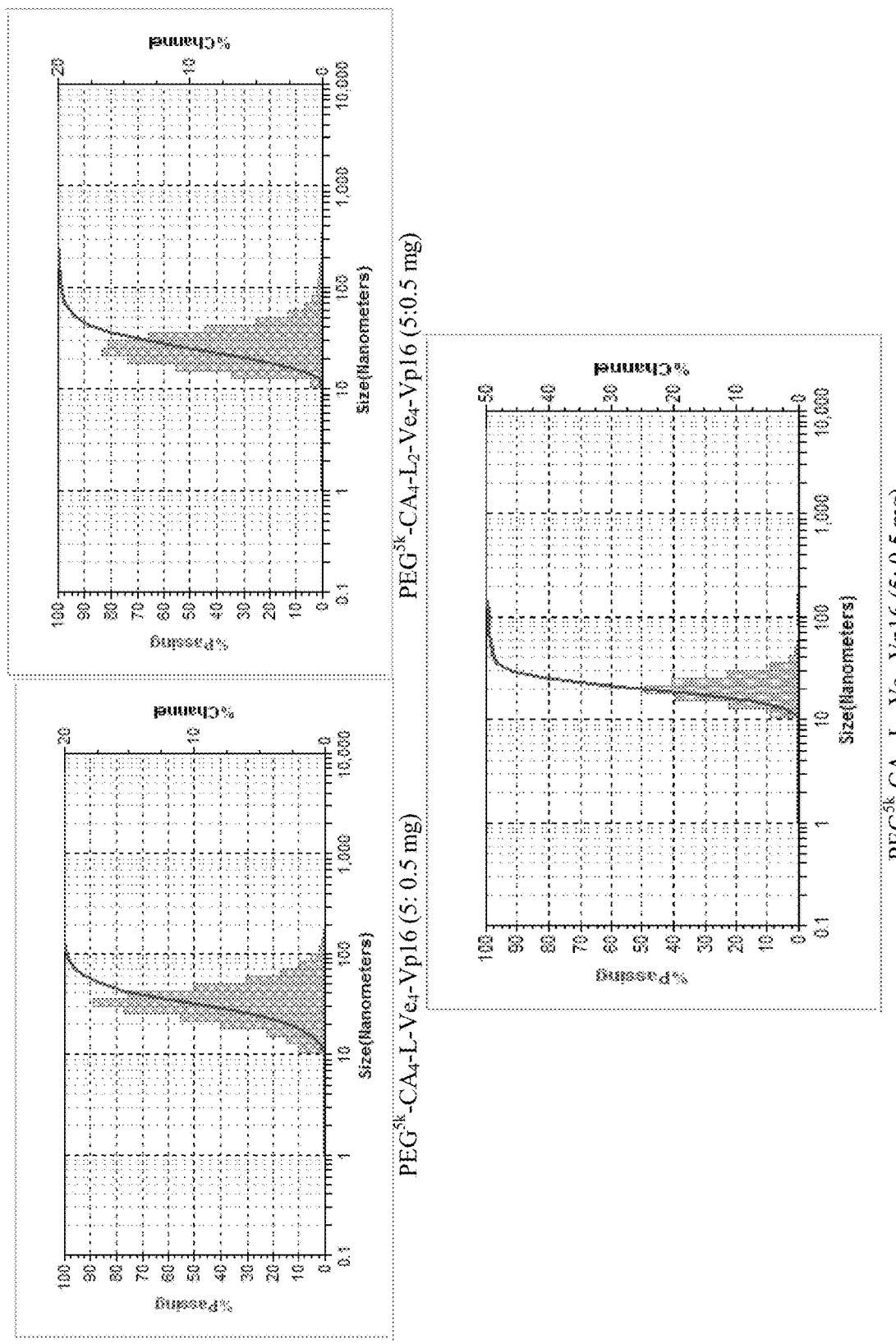

As shown in Table 2, trilayered telodendrimers possessing VE in the affinity layers are very versatile in loading various of anticancer drug molecules at high loading capacity from 10-30% percent, such as clinically used paclitaxel, VP16 and other potent anticancer molecules isolated from Traditional Chinese Medicine (TCM), e.g., gambogic acid, oridonin, norcantharidin and triptolide. In addition, docetaxel, SN-38 and curcumin can be loaded in these telodendrimer micelles efficiently. The drug loaded nanotherapeutics had narrow and mono-dispersed particle sizes with the mean values from 17 to 47 nm (FIG. 13) within the optimal ranges for in vivo tumor targeting.

Figure 14:
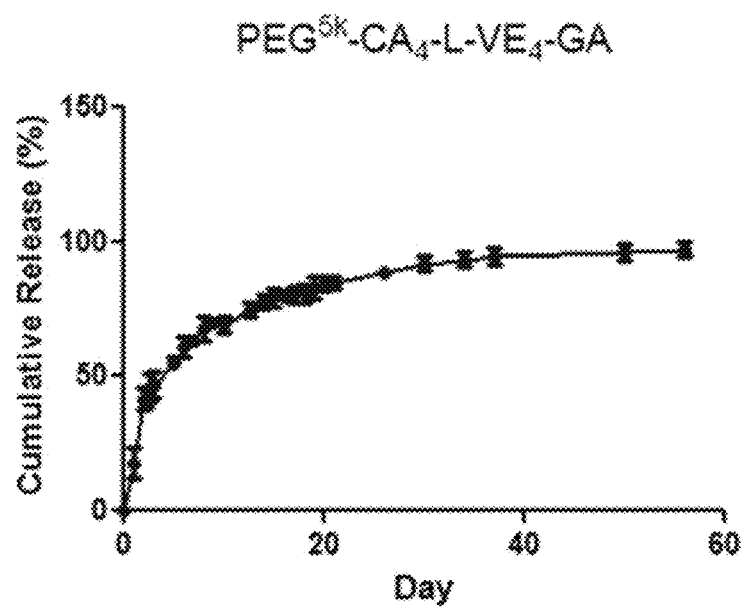
FIG. 14. Example of a profile of GA released from $PEG^{5k}\text{-}CA_4\text{-L-}VE_4\text{-GA}$ (10:3 mg, w/w).
Figure 15:
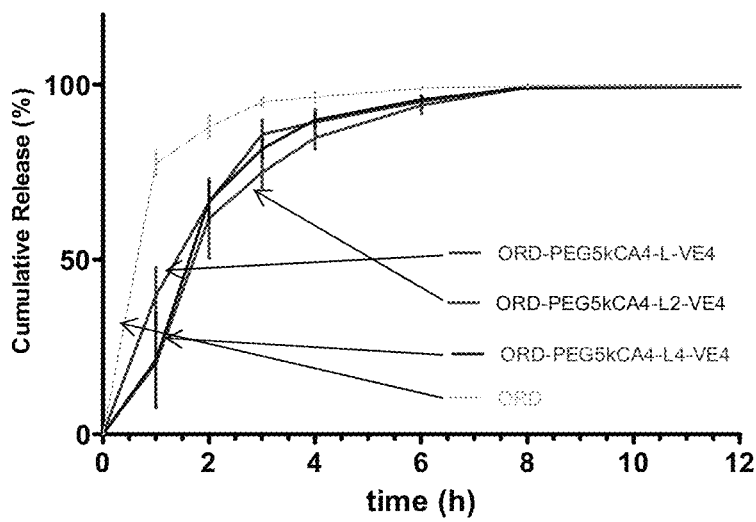
FIG. 15. Example of a profile of ORD released from micelles (polymer:ORD 10:3 mg, w/w).
Figure 16:
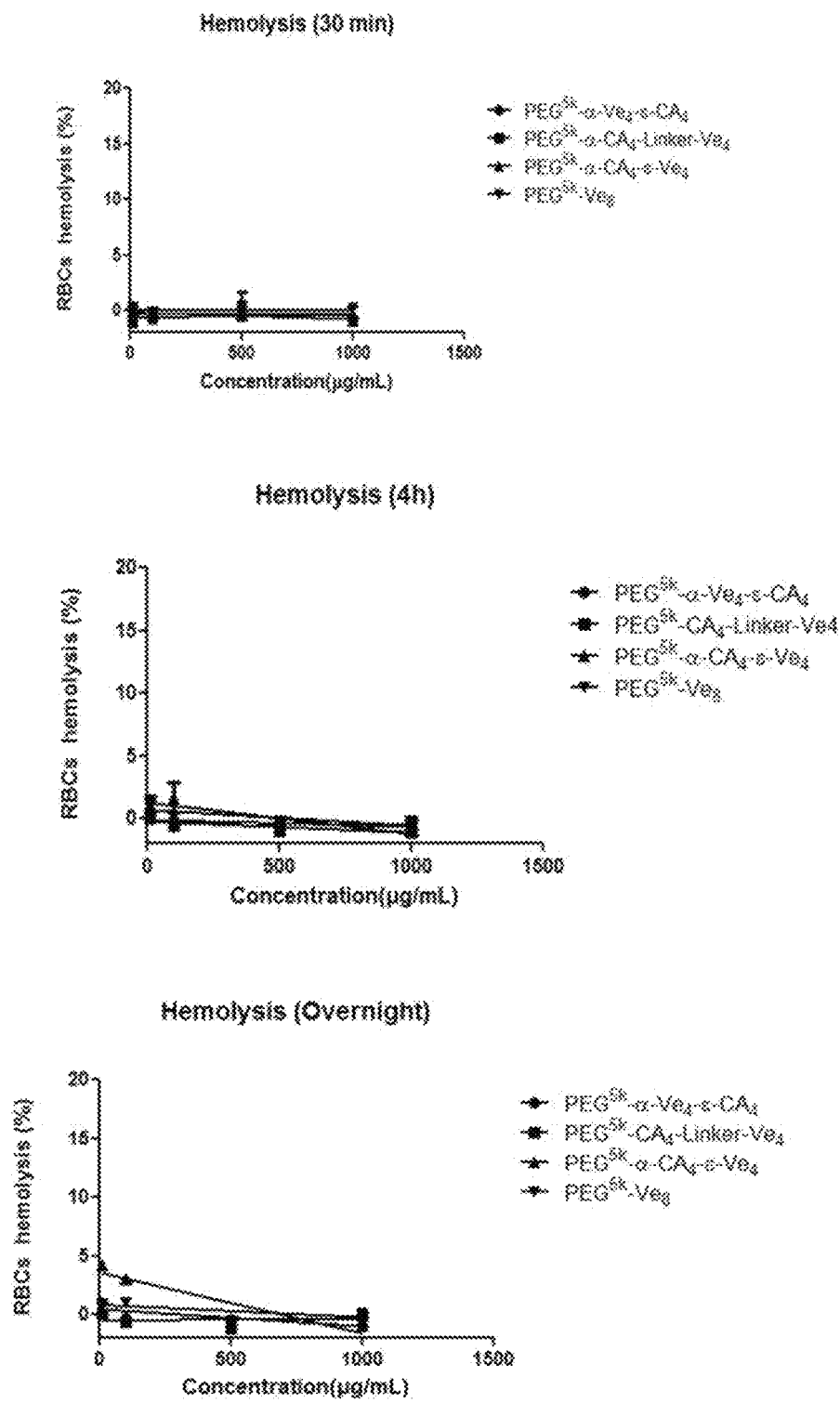
FIG. 16. Example of a hemolysis of trilayered telodendrimers containing VE.

As shown in FIG. 14, the release profile of gambogic acid from the PEG5kCA4-L-VE4 micelle is very slow with 50% drug released out by day 4 and 90% drug released out about day 20. On the contrary, oridonine release is very fast with 50% drug released at 1 hour and complete release within 8 hours, although slower than free drug with complete release at 3 hours (FIG. 15). The Vitamin E containing telodendrimer shows completely inert in the hemolysis assay (FIG. 16), indicating the safety profile for systemic administration.

Figure 17:
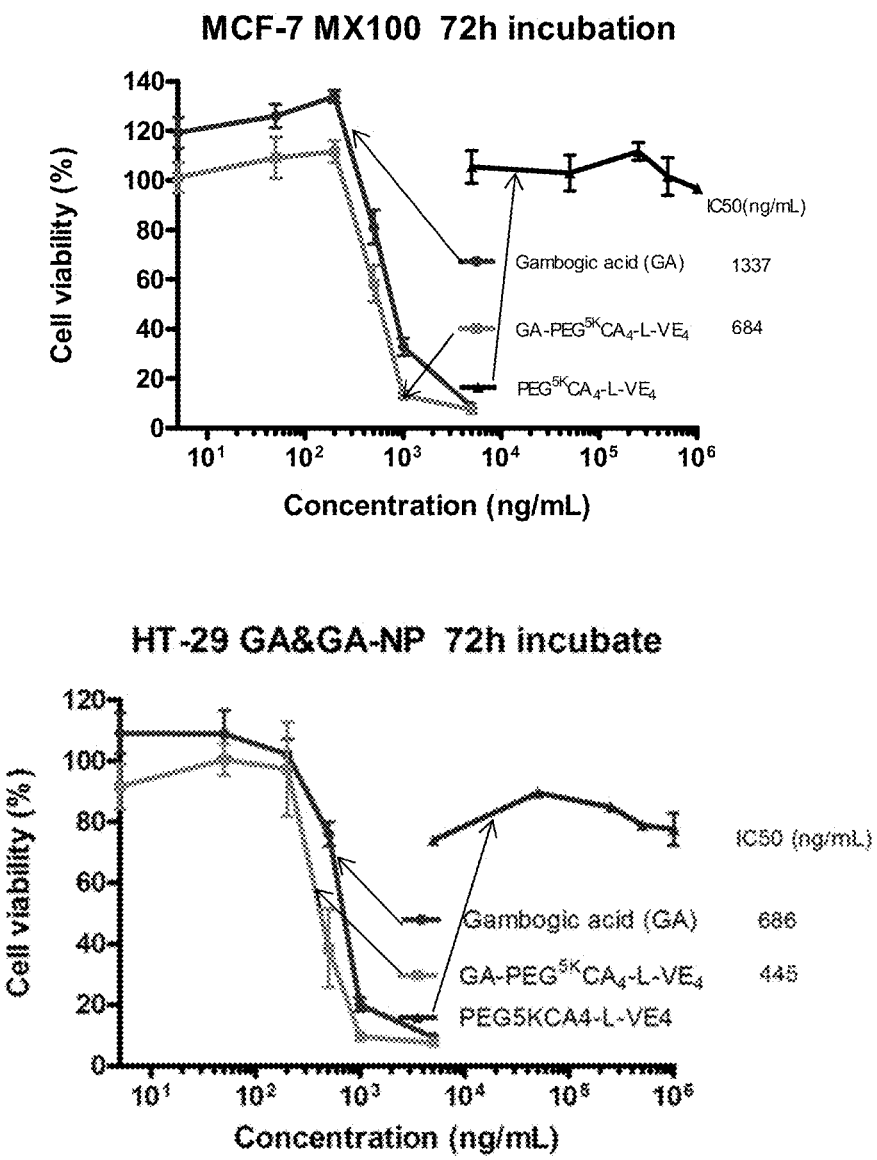
FIG. 17. Example of cytotoxicity of the $PEG^{5k}CA_4\text{-L-}VE_4$ and the gambogic acid loaded nanoparticle on MCF-7 MX100 breast cancer drug resistant cell line and the colon cancer cell line HT-29, respectively, in comparison with free gambogic acid (dissolved in DMSO).
Figure 18:
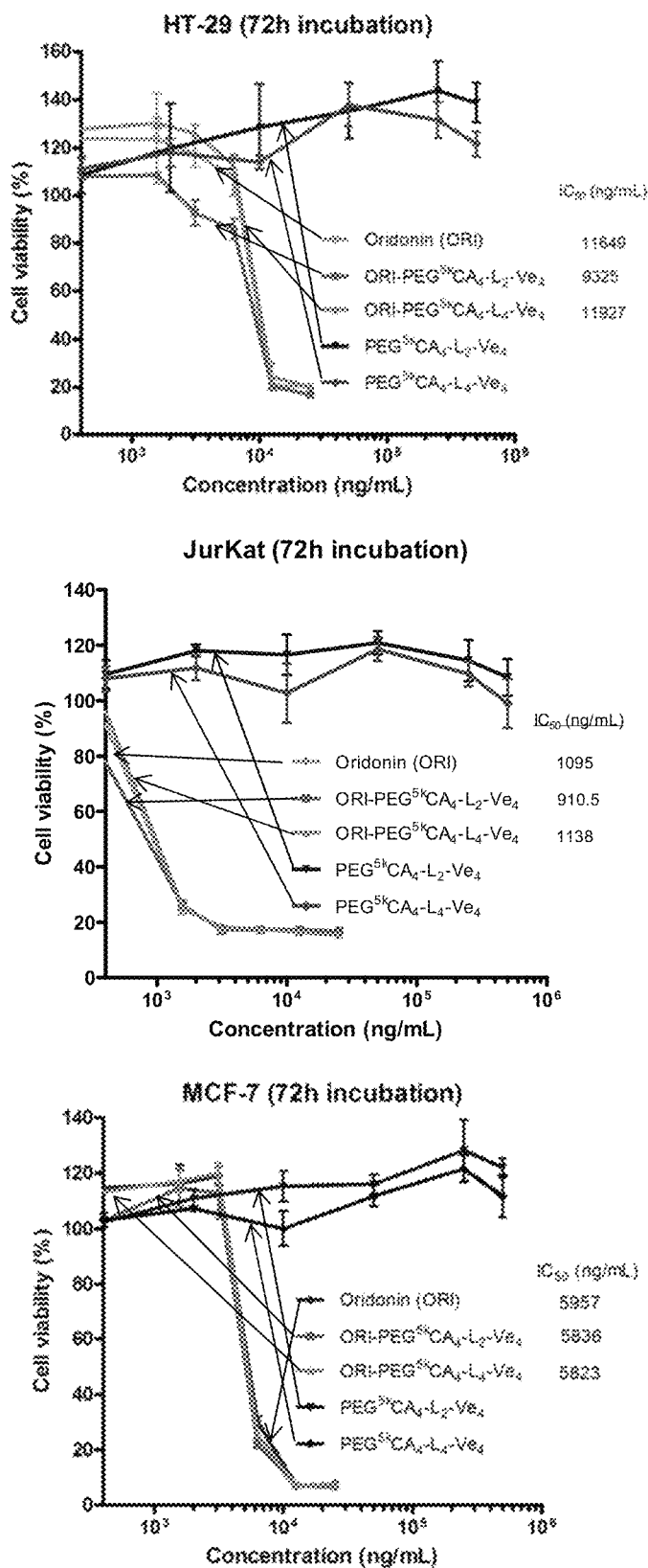
FIG. 18. Example of cytotoxicity of the $PEG^{5k}CA_4\text{-}L_2\text{-}VE_4$ and $PEG^{5k}CA_4\text{-}L_4\text{-}VE_4$ and the orindonian loaded nanoparticles on MCF-7 MX100 breast cancer drug resistant cell line, colon cancer cell line HT-29 and jurkat lymphoma cells, respectively, in comparison with free oridonian (dissolved in DMSO).

The cytotoxicity assay on various cell lines indicated that the trilayered telodendrimers with VE as building blocks are nonotoxic up to 1 mg/mL concentration (FIGS. 17 & 18). Gambogic acid is a natural product with cytotoxic activity against tumor cells in culture. It was identified as an active compound for activators of caspases, proteases involved in apoptosis. Gambogic acid has been identified as an antagonist of antiapoptotic Bcl-2 family proteins. Gambogic acid has also been studied to sensitize cancer cells to typical chemodrugs, such as Doxorubicin in ovarian cancer, docetaxel in gastrointestinal cells. As shown in FIG. 17, the encapsulation of gambogic acid in a $PEG^{5k}CA_4$-L-$VE_4$ nanocarrier reduced the IC50 compared with free drug on MCF-7 MX100 breast cancer drug resistant cell line and the colon cancer cell line HT-29, respectively. This may due to the increased cell uptake of the drug molecules as well as the increased drug stability and availability in cell culture.

Oridonin, an ent-kaurane diterpenoid isolated from *Rabdosia rubescens*, is an important traditional Chinese herbal remedy. Studies showed that oridonin induced apoptosis in a variety of cancer cells including prostate, breast, non-small cell lung cancer, acute leukemia, glioblastoma multiform and human melanoma cells and colorectal cancers. As shown FIG. 18, the empty $PEG^{5k}CA_4$-$L_2$-$VE_4$ and $PEG^{5k}CA_4$-$L_4$-$VE_4$ nanocarriers were nontoxic. The orindonian-loaded nanoparticles showed the similar IC50 compared with the free drug on drug resistant MCF-7 MX100 breast cancer cell line, HT-29 colon cancer cell line and jurkat lymphoma cells, respectively.

Figure 19:
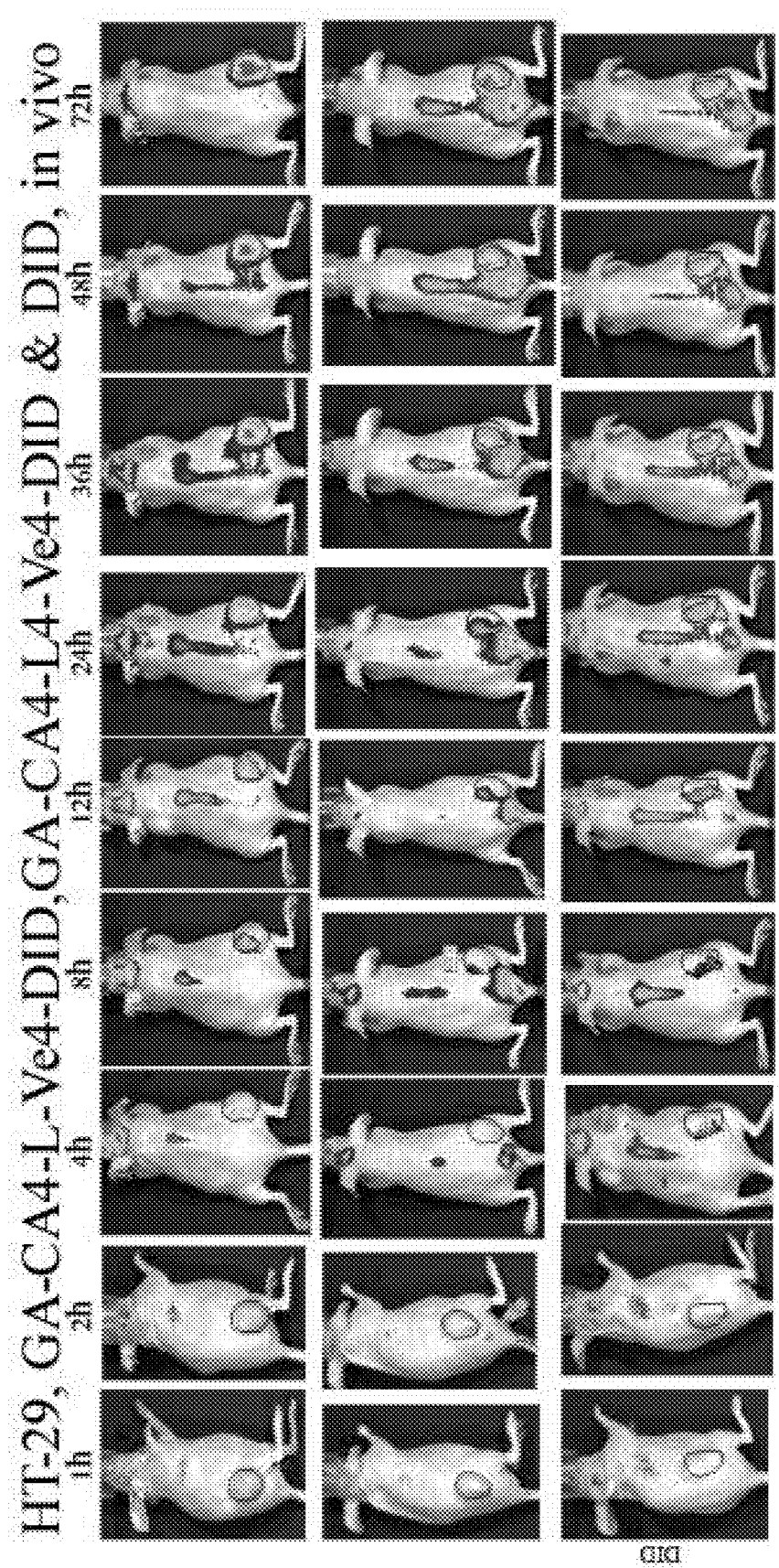
FIG. 19. Example of an in vivo animal imaging of the HT-29 colon cancer bearing nude mice xenograft models after tail vein injection of NIR dye DiD and the DiD-Gambogic acid co-loaded nanoparticles.
Figure 19:
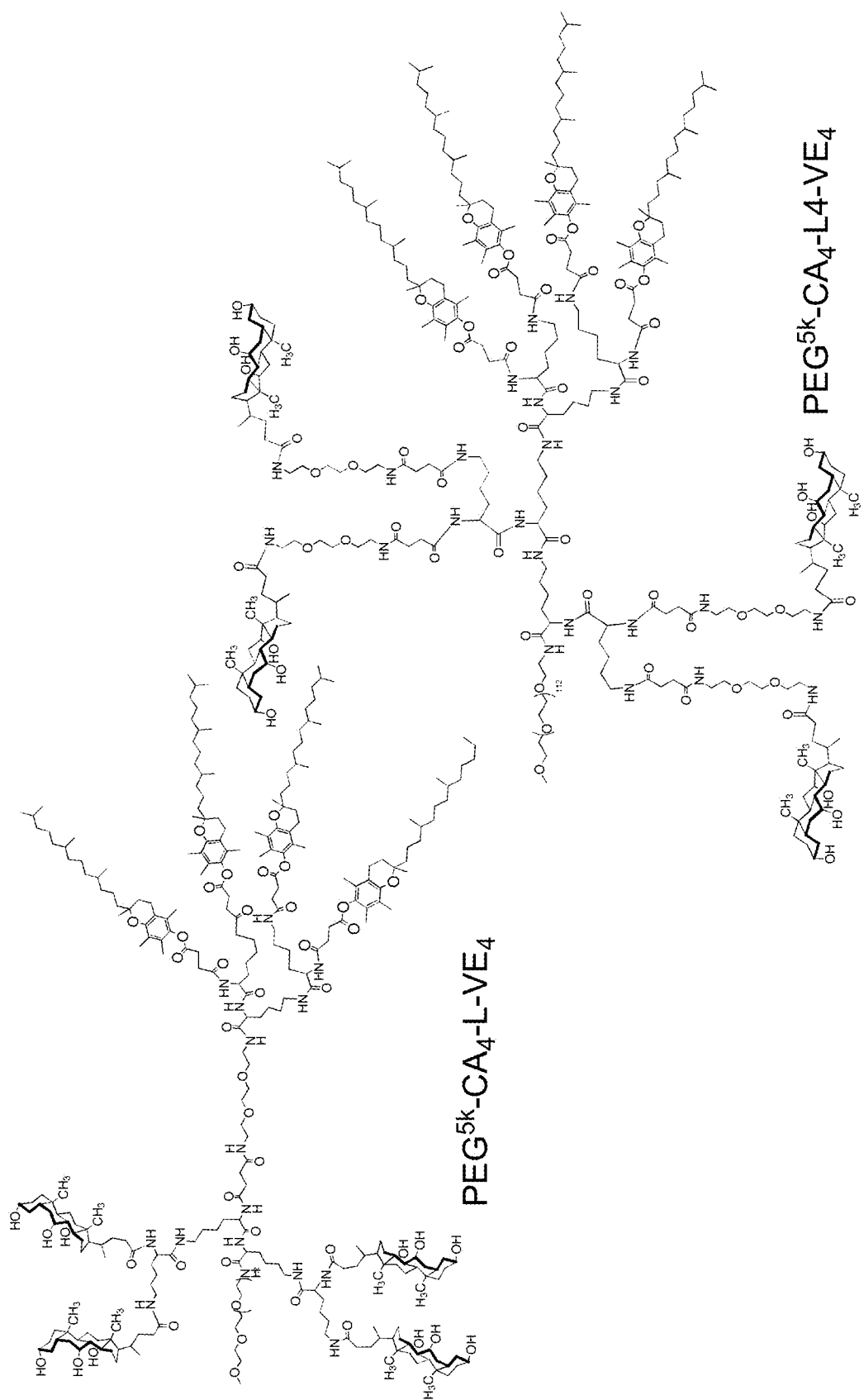
Figure 19:
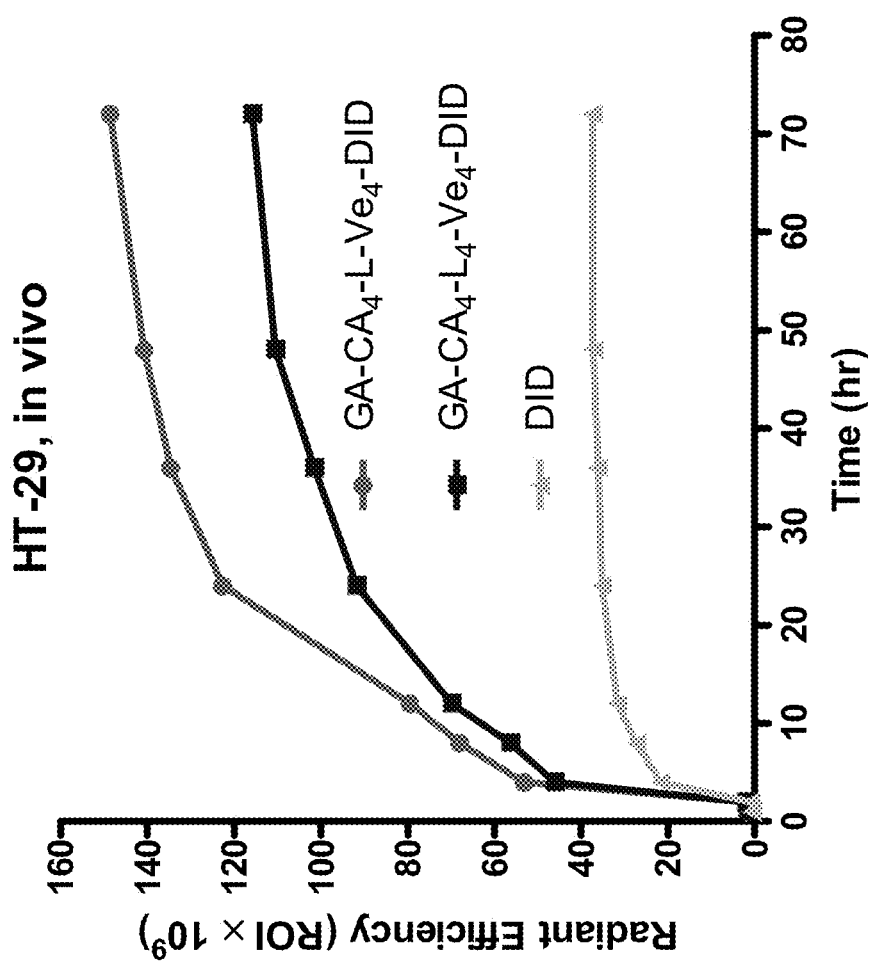
Figure 20:
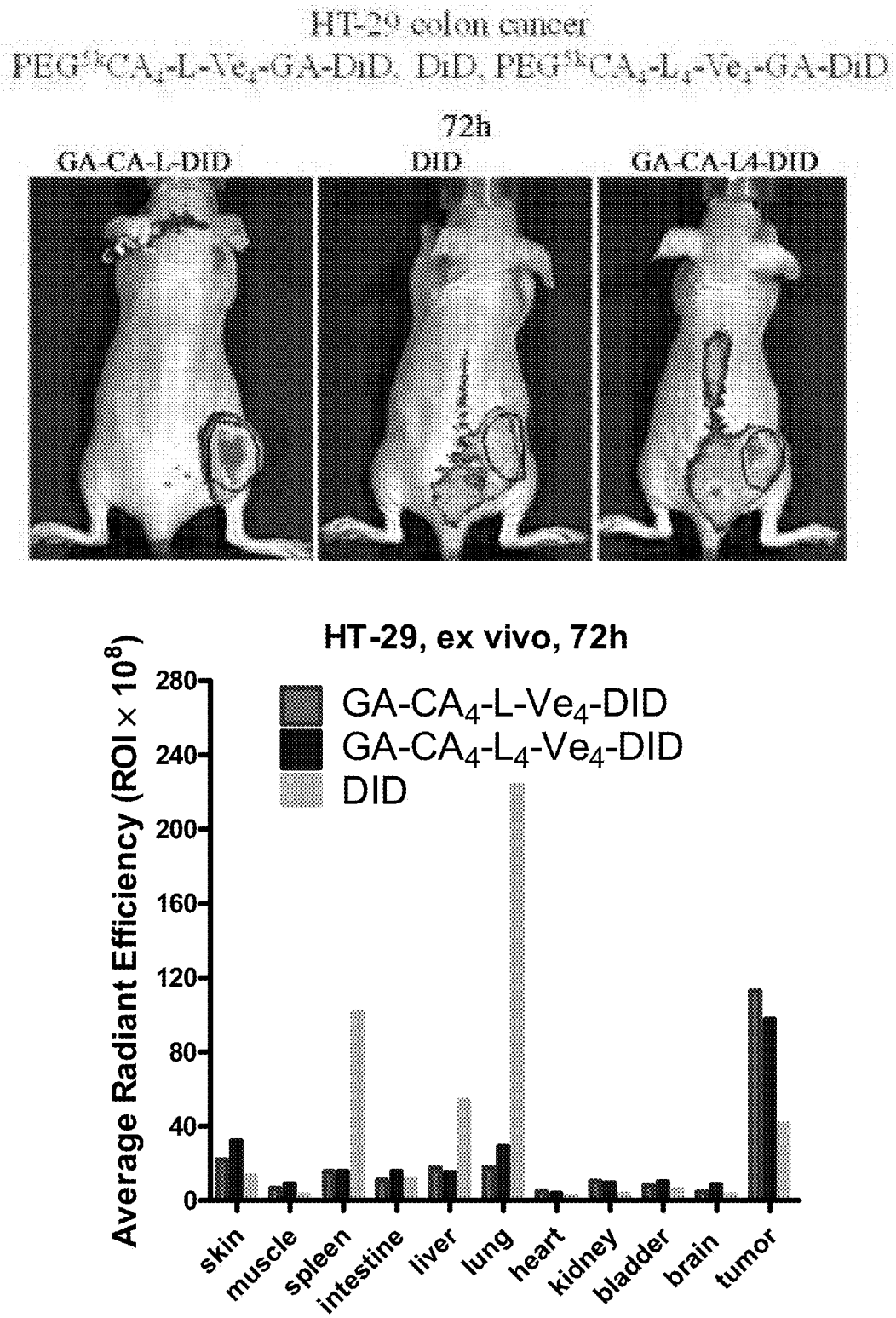
FIG. 20. Example of an in vivo and ex vivo animal imaging and the biodistribution of the NIR signal in the HT-29 colon cancer bearing nude mice xenograft models 72 hours post tail vein injection of NIR dye DiD and the DiD-Gambogic acid co-loaded nanoparticles.
Figure 20:
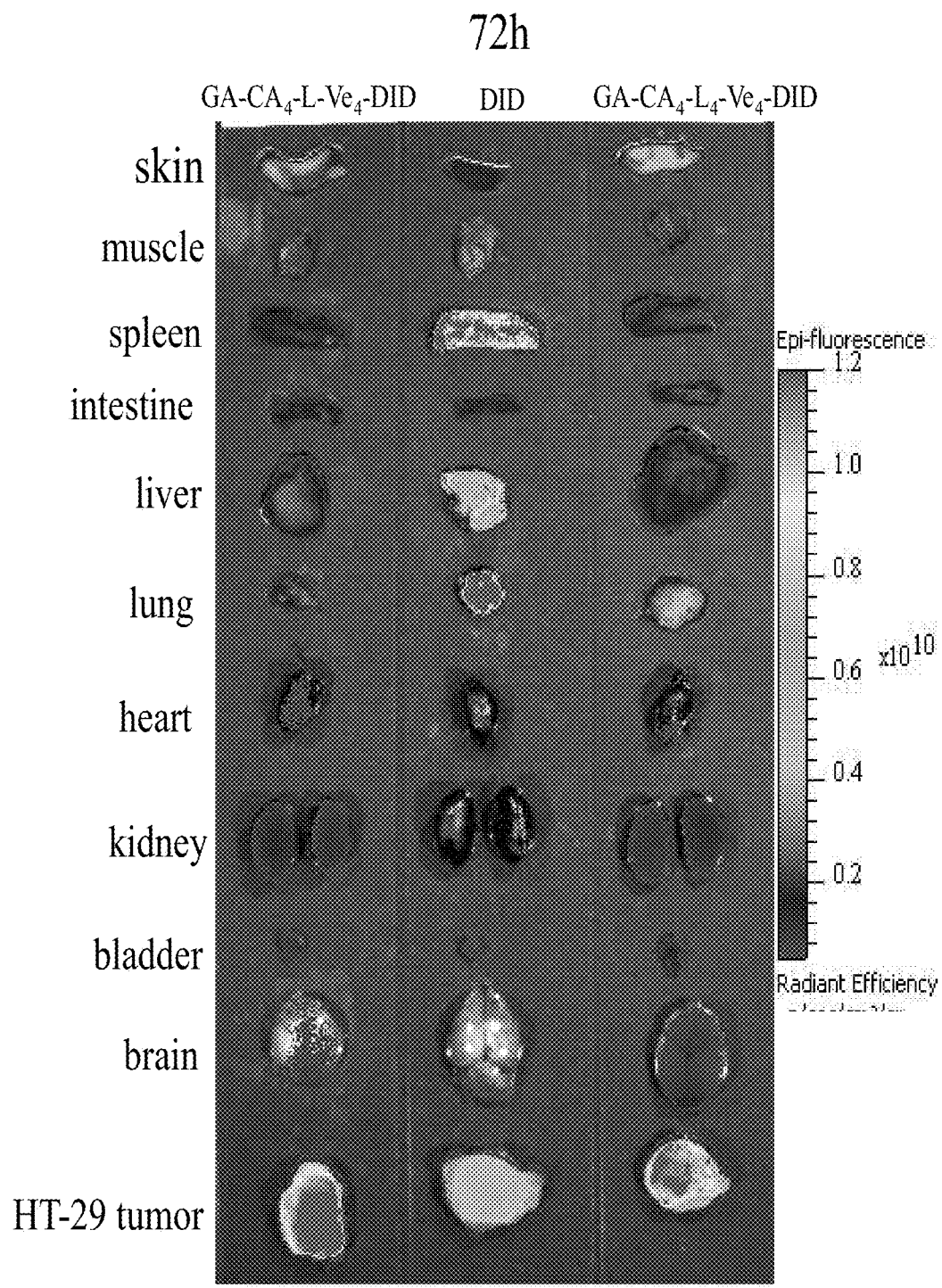
Figure 21:
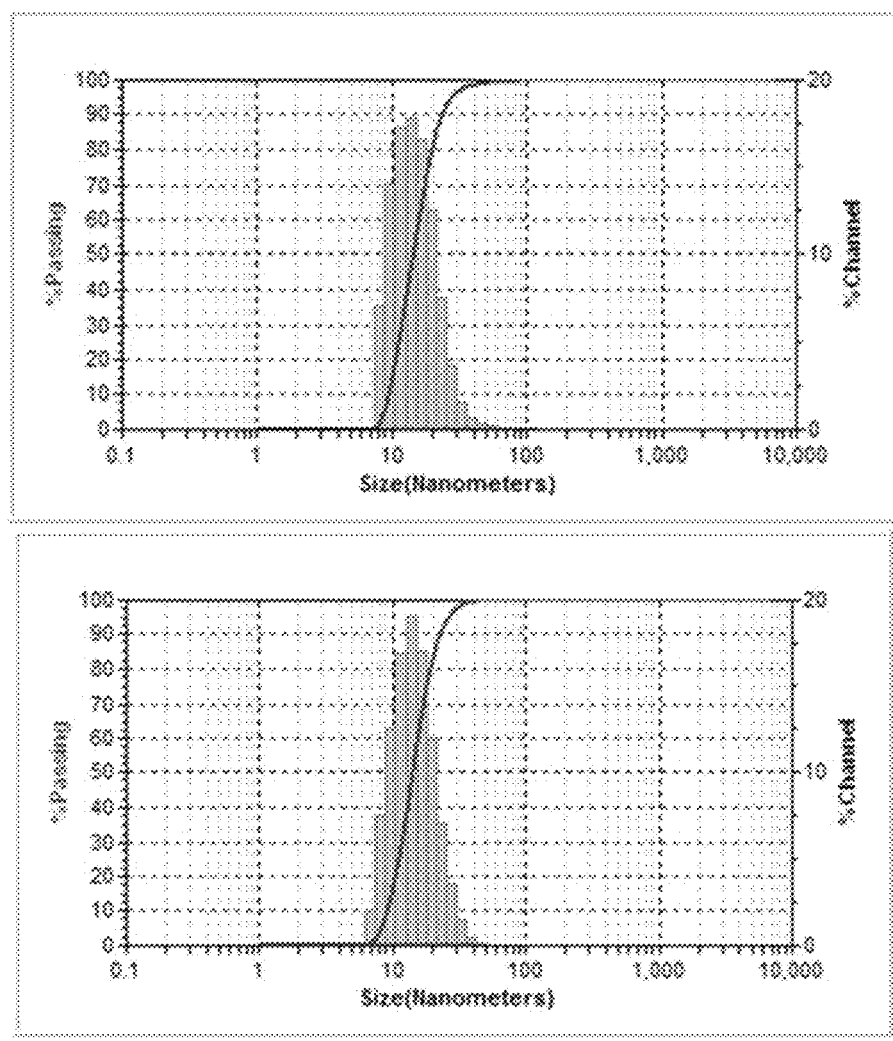
FIG. 21. Exemplary size of DOX-loaded rhein containing two layered and three layered telodendrimer micelles.
Figure 22:
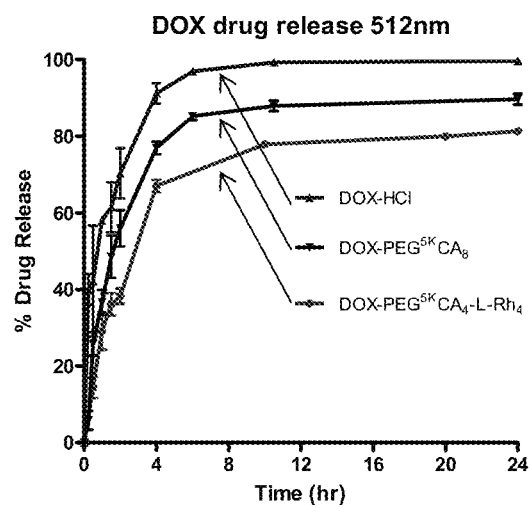
FIG. 22. Doxorubicin release profiles of free DOX and DOX loaded in different nanocarriers. 300 uL of the drug solutions were dialyzed against the frequently refreshed 4 L of dd-water. The remained drug content within the dialysis bag (3500 MWCO) was analyzed via UV-Vis absorbance at 512 nm to eliminate the background absorbance from rhein containing nanocarriers.

Small animal imaging has been performed to study tumor-targeted drug delivery and biodistribution of the Ve containing functional segregated telodendrimer micelles after being co-loaded with NIR dye DiD and gambogic acid. As shown in FIG. 19, the in vivo animal imaging indicated that the telodendrimers with one or four PEG linkers can target xenograft HT-29 colon cancers efficiently. The fluorescent signal in the tumors in the animals treated with nanoformulations accumulated continuously and peaked at 72 hour postinjection. On the contrary, the animal treated with free DiD, nonspecific binding and low tumor uptake were observed as normal. In FIG. 20, the ex vivo imaging clearly showed that the highest signal was observed at the tumor in the animals treated with the nanoformulations. All other organs show very low fluorescence signal in the nanoformulation treatment. However, the high uptake in liver, lung and spleen and low uptake in tumor were seen in the animals treated with free DiD. With efficient tumor targeting, it is expected that the nanoformulations will significantly improve the anticancer effects in vivo, which will be tested further.

Functional Segregated Telodendrimer Containing Rhein for Doxorubicin Delivery.

Figure 6:
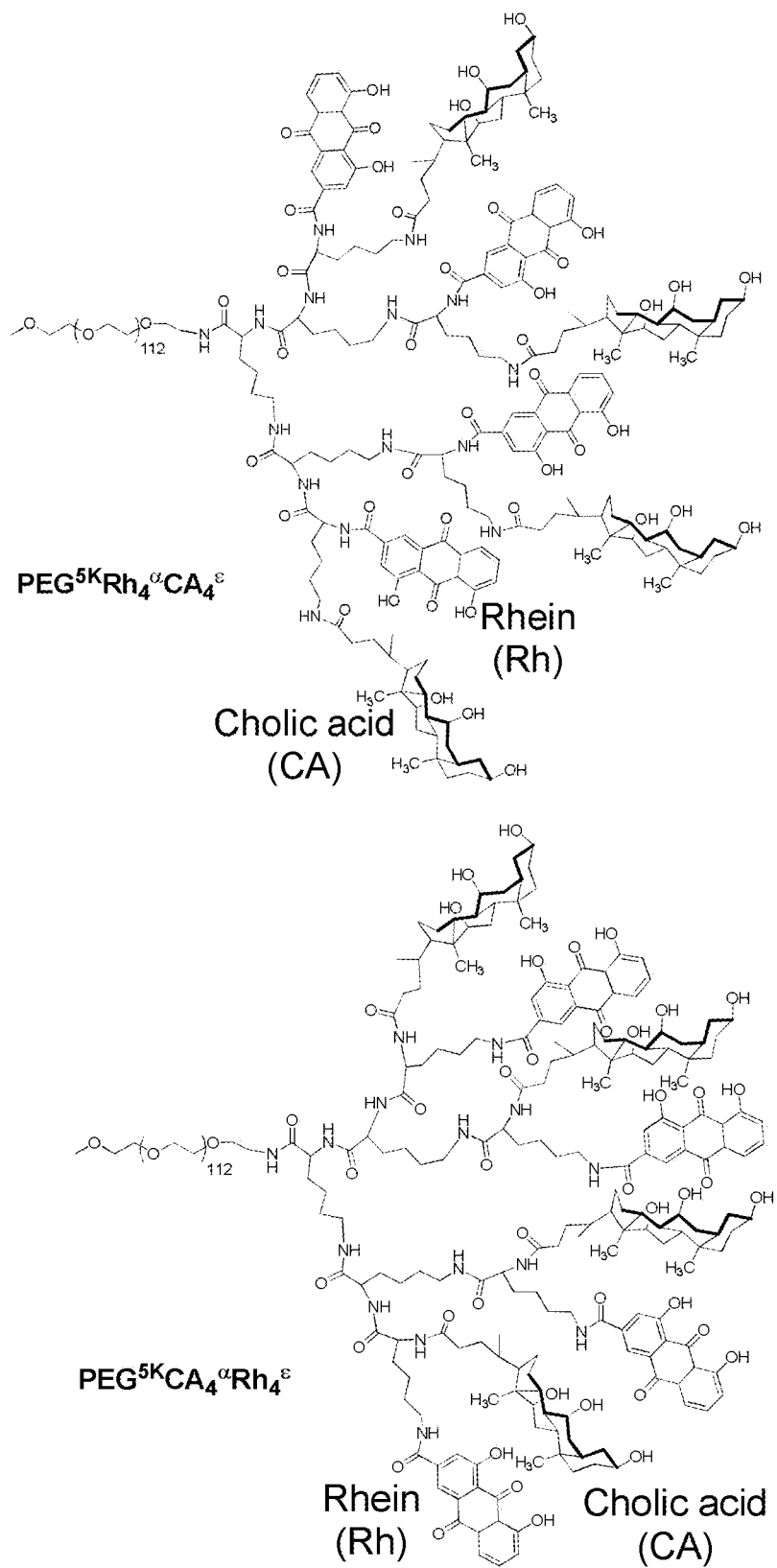
Figure 7:
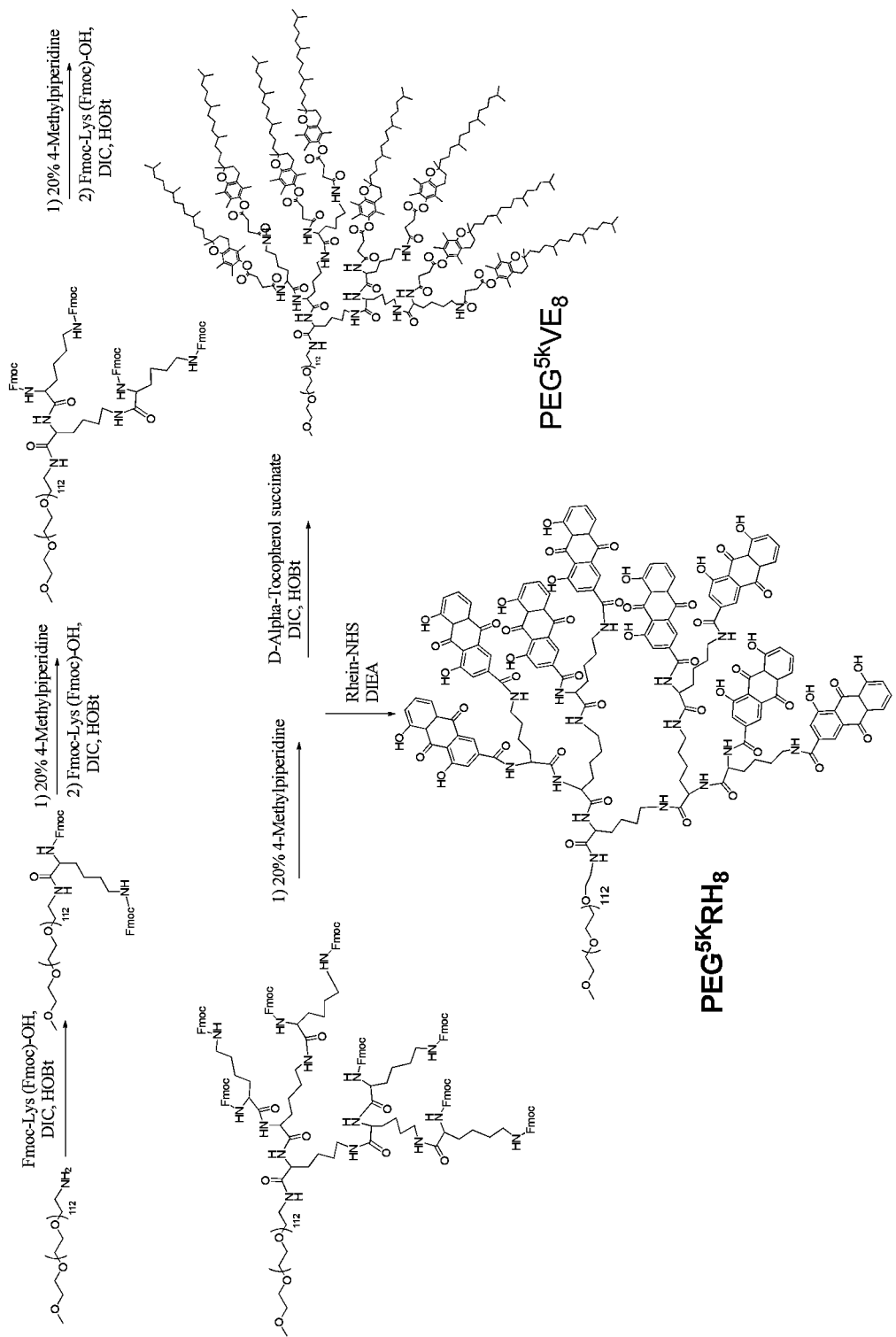

As shown in FIGS. 2, 4 and 6, rhein, a bioactive molecule isolated from traditional Chinese medicine (TCM), can be introduced into a telodendrimer to make bilayered or trilayered telodendrimers for efficient delivery of doxorubicin, due to the specific interactions between rhein and doxorubicin, such as π-π interaction, hydrogen bonding and hydrophobic interactions. Similar to the VE-containing telodendrimers, $PEG^{5k}Rh_8$ with only rhein molecules as the core forming building blocks has poor water solubility and poor drug loading capacity and stabilities. Instead, the telodendrimers with CA and Rhein as core-forming building blocks in the different architectures, e.g., trilayered or bilayered structures, both exhibited good loading capacity and stability for doxorubicin encapsulation. It should be noted that the trilayered telodendrimer $PEG^{5k}CA_4$-L-$RH_4$ is a new compound, while the rhein containing bilayered telodendrimers $PEG^{5k}CA^{\alpha}_4RH^{\varepsilon}_4$ and $PEG^{5k}RH^{\alpha}_4CA^{\varepsilon}_4$ have been disclosed previously. For the purpose of comparison, both these two structures are also discussed here, as shown in Table 3. Compared with the typical telodendrimers, $PEG^{5k}CA_8$ and $PEG^{2k}CA_4$, rhein telodendrimer significantly increases the Dox loading capacity and stability without any precipitation observed over storage for months. The particle sizes of the DOX-loaded micelles have a size of about 10 to 15 nm with narrow SDs (FIG. 14). Due to the increased flexibility, the particle sizes and the reproducibility for DOX loading in the $PEG^{5k}CA_4$-L-$RH_4$ was improved. Both these two formulations can target in vivo tumors efficiently and yield high tumor inhibition.

Figure 23:
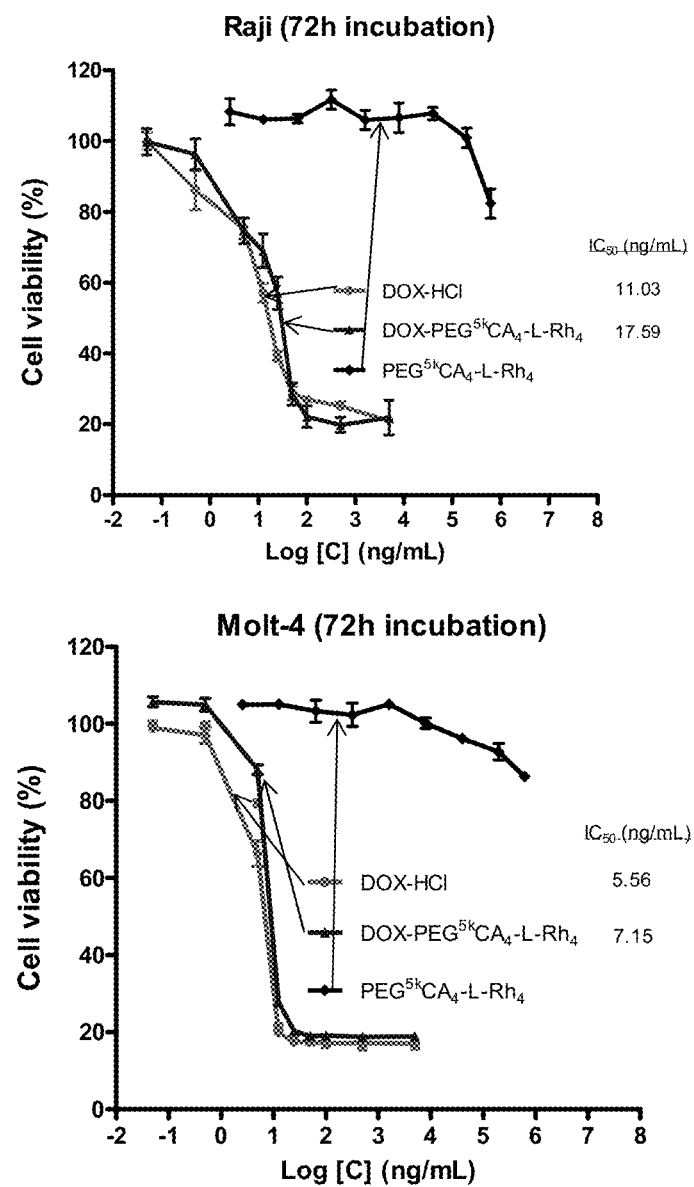
FIG. 23. Example of cytotoxicity of PEG$^{5k}$CA$_4$Rh$_4$ and PEG$^{5k}$CA$_4$-L-Rh$_4$ and Dox-loaded nanoparticles on Raji and molt-4 lymphoma cell lines.
Figure 24:
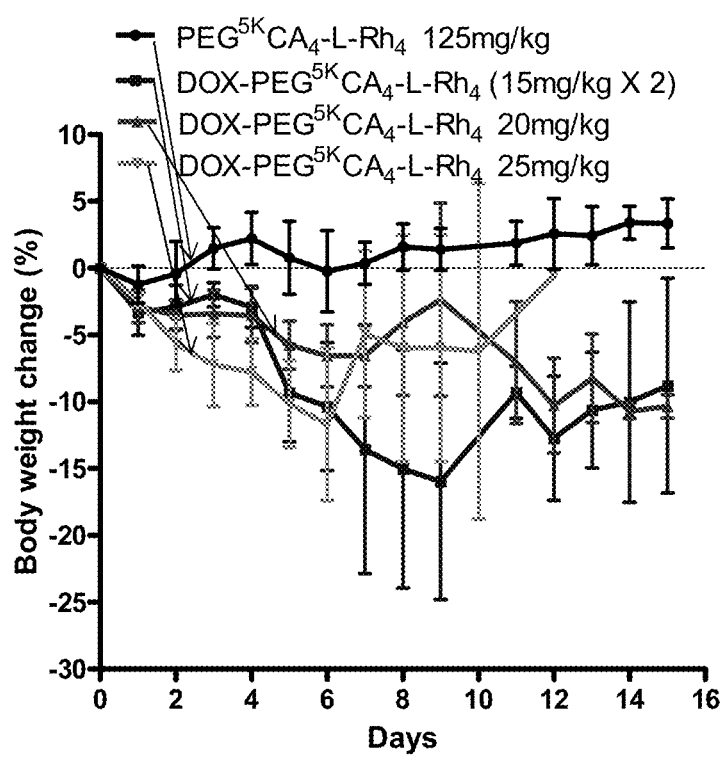
FIG. 24. An example of body weight lost for an animal treated with DOX loaded PEG$^{5k}$CA$_4$-L-Rh$_4$ at different dosage level, as well as the empty micelles for the test of the MTD studies. Among, the 15 mg/Kg dosage was repeated at day 0 and day 4 to study the MTD of multiple dosages.

Doxorubicin can be efficiently loaded in the telodendrimers containing rhein as building blocks. The drug release studies revealed a slower profile for DOX loaded in the Rhein-containing telodendrimer micelles. These telodendrimers are nontoxic up to 0.5 mg/mL (FIG. 23). At even higher concentration, the rhein containing telodendrimers showed moderate cell growth inhibition, which may be related to the anticancer effects of the rhein molecules. The nanoformulation of DOX loaded in the $PEG^{5k}CA_4$-L-$RH_4$ micelles exhibited similar potency in killing lymphoma cancer cell lines, e.g., Raji and Molt-4 cell lines (FIG. 23), compared with the free DOX. The maximum tolerate dosage (MTD) of the DOX-loaded $PEG^{5k}CA_4$-L-$RH_4$ formulation was determined to be 15 mg/Kg for two injections total, one on day 0 and one on day 4 (FIG. 24). The single injection MTD for this formulation was tested at 20 and 25 mg/Kg levels, and events of death or euthanized animal were observed in both groups. These results indicated the single dose MTD should fall between 15 to 20 mg/Kg.

Figure 25:
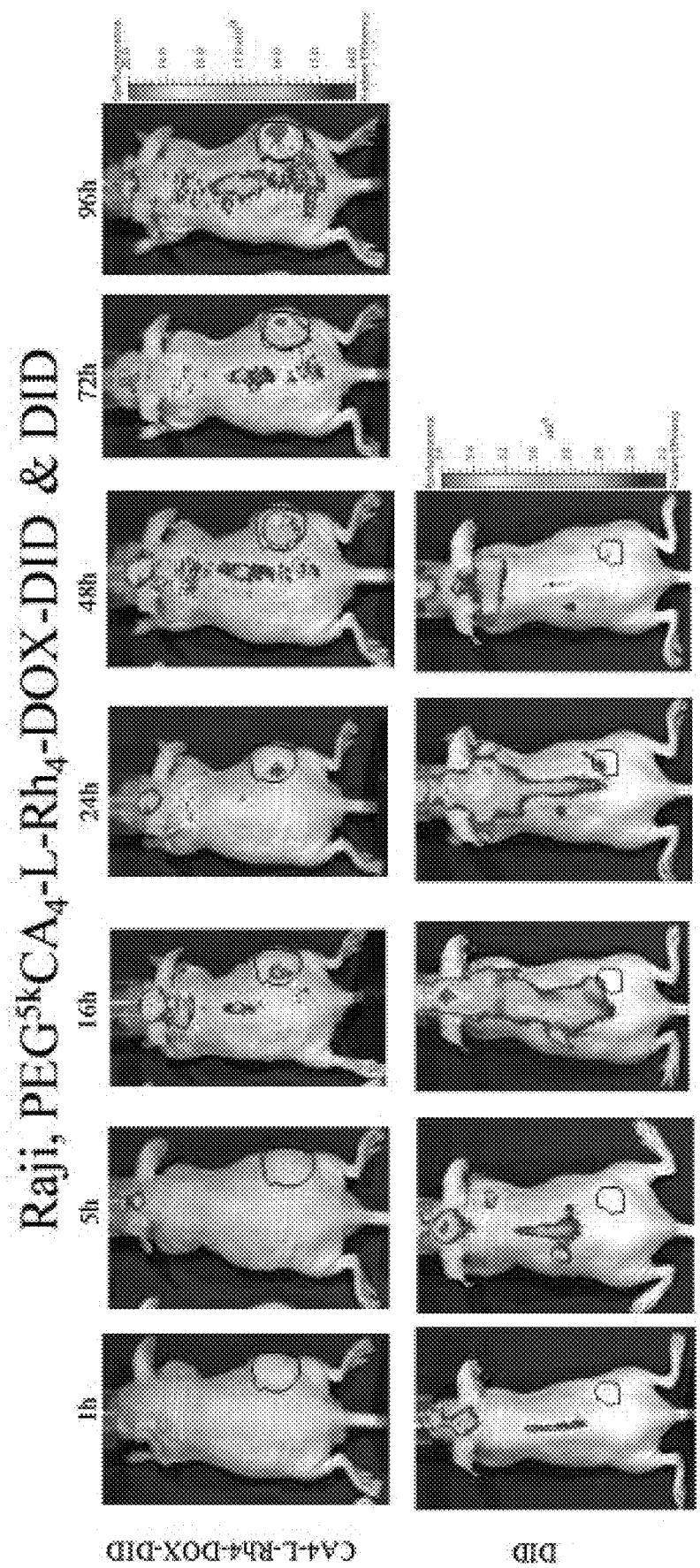
FIG. 25. Example of an in vivo and ex vivo animal imaging and the biodistribution of the NIR signal in the Raji lymphoma bearing nude mice xenograft models post tail vein injection of NIR dye DiD and the DiD-Gambogic acid co-loaded nanoparticles.
Figure 25:
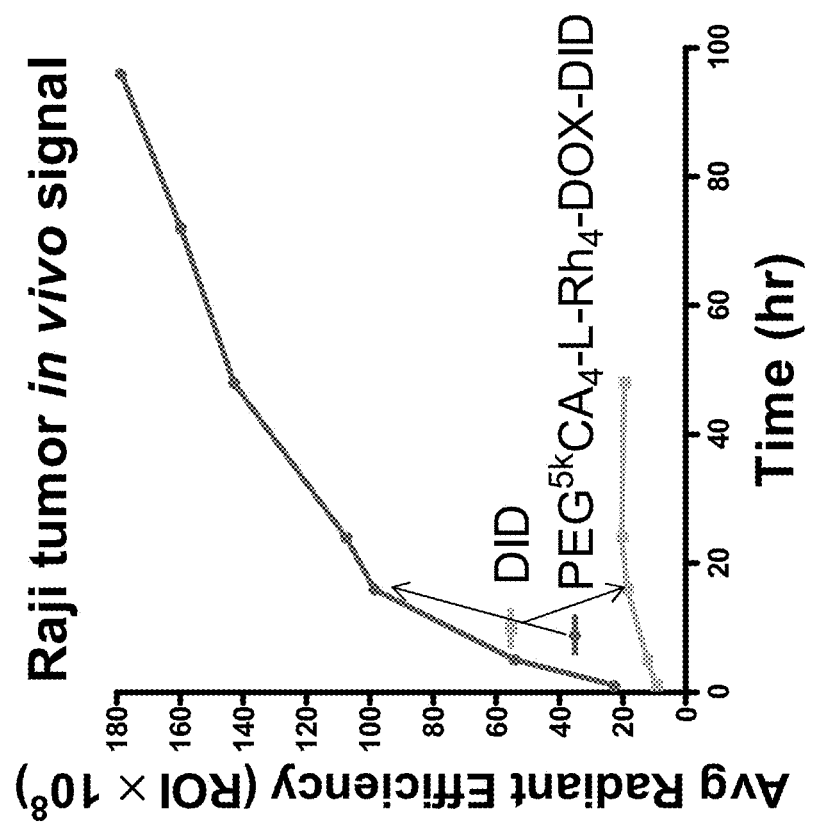
Figure 25:
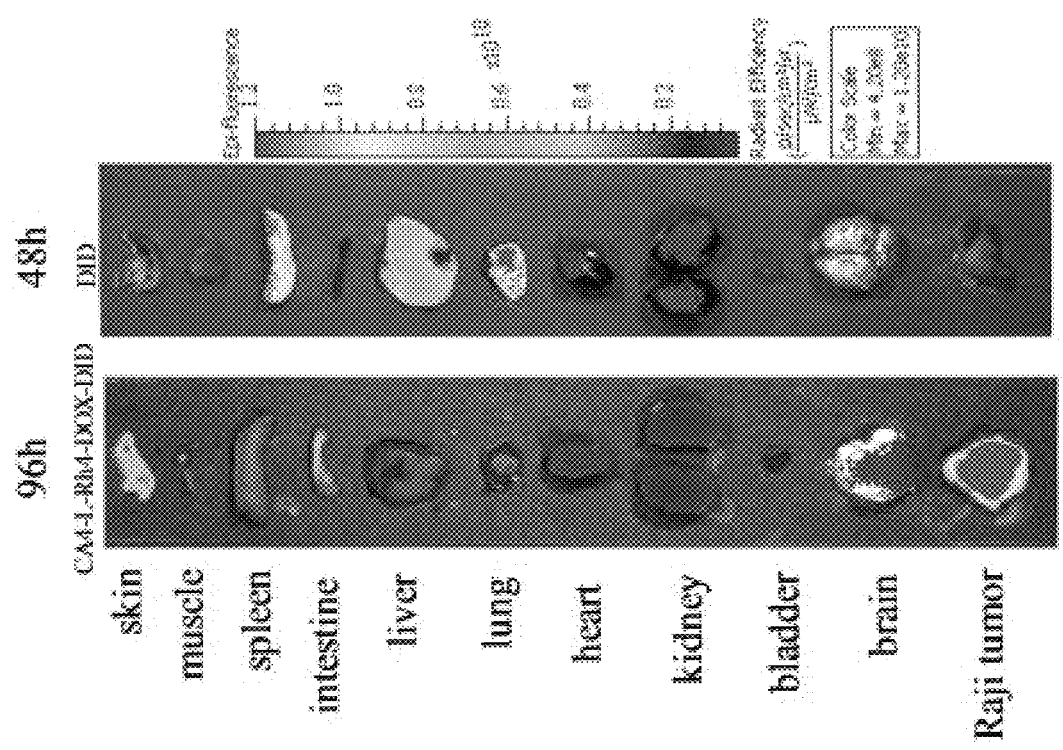
Figure 25:
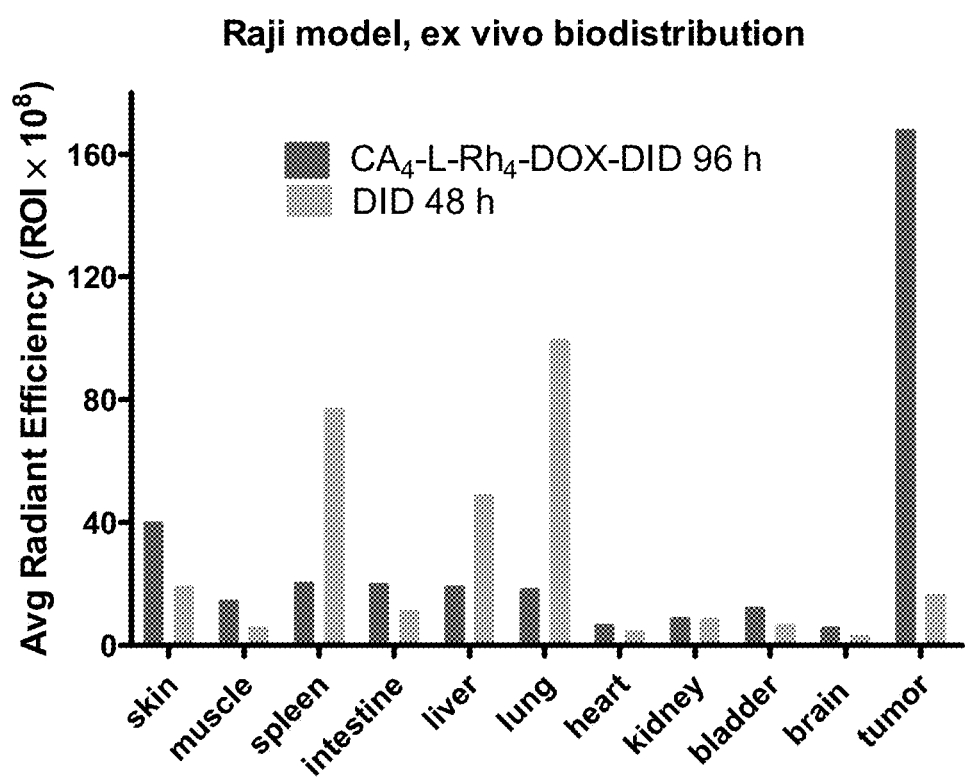
Figure 26:
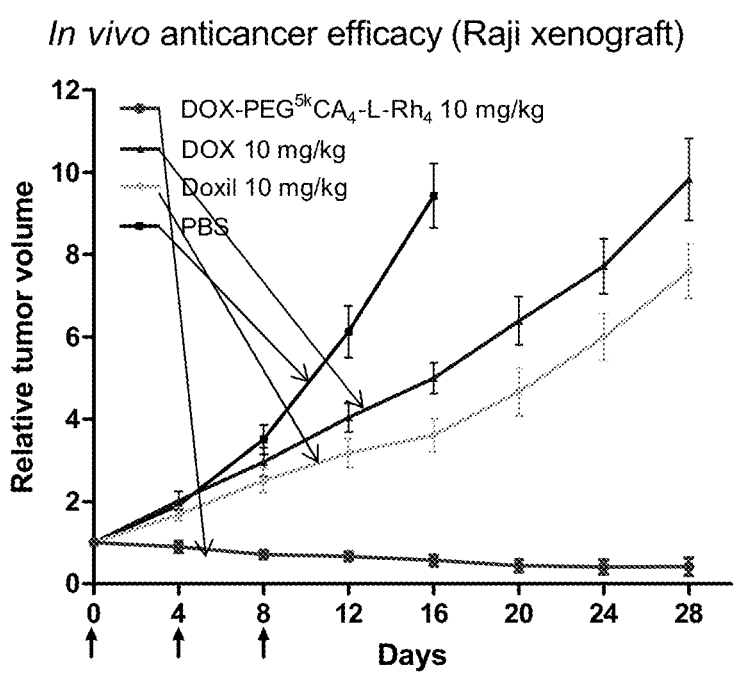
FIG. 26. Example of nude mice bearing Raji lymphoma xenograft (n=5-6) were intravenously administrated with PBS, DOX, Doxil, DOX-PEG$^{5k}$CA$_4$-L-Rh$_4$ at the dose of 10 mg/kg, respectively. The dosage was given every four day for total 3 doses. Relative tumor volume equals the tumor volume at given timepoint divided by the tumor volume prior to initial treatment.
Figure 27:
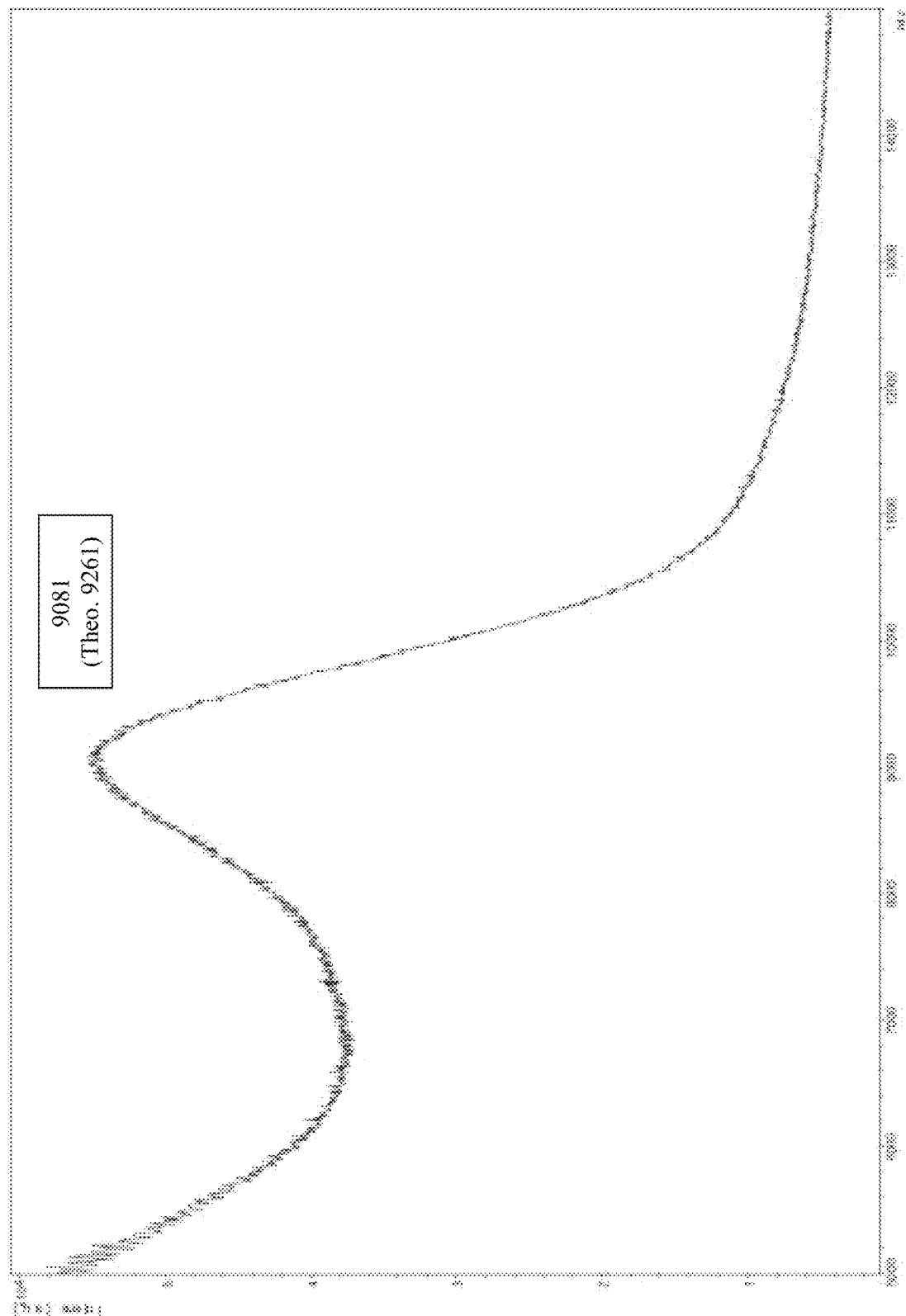
FIG. 27. The structures, and exemplary MALDI-TOF MS, and proton NMR spectrum of two telodendrimers containing cholic acid and coumarin as building blocks (PEG$^{5k}$CA$^{\alpha}_4$LS$_4$Co$^{\varepsilon}_4$ and PEG$^{5k}$CA$^{\varepsilon}_4$LS$_4$Co$^{\alpha}_4$).
Figure 27:
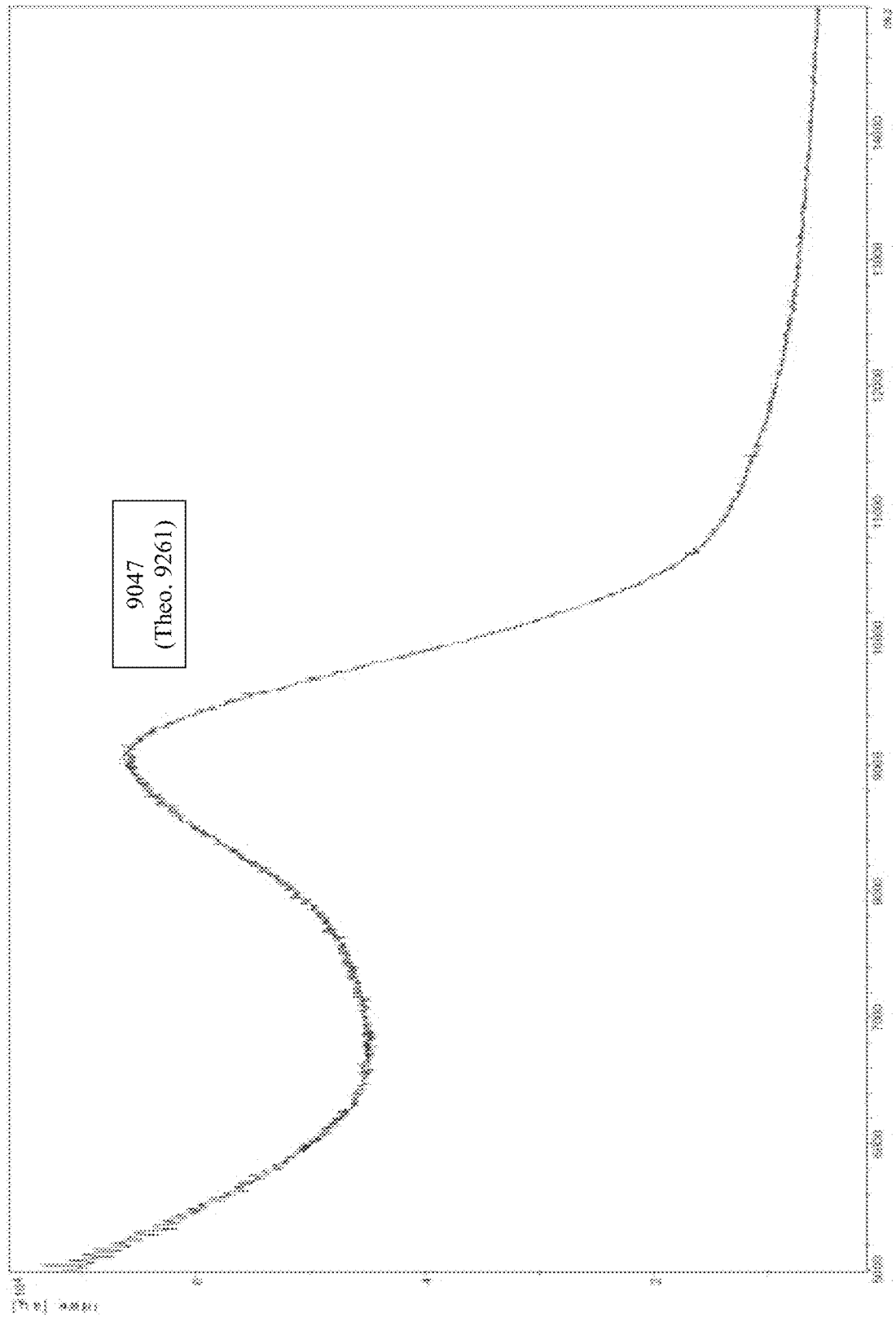
Figure 27:
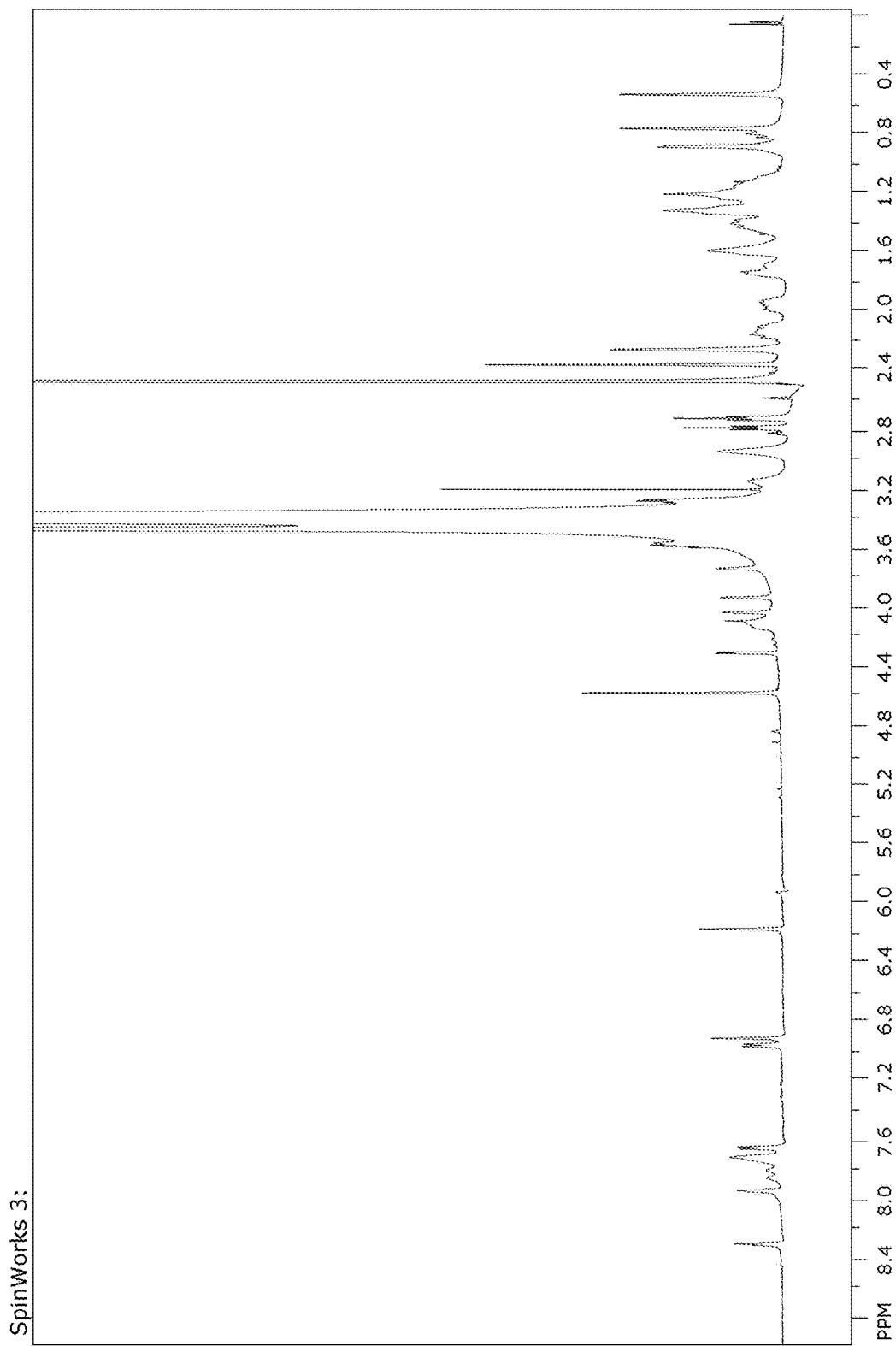
Figure 27:
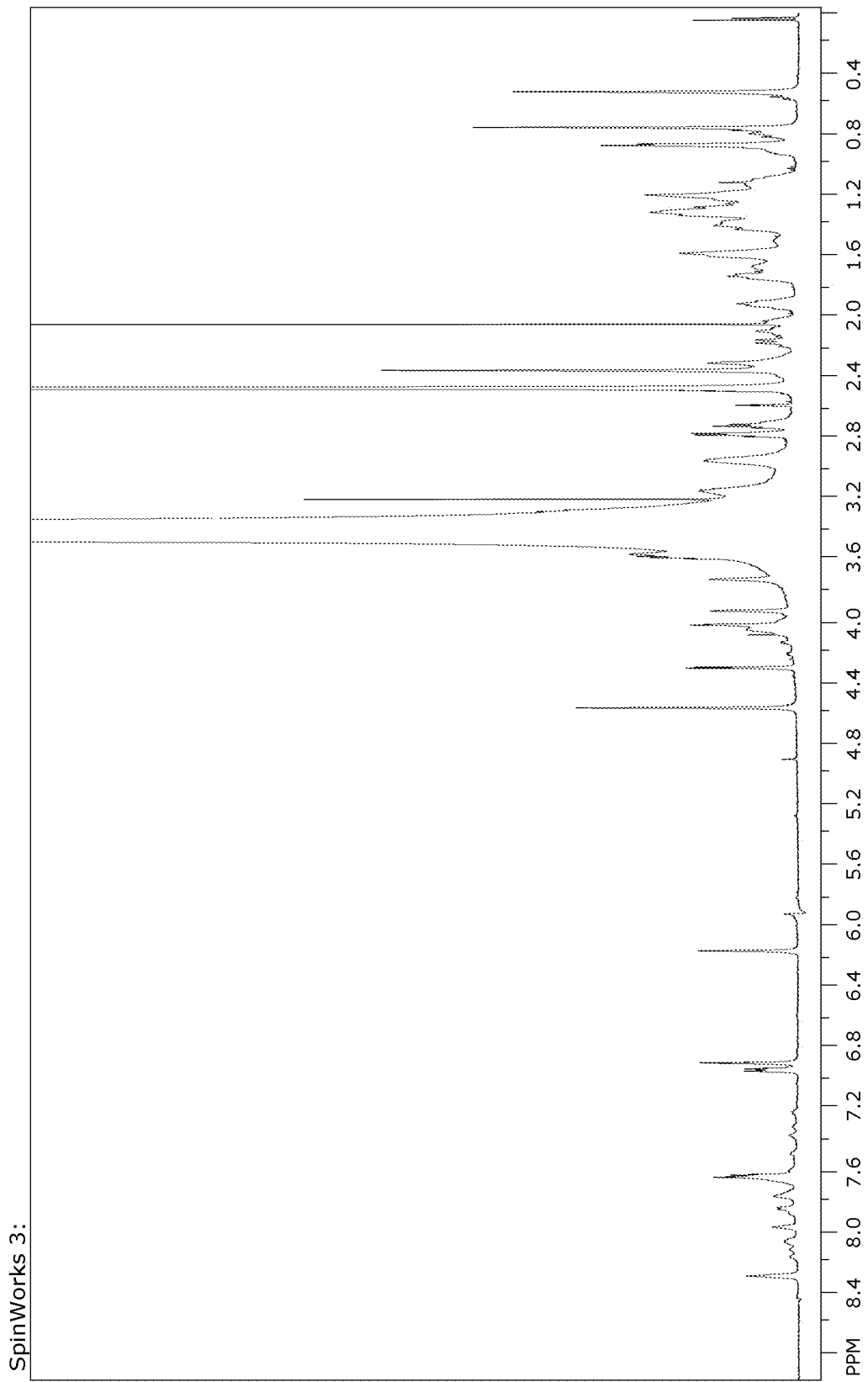

Near Infrared Fluorescence dye DiD was co-loaded in the $PEG^{5k}CA_4$-L-$RH_4$ micelles with DOX and was injected via the tail vein into nude mice bearing Raji lymphoma xenograft for biodistribution study (FIG. 25). It revealed that nanocarriers can deliver the payload to the cancer site efficiently via EPR effects with the continued accumulation even at 96 hours postinjection. Both in vivo and ex vivo imaging analysis revealed that about eight-fold higher fluorescent signal was detected in the tumors treated with nanoformulation compared with that in the free DiD injection. In the ex vivo biodistribution imaging after the last in vivo imaging (96 h), the tumor in the animal treated with the nanoformulation had the highest fluorescent intensity, with signal eight fold higher than the signal in other vital organs, such as in liver, lung and heart. As expected, high fluorescent uptake in the liver, lung and spleen and weak signal in the tumor were seen in the animal treated with free DiD.

The in vivo efficacy study in the nude mice bearing Raji lymphoma xenografts was carried out in comparison with free DOX and the PEGylated liposomal formulation of doxorubicin (Doxil). The animal treated with DOX-$PEG^{5k}CA_4$-L-$RH_4$ nanoformulation at 10 mg/kg for three dosages on days 0, 4 and 8 showed significantly better response with tumor shrinking observed over four weeks. For the DOX and Doxil treatment groups at the same dose level, the cancer progression was slowed down compared with the control PSA group. However, the tumor sizes rapidly reached the maximum tolerable tumor sizes. It showed that the Rh-engineered nanoformulation can minimize side toxicity while targeting the tumor efficiently and killing the cancer efficiently, which is believed due to the improved stability of the nanoformulation.

TABLE 3

Size of the drug or dye loaded micelles by DLS

| Polymers | Size (nm) | | |
|---|---|---|---|
| | DOX (Polymer/drug) | DOX + DiD (Polymer/drug/DiD) | Triptolide (TPL) (Polymer/drug) |
| $PEG^{5k}$-$CA_4$-L-$RH_4$ | 14 ± 5 (10:2 w/w) | 30 ± 13 (10:1.5:0.25 w/w) | — |
| $PEG^{5k}$-$CA_4$-$RH_4$ | 14 ± 5 (10:2 w/w) | 21 ± 8 (10:1.5:0.25 w/w) | — |
| $PEG^{5k}CA_8$ | 12 ± 5 (10:1 w/w) | — | 11 ± 2 (5:1 w/w) |
| $PEG^{2k}CA_4$ | 10 ± 2 (10:1.5 w/w) | — | — |

Functional Segregated Telodendrimer Containing Coumarin for SN-38 Delivery.

As shown in Table 4, series telodendrimers with coumarin as building blocks have been synthesized via the similar peptide chemistry approach used in making Rhein- and Ve-containing telodendrimers. Coumarin is a photosensitive molecule, which undergoes reversible dimerization upon UV light irradiation. In addition, a disulfide bond containing linker is introduced into the telodendrimer prior to the coumarin moiety in order to allow decrosslinking of the micelles upon entering the reducing intratumoral and intracellular microenviroments in the tumor. An exciting finding was that these coumarin containing telodendrimer can encapsulate SN-38 very efficiently with stable and monodispersed particle sizes. These nanoformulations will be able to bring SN-38 into the clinic for colon and lung cancer as well as for other cancer treatments. In addition, the location of the coumarin groups in the interior layer has been found to be very important for the delivery of SN-38. For example, $PEG^{5K}CA_4LO$-$LS_4Co_4$ can encapsulate SN-38 at as high as a 10:3 polymer/drug ratio with 100% loading efficiency. The coumarin moiety can form a complex with SN-38 in the inside core of the micelle and the cholic acid in the intermediate layer is able to stabilize the payload and the nanoparticles, due to its facial amphiphilicity. The particle sizes of the SN-38 loaded nanoparticles have been determined via a DLS particle sizer to range from 25 nm to 50 nm with the increased amount of drug content. The particle sizes were stable upon storage without significant changes in size after 30 days at 4° C. The particle sizes of the SN-38-loaded $PEG^{5K}CA_4LO$-$LS_4CO_4$ micelles at a 10:1 polymer/drug ratio shrank from 33.60±10.70 to 26.2±8.8 nm after photocrosslinking (45% crosslinking degree analyzed via UV-Vis absorbance).

In contrast, $PEG^{5K}LS_4CO_4LO$-$CA_4$ is not able to encapsulate SN-38 efficiently, with poor size distribution and stability. In comparison, $PEG^{5k}CA_8$ and $PEG^{5k}CO_8$ have also been prepared and tested in SN-38 loading to study the critical role of the polymer architecture as well as the affinity building blocks. It turned out that $PEG^{5k}CA_8$ can load PTX only at a 10:1 ratio with large particle sizes (128±55 nm), which further aggregated into 466 nm upon storage over 24 hours. Interestingly, $PEG^{5k}CO_8$ can encapsulate SN-38 efficiently at a 10:1 polymer/drug ratio. The particle sizes are relatively stable at 39±12 nm even after storage for a month. However, precipitation homogenous and heterogeneous size distribution were observed upon the increased drug content at a 10:2 polymer/drug ratio. It should be pointed out that the drug concentration at a 10:1 ratio of $PEG^{5k}CO_8$ to SN38 is high enough for further in vitro assays and in vivo efficacy study, as well as for human patient treatment. As it is easy to synthesize, $PEG^{5k}CO_8$ is worthy to be developed and evaluated for SN-38 delivery for in vivo cancer treatment.

TABLE 4

Coumarin containing tri-layered telodendrimers for the encapsulation of SN-38

| sample name | structure | Ratio (Polymer:SN38) | concentration | Size (nm) |
|---|---|---|---|---|
| PEG$^{5K}$CA$_4$LO-LS$_4$CO$_4$ | (structure diagram with PEG$_{5000}$—K—K—O-Linker-K branching to S—S-Linker-Co groups, with AC, CA, CA, CA substituents) | 10:0.5 | 10:0.5 mg/ml | 24.68 ± 7.67<br>Store 48 h: 28.73 ± 11.02 |
| | | 10:1 | 10:1 mg/ml | 33.60 ± 10.70 (no crosslink)<br>26.16 ± 8.8 (crosslinking)<br>Store 24 h:<br>31.60 ± 11.23 (no crosslinking)<br>28.82 ± 9.66 (crosslinking) |
| | | 10:1.5 | 5:0.75 mg/ml | 31.90 ± 9.96<br>Store 24 h: 34.90 ± 12.35<br>Store 48 h: 33.90 ± 11.38 |
| | | 10:2 | 5:1 mg/ml | 33.20 ± 10.79<br>Store 24 h: 35.30 ± 10.56<br>Store 48 h: 35.60 ± 12.83 |
| | | 10:3 | 5:1.5 mg/ml | 49.90 ± 14.04 (13)<br>Store 24 h: 44.4 ± 13.89 |
| | | 10:4 | 5:2 mg/ml | precipitation |
| PEG$^{5K}$LS$_4$Co$_4$LOCA$_4$ | (structure diagram with PEG$_{5000}$—K—K—O-Linker-K branching to CA groups and Co—S—S linkages) | 10:1 | 5:0.5 mg/ml | 105.1 ± 59.50<br>Store 24 h: 144.5: 46.5%<br>58.90: 27.0%<br>40.90: 26.5% |
| | | 10:2 | 5:1 mg/ml | 4400: 1%<br>1045: 17.5%<br>389.0: 25.5%<br>154.1: 56.0% |
| PEG$^{5K}$CA$^{\alpha}_4$LS$_4$Co$^{\varepsilon}_4$ | | 10:1 | 10:1 mg/ml | 17 ± 4 nm |
| PEG$^{5K}$CA$^{\varepsilon}_4$LS$_4$Co$^{\alpha}_4$ | | 10:1 | 10:1 mg/ml | 20 ± 5 nm |
| PEG$^{5K}$CA$_8$ | (dendrimer structure PEG$_{5K}$—K branching to 8 CA groups via K linkers) | 10:1 | 5:0.5 mg/ml | 128.4 ± 55.10 nm<br>Store 24 h: 466.0 nm: 5%<br>67.50 nm: 95% |
| PEG$^{5K}$Co$_8$ | (dendrimer structure PEG$_{5K}$—K branching to 8 Co groups via K linkers) | 10:1 | 5:0.5 mg/ml | 39.10 ± 11.69 nm<br>Store 2 days: 38.50 ± 13.39 nm |
| | | 10:2 | 5:1 mg/ml | Store 30 days: 34.8 ± 11 nm<br>986 nm (34%); 380 nm (64%) |

Photosensitive Reversibly Crosslinked Telodendrimers. Core Crosslinked Telodendrimer Micelles.

Two types of the polymers with alternating cholic acid and courmarine as building blocks, namely PEG$^{5k}$CA$^{\alpha}_4$LS$_4$Co$^{\varepsilon}_4$ and PEG$^{5k}$ CA$^{\varepsilon}_4$LS$_4$Co$^{\alpha}_4$, have been designed and synthesized via the peptide chemistry as described previously (FIG. 27). The molecular weights of these two telodendrimers were analyzed via MALDI-TOF to be very close to the theoretical value. Proton NMR also revealed the correct chemical structure (4:4 CA/Coumarin mol/mol) according to the peak integrations of cholic acid (0.6 ppm) and coumarin (5.2 ppm). However, the same chemical component, the PTX-loaded PEG$^{5k}$ CA$^{\alpha}_4$LS$_4$Co$^{\varepsilon}_4$ micelles, displayed higher stability and drug-loading efficiency as compared to micelles formed by PEG$^{5k}$ CA$^{\varepsilon}_4$LS$_4$Co$^{\alpha}_4$. The differences in properties between the two telodendrimers may be related to the cholic acid-attached position in the polymer structures, leading to a different self-assembled micelle structure.

Figure 28:
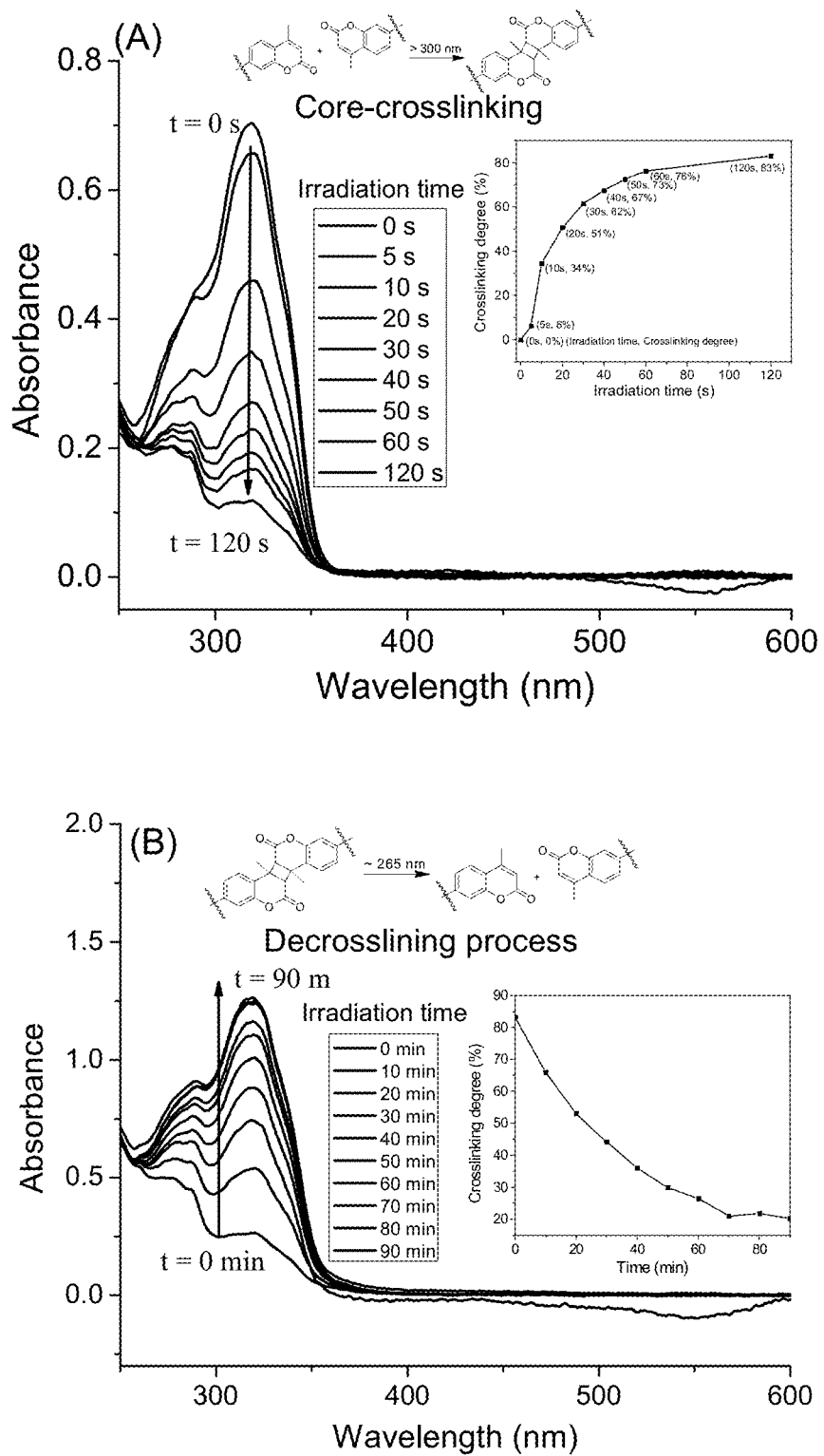
FIG. 28. UV-vis spectra of a micellar solution formed from PEG$^{5k}$CA$^{\alpha}_4$LS$_4$Co$^{\varepsilon}_4$: (A) under UV irradiation at λ>310 nm, the inset showing the increase in crosslinking (photodimerization) degree; (B) under UV irradiation at ~265 nm, the inset showing the decrease in crosslinking degree.

4-methylcoumarin exhibits reversible photodimerization reactivity and has been employed in photocrosslinking reactions. Therefore, incorporation of 4-methylcoumarin into the polymer backbone enables the polymer to respond to photo-initiation for reversible micelle crosslinking. FIG. 28 shows the reversible photo-cross-linking of micelles formed from $PEG^{5k}CA^{\alpha}_{4}LS_{4}Co^{\epsilon}_{4}$ as an example. When the micellar solution (4 mg/mL) was exposed to UV light at $\lambda$>300 nm (100 mW/cm$^2$ from a UV-vis spot curing system), the absorption of coumarin moieties at around 320 nm decreased continuously with time, indicating the occurrence of dimerization (crosslinking) in the micelles; the inset gives the increase in the dimerization degree as estimated from the change in absorbance at 320. Interestingly, polymers displayed very rapid crosslinking kinetics, and dimerization degree may reach up to 60% within 1 minute of irradiation time. Furthermore, crosslinking degree can be precisely controlled by varying irradiation time or light energy. When the core cross-linked micellar solution was illuminated by a UV ($\lambda$=256 nm), the opposite process, i.e., photocleavage of coumarin dimmers, took place as indicated by the recovery of absorption at 320 nm (shown in FIG. 28); the decrease in the dimerization degree is also shown in the inset. The results demonstrate that for the same polymer micelles an easy regulation of the cross-linking density can be obtained by adjusting the irradiation time. Although the photocleavage of coumarin dimmers appeared incomplete, a reversible photocontrol of the crosslinking density could be achieved to a certain degree. Furthermore, a disulfide bond containing spacer molecule has been introduced prior to the coumarin moiety. Disulfide bonds can be cleaved upon encountering the reducing tumor microenvironment, therefore decrosslinking micelle and releasing drug molecules more efficiently.

Figure 29:
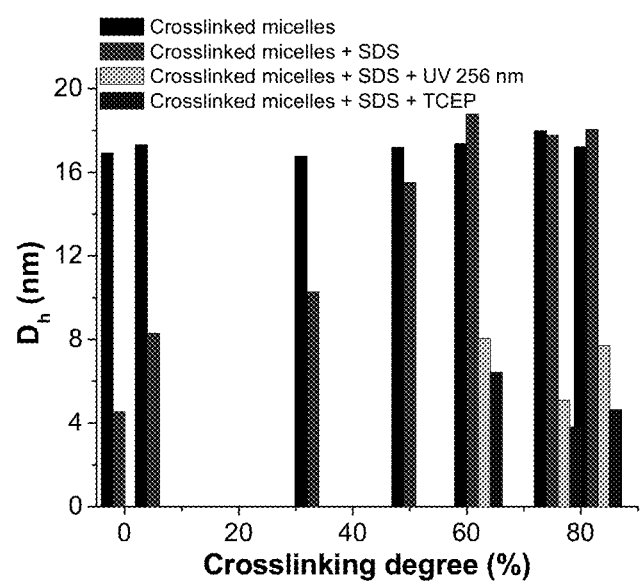
FIG. 29. Particle sizes of the core-crosslinked PEG$^{5k}$CA$^{\alpha}_4$LS$_4$Co$^{\varepsilon}_4$ micelles with different crosslinking degree in the presence of the micelle-dissociating SDS with or without decrosslinking stimuli, such as TCEP or UV 256 irradiation.

Sodium dodecyl sulfate (SDS) is an anionic surfactant, which can efficiently interact with polymer micelles. The electrostatic repulsion between SDS head groups in the copolymer-surfactant leads to dissociation of the micelles. Stability of the micelles could be significantly improved by crosslinking, whereas noncrosslinked micelles were dissociated instantly by SDS. As shown in FIG. 29, the particle sizes of the non-crosslinked micelles (0% crosslinking degree) was broken down from 16.9 nm to 4.5 nm by the addition of SDS. With the increased crosslinking degrees from 6%, 34% to 51%, the SDS-dissociated particle sizes became bigger and bigger. With the crosslinked micelles with a crosslinking degree higher than 62%, there was no reduction in particle size upon the addition of SDS. Instead, slightly swollen of particle sizes was seen upon addition of SDS. This indicated that stable micelles were obtained via the photocrosslinking of coumarin moieties. However, in the presence of the reducing reagent (e.g., TECP) or UV exposure (256 nm), the crosslinked micelles with a high crosslinking degree (>62%) can be dissociated by SDS efficiently. This is indicated by the efficient reversibility of the crosslinking within micelles.

Figure 30:
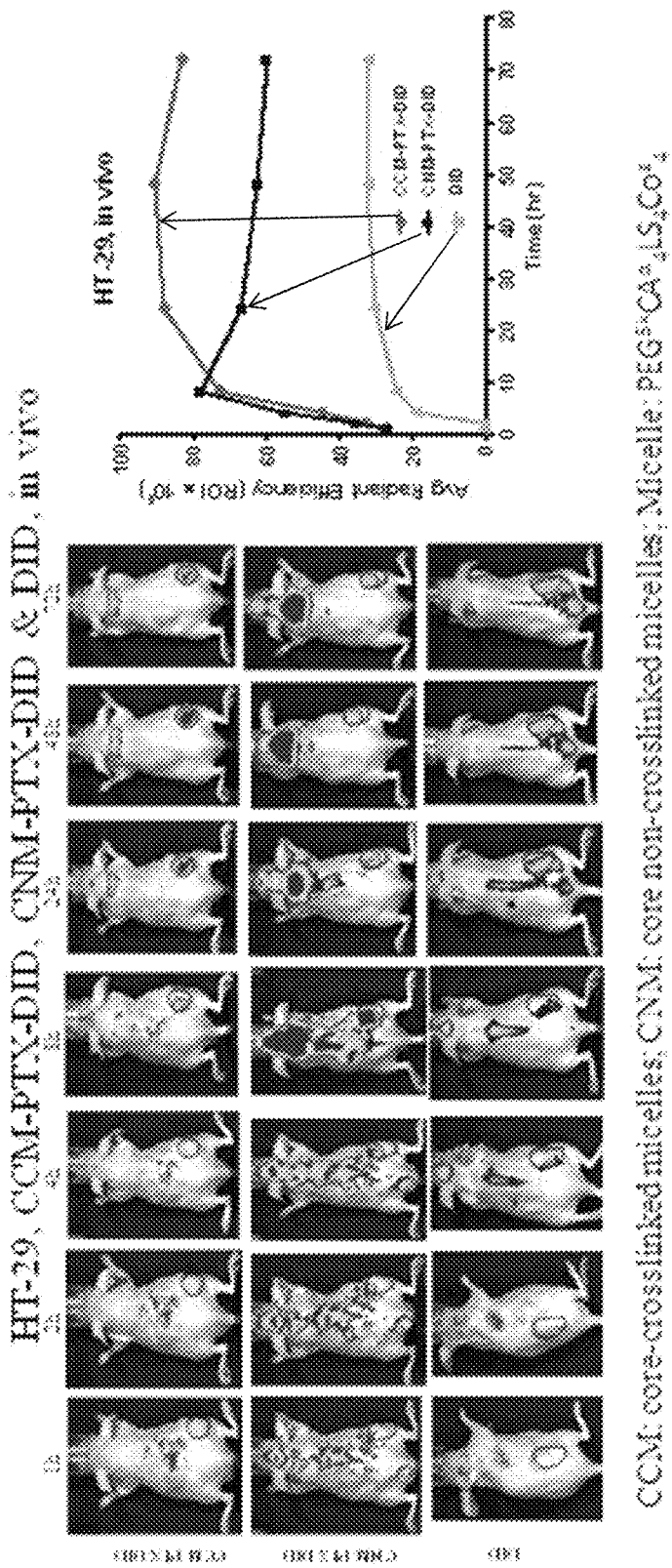
FIG. 30. An example of an in vivo and ex vivo fluorescence imaging of the animals bearing HT-29 colon cancer xenografts after intravenous (IV) injection of PTX and NIR dye DiD coloaded core crosslinked or noncrosslinked PEG$^{5k}$CA$^{\alpha}_4$LS$_4$Co$^{\varepsilon}_4$ micelles. The average fluorescence intensities of the in vivo tumor area and the ex-vivo biodistribution have been analyzed to compare the effects of the crosslinking on the tumor targeting.
Figure 30:
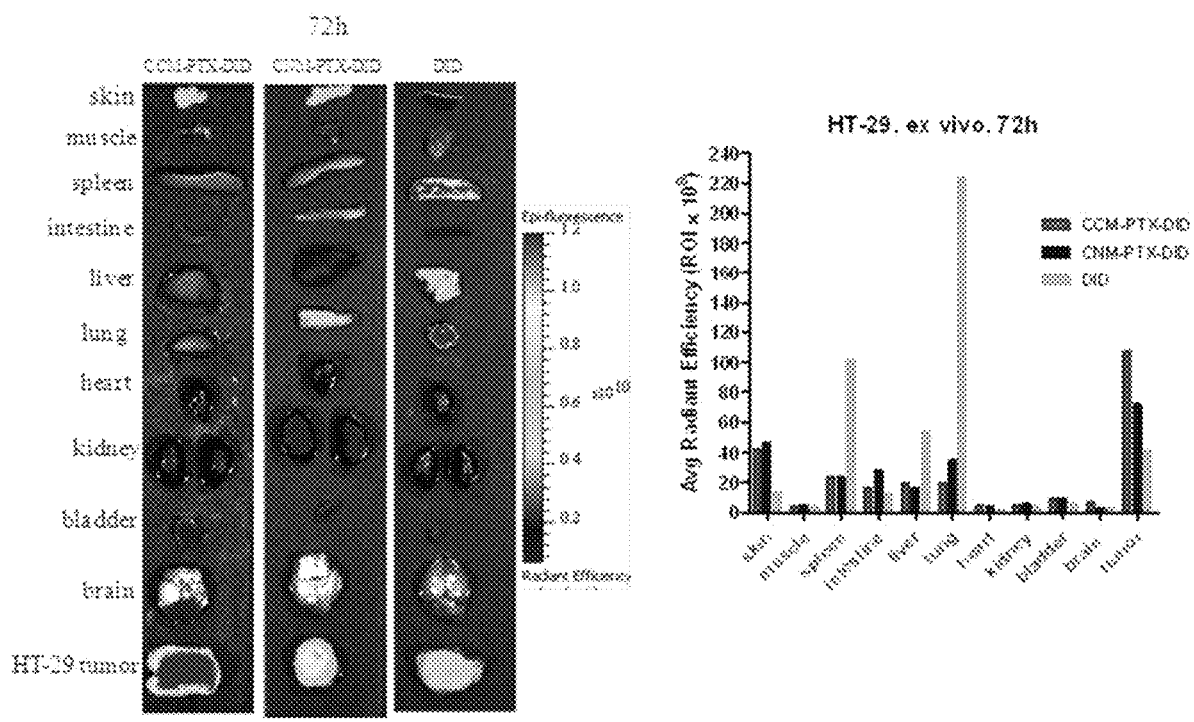

Paclitaxel and NIR dye DiD have been co-loaded into micelles formed by $PEG^{5k}CA^{\alpha}_{4}LS_{4}Co^{\epsilon}_{4}$ efficiently at a ratio of 10:1:0.25 (telodendrimer/PTX/DiD mass ratio). These nanoparticles were crosslinked via UV exposure and were injected via the tail vein into nude mice bearing colon cancer xenografts for the in vivo biodistribution study. As shown in FIG. 30, the core-crosslinked micelles (CCMs) can deliver payloads to tumor site much more efficiently than the non-crosslinked micelles (CNMs), due to the enhanced stability. The in vivo tumor concentration of the CCM formulations was continuous until 48 hours. In contrast, the tumoral fluorescence signal in the CNM-treated animals peaked at 8 hours and then declined, indicating the short half-life of the CNM formulation in the blood stream, which limited the EPR effects of the nanoparticles in solid tumor targeting. In the ex vivo biodistribution analysis after the last time point for in vivo imaging, animals were sacrificed and the organs and tumor were imaged, and compared with the free DiD treatment. The images clearly showed that the CCM can deliver a higher concentration of drug molecules into tumor sites, compared with free DiD and the CNM loaded DiD. Both nanoformulations can prevent the uptake of payloads to vital organs, such as the liver, lung and spleen. The above biodistribution results indicate possible reduced toxicity and enhanced anticancer effects for the photocrosslinked nanoformulations.

Surface Crosslinked Telodendrimers Micelles.

Figure 31:
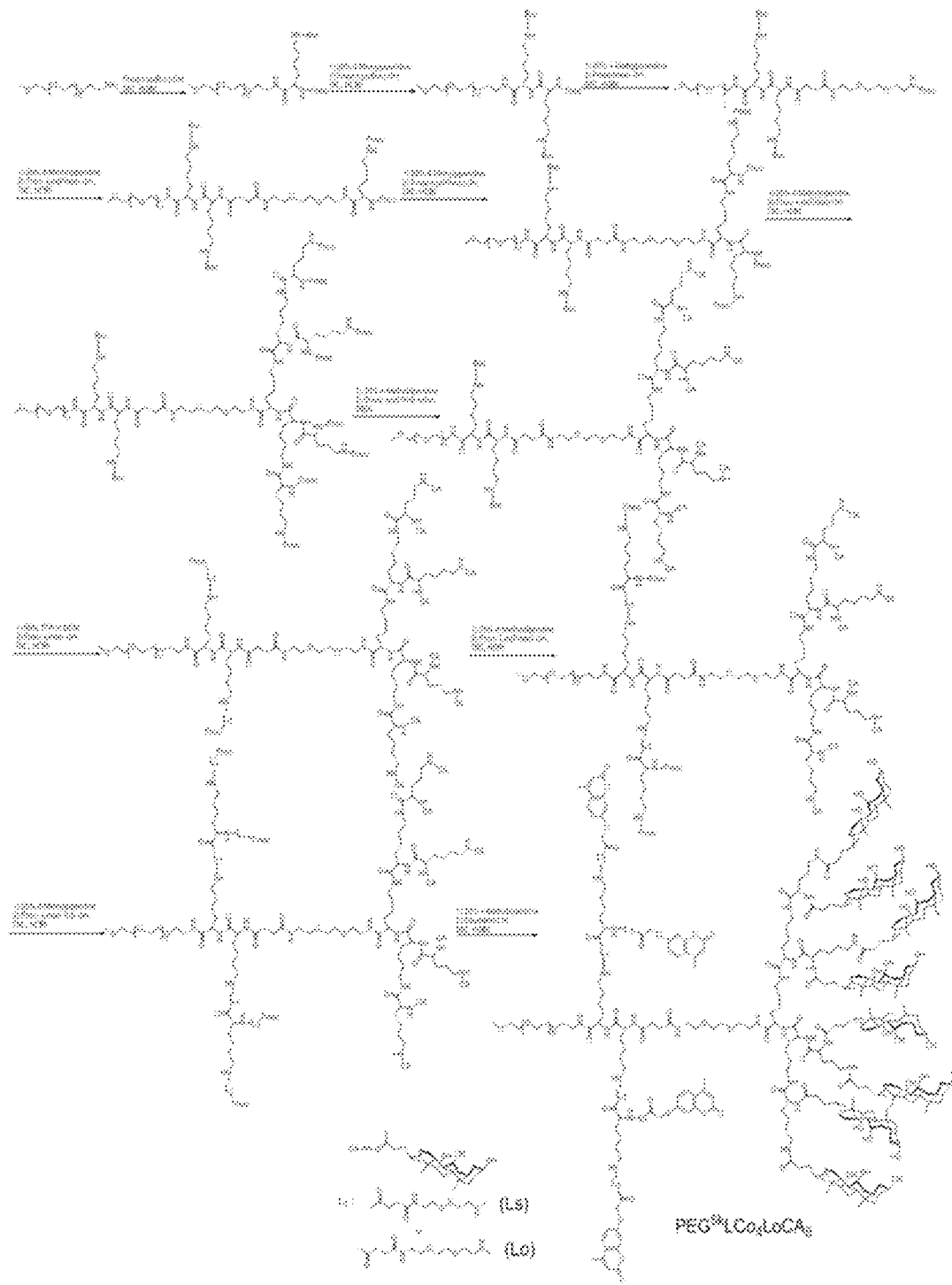
FIG. 31. An example of a synthetic route for the preparation of the trilayered telodendrimers PEG$^{5k}$LCo$_4$LoCA$_8$ with octamer of cholic acid in the core and four coumarin molecules in the intermediate layer via the spacer molecules for the reversible photo-crosslinking of micelles.
Figure 32:
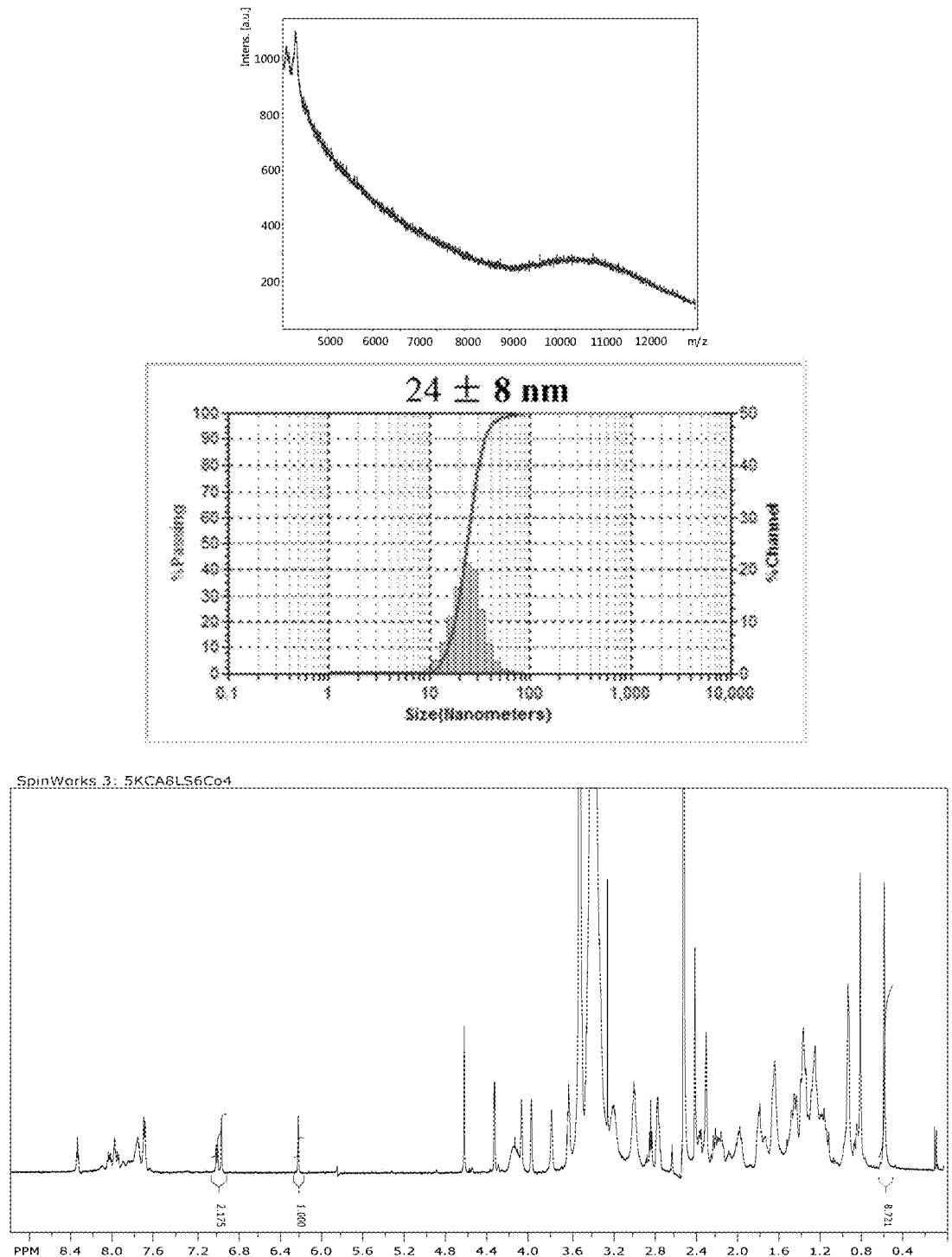
FIG. 32. Exemplary MALDI-TOF MS of PEG$^{5k}$CA$_8$LS$_6$Co$_4$ (exp. 10,600, the. 12,000); DLS particle size of the formed micelles were detected to be 24±8 nm (C$_{polymer}$=5 mgmL$^{-1}$), $^1$H NMR (DMSO-d$_6$) spectrum indicated the right composition of telodendrimer.
Figure 33:
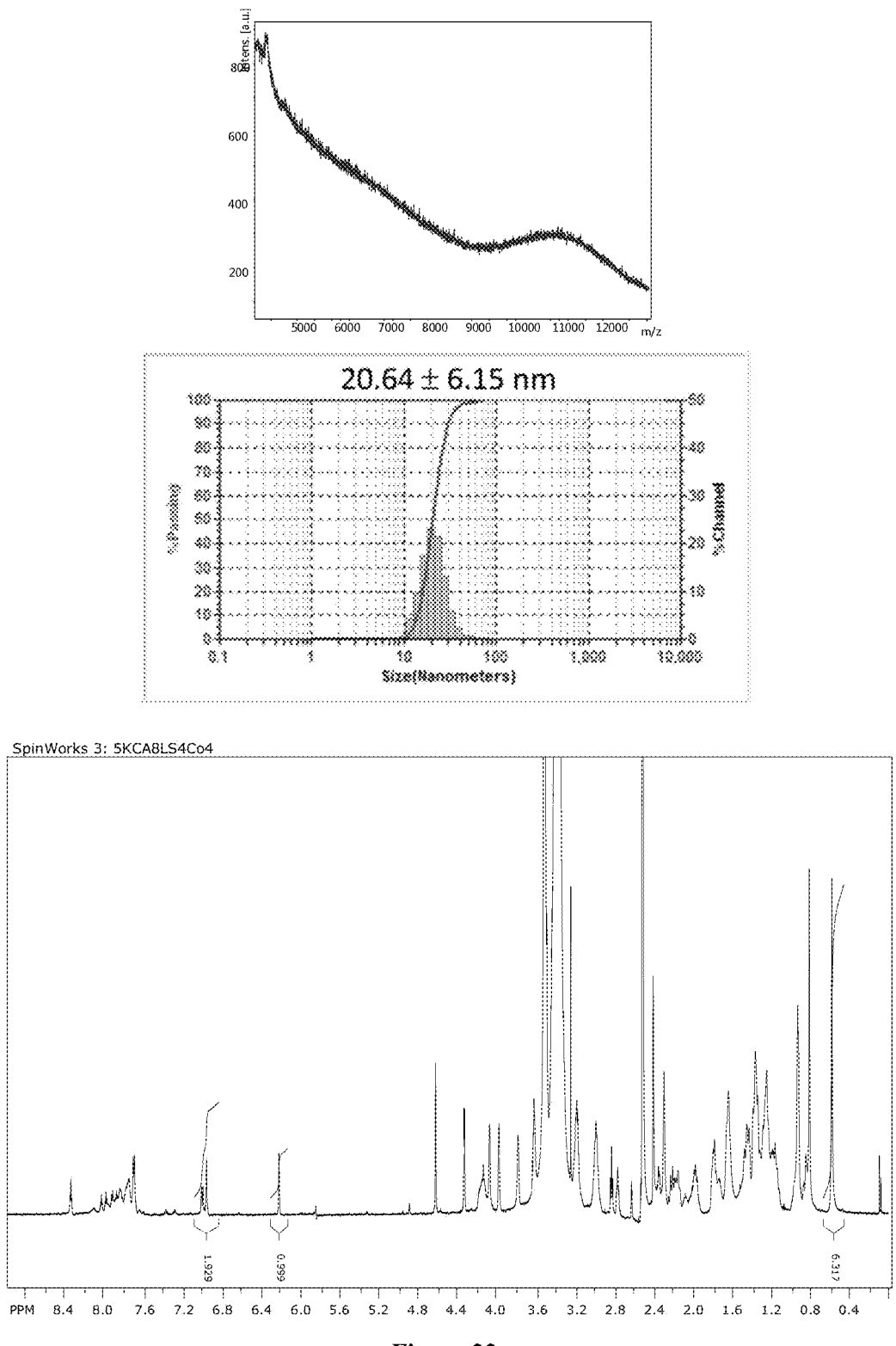
FIG. 33. Exemplary MALDI-TOF MS of PEG$^{5k}$CA$_8$LS$_4$Co$_4$ (exp. 11,000, The. 12000) DLS particle size of the formed micelles were detected to be 20.64±6.15 nm (polymer=5 mgmL$^{-1}$), $^1$H NMR spectrum of PEG$^{5k}$CA$_8$LS$_4$Co$_4$ indicated the right composition of telodendrimer.
Figure 34:
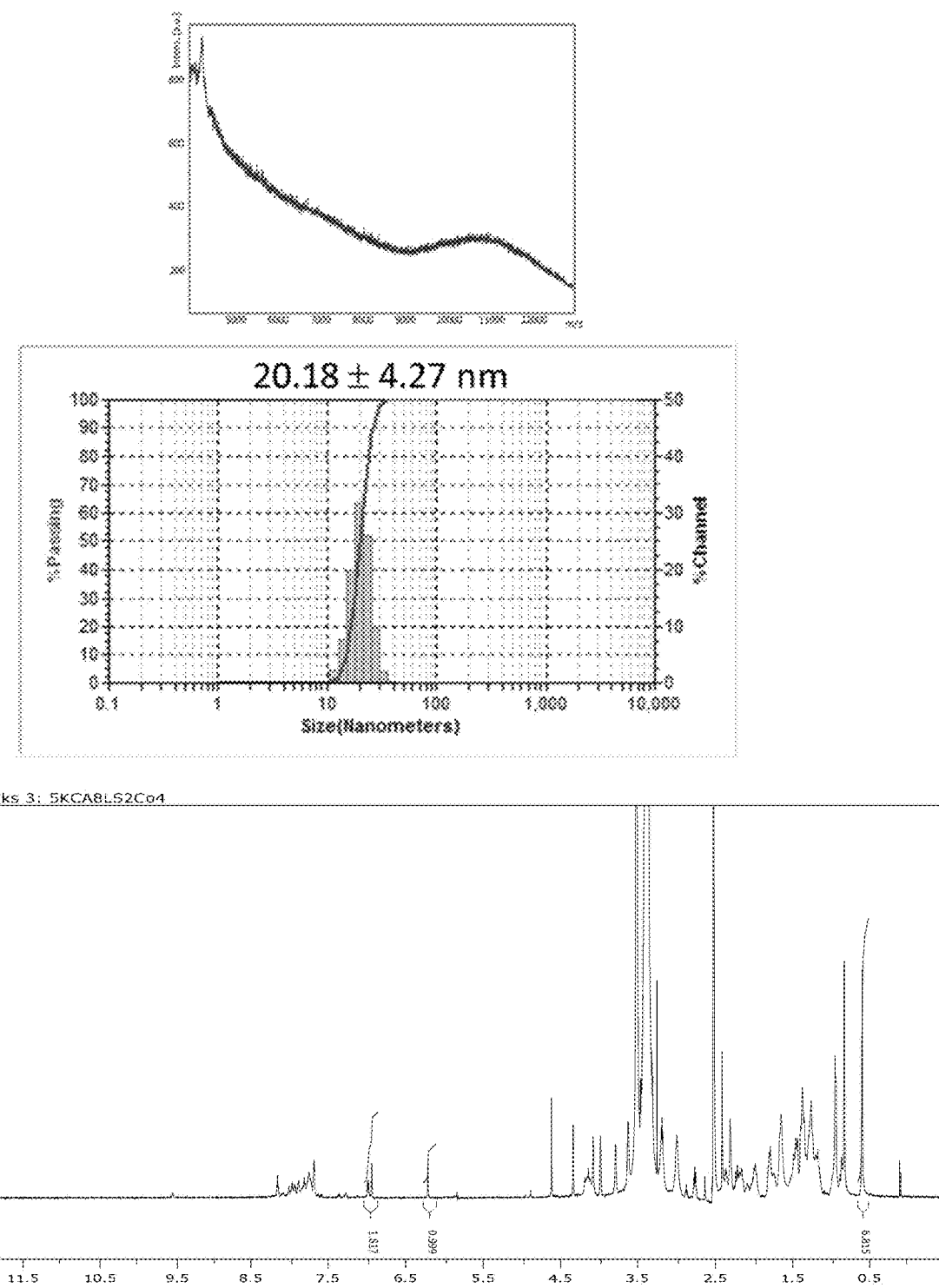
FIG. 34. Exemplary MALDI-TOF MS of PEG$^{5k}$CA$_8$LS$_2$Co$_4$ (exp. 11,000, The. 12000) DLS particle size of the formed micelles were detected to be 20.18±4.27 nm (polymer=5 mgmL$^{-1}$), $^1$H NMR spectrum of PEG$^{5k}$CA$_8$LS$_2$Co$_4$ indicated the right composition of telodendrimer.

As shown in FIG. 31, trilayered telodendrimers with coumarin in the intermediate layer were developed via peptide chemistry using Fmoc and Boc orthogonal protecting strategies. The ethylene glycol linker or disulfide bond containing linkers were inserted prior to the coumarin structure to adjust the flexibility and induce reducing sensitivity to decrosslinked micelles. As shown in FIG. 30, and FIGS. 31-34, the molecular weight of such telodendrimers with different spacer molecules was detected via MALDI-TOF MS to be very close to the theoretical value. The proton NMR spectra also indicated the proper ratio of cholic acid and coumarin building blocks in the molecule. The particle sizes of the empty assembled micelles were characterized via DLS particle sizer to be about 20 to 24 nm.

Figure 35:
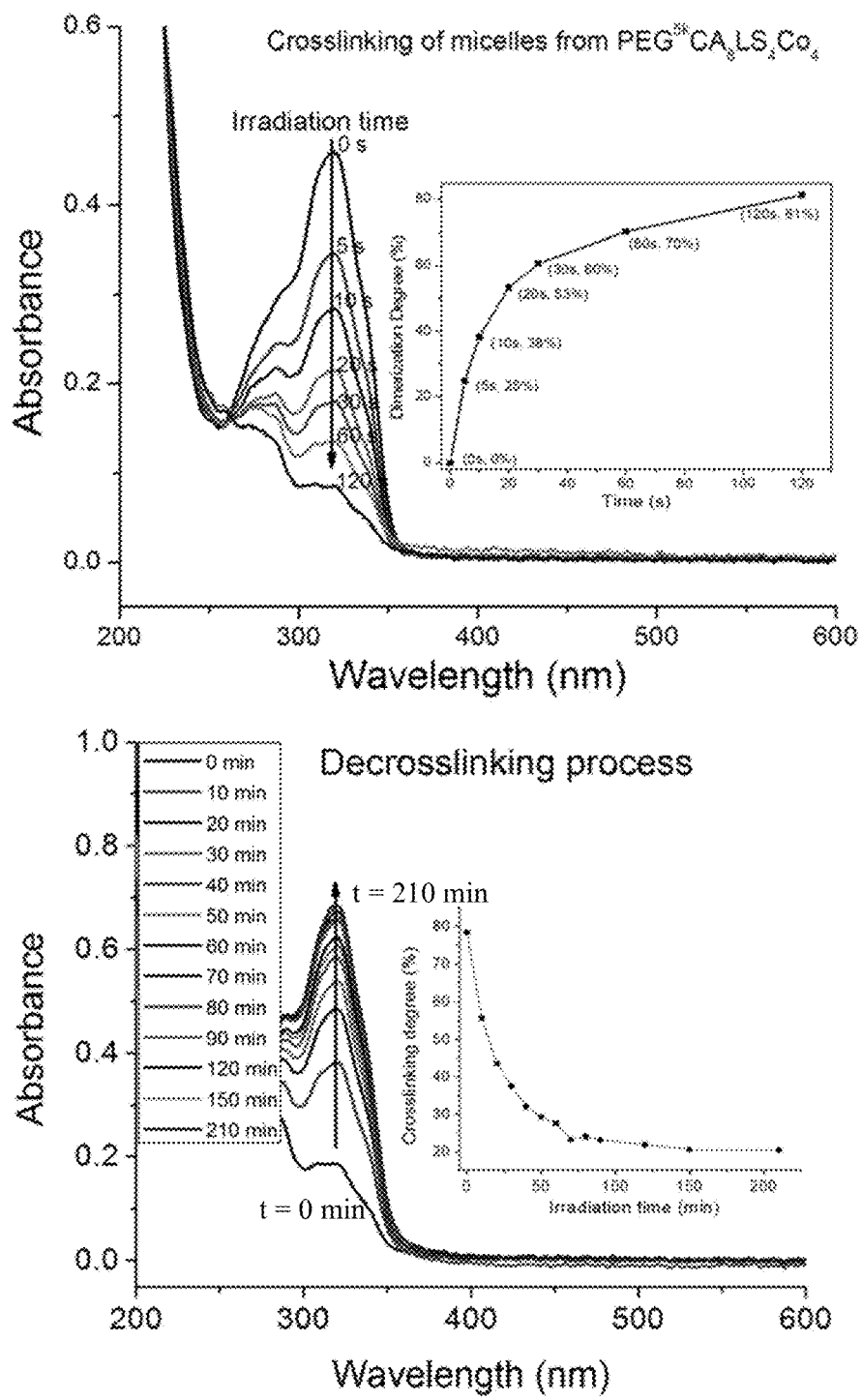
FIG. 35. An example of the kinetics of the photo-crosslinking and photo-decrosslinking of PEG$^{5k}$LS$_4$Co$_4$-LO-CA$_8$ micelles (5 mgmL$^{-1}$).
Figure 36:
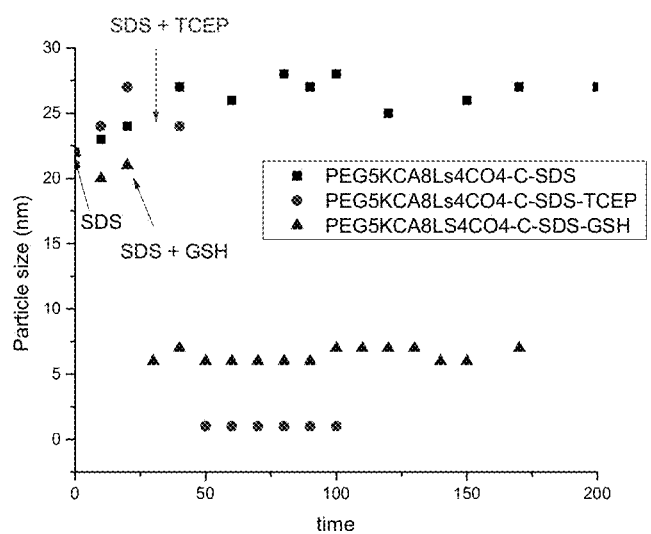
FIG. 36. An example of the stability of non/crosslinked micelles from PEG$^{5k}$CA$_8$LS$_4$Co$_4$ under various condition (SDS solution, mixture of SDS and TCEP, C$_{polymer}$=1 mgmL$^{-1}$, C$_{SDS}$=2.5 mgmL$^{-1}$, C$_{TCEP}$=20 mM).

The photocrosslinking of $PEG^{5k}CA_{8}LS_{4}Co_{4}$ micelles can be efficiently achieved via UV irradiation with $\lambda$>310 nm within a minute, as shown in FIG. 35. In addition, decrosslinking of micelles occurred upon exposure to the germicide UV lamp for 30 min with a 70% decrosslinking degree. The stability of the non-crosslinked micelle and photocrosslinked micelles was studied via a SDS challenging assay and monitored via a DLS particle sizer. Telodendrimer $PEG^{5k}CA_{8}LS_{4}Co_{4}$ was taken as an example shown in FIG. 36. The photocrosslinked micelles are stable in size upon the addition of SDS. However, addition of the reducing glutathione (GSH) or tricarboxilic ethyl phosphate (TCEP) was able to decrosslink the micelle via cleavage of the disulfide bonds. Therefore, micelle aggregates can be broken down by SDS efficiently. Interestingly, TCEP and glutathione break down micelles with the aid of SDS into different particle sizes. The smaller sizes in the TCEP treatment may due to the stronger reducing capability of TCEP and the complete cleavage of disulfide bonds.

Figure 37:
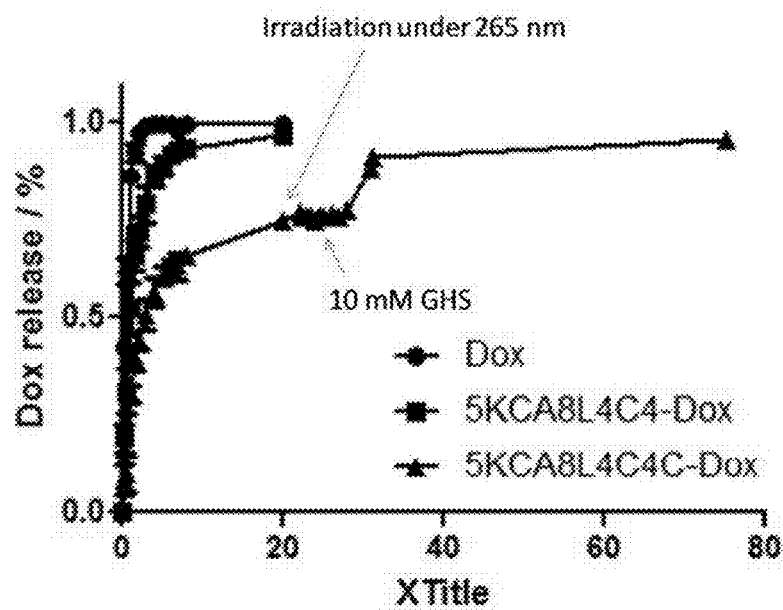
FIG. 37. An example of a DOX release profiles from the free DOX-HCl and DOX loaded in the crosslinked and noncrosslinked PEG$^{5k}$LoLS4Co4LoCA8 micelles. The photocrosslinked formulation was treated with UV 256 irradiation at a time point of 20 h followed by the addition of 10 mM GSH to trigger micelle decrosslinking and to further accelerate the drug release.

Doxorubicin can be loaded into these surface crosslinkable micelles at a 10:1 polymer/drug weight ratio. The crosslinking of the micelle slows down the release rate of the drug molecule as shown in FIG. 37. Compared with free DOX and DOX loaded in the noncrosslinked $PEG^{5k}LO_{2}LS_{4}Co_{4}LOCA_{8}$ micelles, the photocrosslinked formulation exhibited sustained a release profile, which was accelerated by irradiation at UV 256 nm at the time point of 20 h followed by the addition of 10 mM GSH to trigger micelle decrosslinking. These results indicate the potential application of these photocrosslinkable nanoformulations for on-demand drug release at a tumor site in response to the reducing intratumoral microenviroments.

Paclitaxel and NIR dye DiD were co-loaded into the micelles formed by $PEG^{5k}LO_{2}LS_{4}Co_{4}LOCA_{8}$ efficiently at a ratio of 10:1:0.25 (telodendrimer/PTX/DiD mass ratio).

Figure 38:
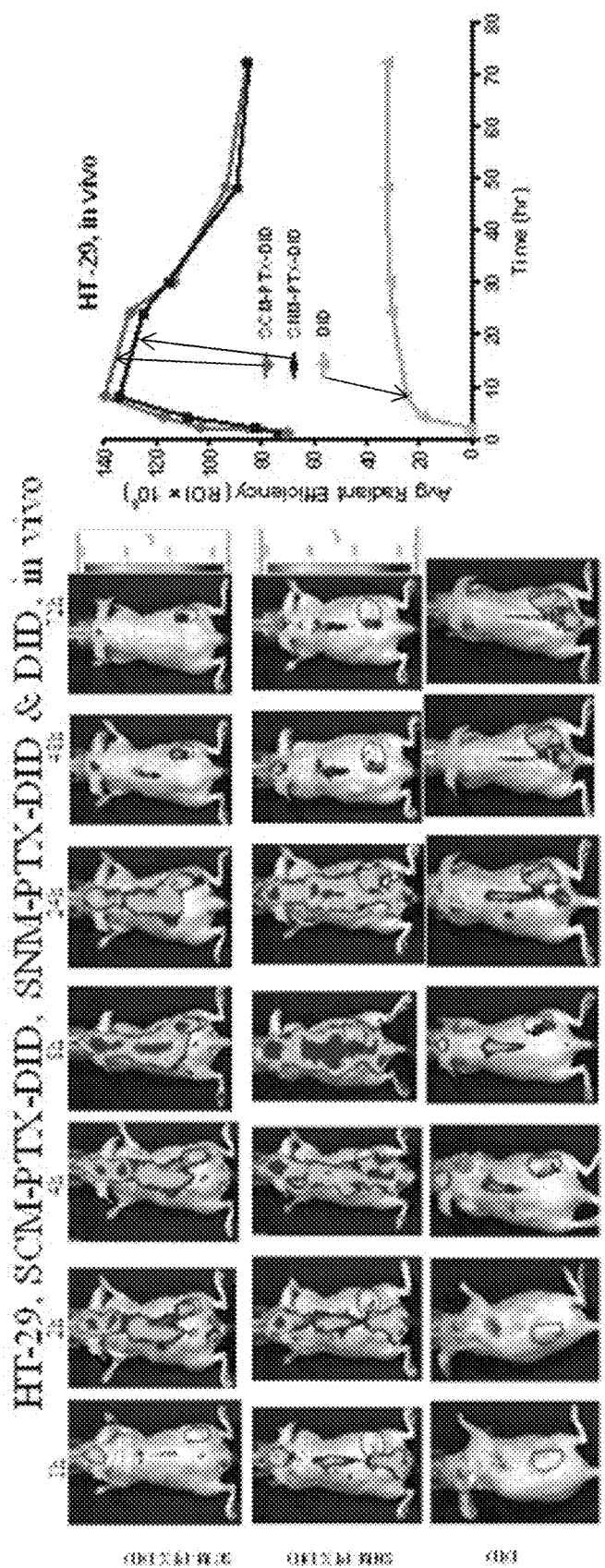
FIG. 38. An example of an in vivo and ex vivo fluorescence imaging of the animals bearing HT-29 colon cancer xenografts after intravenous (IV) injection of PTX and NIR dye DiD coloaded surface crosslinked or noncrosslinked PEG$^{5k}$CA$_8$LS$_4$Co$_4$ micelles. The average fluorescence intensities from the in vivo tumor area and the ex vivo biodistribution have been analyzed to compare the effects of the crosslinking on the tumor targeting.
Figure 38:
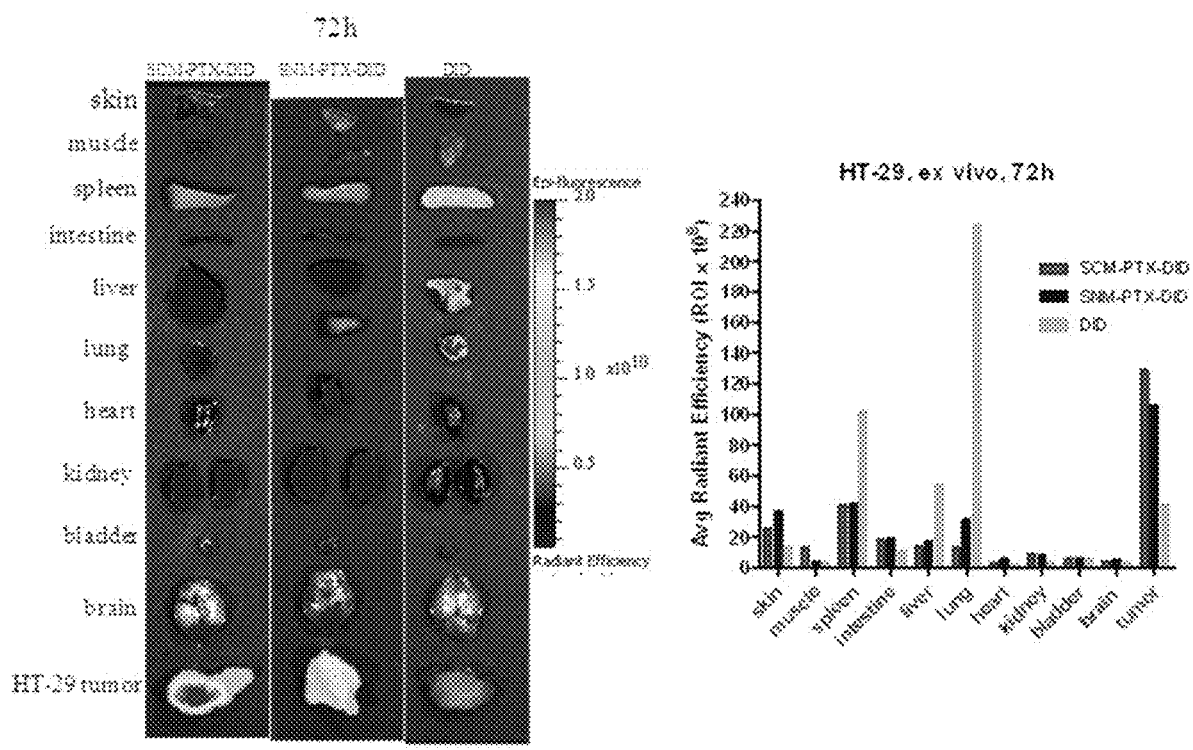
Figure 39:
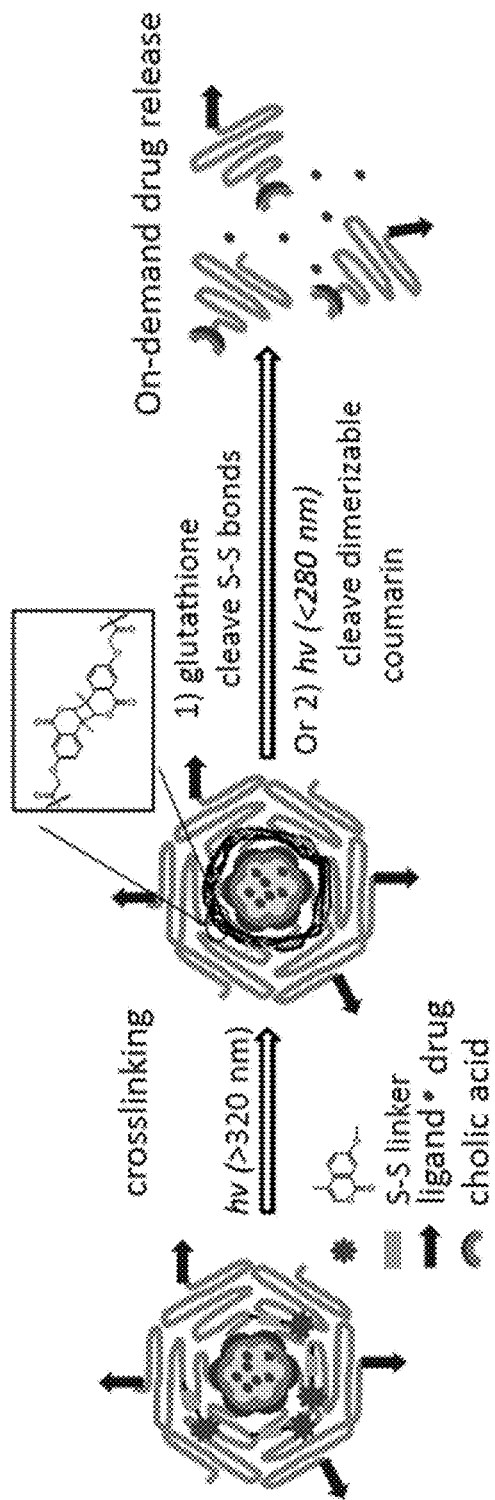
FIG. 39. An example of a schematic illustration of the coumarin containing reversible photocrosslinkable micelles and the decrosslinking of micelles via reducing glutathione to cleave disulfide bond or photo-irradiation with UV light at wavelength shorter than 280 nm.
Figure 40:
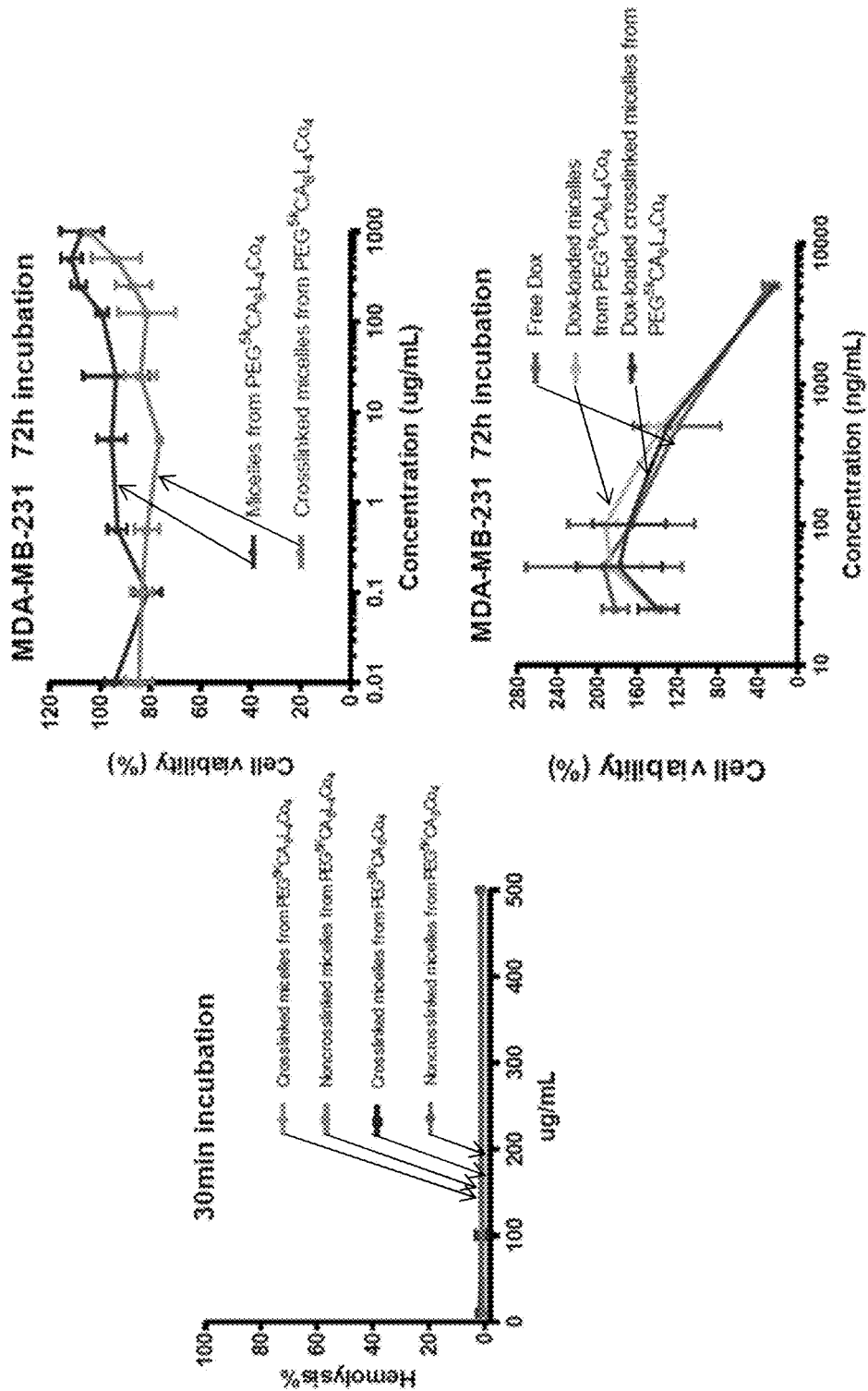
FIG. 40. No hemolytic properties were observed for the noncrosslinked and crosslinked micelles with coumarin as building blocks (left). The crosslinked and noncrosslinked micelles formed by PEG$^{5k}$CA$_8$L$_4$Co$_4$ were shown to be nontoxic via incubation with MDA-MB-231 up to 1 mg/mL (top right). DOX loaded crosslinked and noncrosslinked micelles formed by PEG$^{5k}$CA$_8$L$_4$Co$_4$ exhibit similar cytotoxicity with free DOX against breast cancer MDA-MB-231 cell line.

These nanoparticles were crosslinked via UV exposure with a slight size reduction from 26.5 to 24.7 nm. These formulations were injected via tail vein into nude mice bearing colon cancer xenografts for in vivo biodistribution study. As shown in FIG. 38, the colon cancer (HT-29) bearing nude mice treated with the PTX-DiD co-loaded nanoformulations have a strong fluorescence signal at tumor site compared with the free DiD treated animals. The surface-crosslinked micelle (SCM) exhibited a tumor targeting profile similar to the noncrosslinked micelles via in vivo fluorescent imaging. The in vivo signal at the tumor sites was peaked at eight hours post-injection through the tail vein. However, the ex vivo biodistribution imaging showed a stronger fluorescent intensity at the tumor site in the animal treated with SCM nanoformulation, compared with that in SNM treatment. Consistently observed was a high uptake of fluorescent signal in spleen and lung for the animal treated with free dye.

As demonstrated above, the novel trilayered telodendrimers provide flexibility in engineering the structure of telodendrimer via incorporating various drug-affinitive building blocks in the core of the micelles. The use of amphiphilic loading capacity and stability is able to lead to better tumor targeting and anticancer effects in vivo.

Example 2

This example shows examples of telodendrimers and supporting data of same.

The telodendrimers used have three segregated functional segments: (1) a PEG layer that forms hydrophilic shell to resist nonspecific interactions with biological components; (2) a stabilizing (intermediate) layer that isolates drug holding layer and further stabilizes nanoparticle; and (3) an affinity layer that is optimized to hold specific drug being delivered.

Some examples of some of the advantages of the telodendrimers of the present disclosure include: (1) independent control and optimization of properties of each of the three functional layers; (2) excellent reproducibility and stability; (3) significantly increased drug-loading capacity; and (4) highly controlled degradation.

TABLE 5

Loading results of nanocarriers formed from the telodendrimers with drugs.

| | Polymer | | | | | |
|---|---|---|---|---|---|---|
| Drug | $PEG^{5k}CA_4$-$VE_4$ (multiple size) | $PEG^{5k}VE_4$-$CA_4$ (multiple size) | $PEG^{5k}CA_4$-L-$VE_4$ (24 nm) | $PEG^{5k}CA_4$-$L_2$-$VE_4$ (19.96 nm) | $PEG^{5k}CA_4$-$L_4$-$VE_4$ (16.9 nm) | $PEG^{5k}VE_8$ (multiple) |
| Gambogic acid | X | X | 5:1.5 mg | X | 5:1.5 mg | X |
| Oridonin | — | — | 5:0.5 mg | 5:0.5 mg | 5:0.5 mg | — |
| Norcantharidin | — | — | 5:1.5 mg | 5:1.5 mg | 5:1.5 mg | — |
| PTX | X | X | 10:1 mg | X | 10:1 mg | X |
| VP 16 | — | — | 5:0.5 mg (precipitation after 3 days) | 5:0.5 mg (precipitation after 1 days) | 5:0.5 mg (precipitation after 1 days) | — |
| Docetaxel | | | Good | | | |
| Doxorabicine | | | Good | | | |

—: Not done;
X: Cannot load into polymer cholic acid in the intermediate layer of the telodendrimer is able to stabilize the payload drug molecules and prevent the further aggregation of nanoparticles. As examples, Vitamin E, Rhein and courmarin were introduced into the trilayered telodendrimers as drug binding blocks to increase the drug loading capacity and stabilities for several anticancer drugs, namely, Gambogic acid, VP-16, paclitaxel, doxorubicine, orindornine, norcantrheridine, triptolide, SN-38, etc. The trilayered telodendrimers containing coumarin building blocks can be crosslinked reversible upon the UV irradiation, which can stabilize the payload nanoparticle in vitro and in vivo for on-demand drug release. At the same time, the trilayered telodendrimers containing coumarin as building blocks can increase the loading capacity and stability of SN-38, compared with two-layered telodendrimers having the same chemical components. The similar phenomena was observed for Vitamin E containing nanocarriers: the trilayered telodendrimer can encapsulate gambogic acid, orindonine and norcantheridin more efficiently than can two-layered ones with the same chemical components. Trilayered telodendrimers with riboflavin in the inner layer form a nanocarrier which can efficiently encapsulate doxorubicin and daunorubicin as rhein containing telodendrimers. As demonstrated in the study of doxorubicin delivery via the rhein-containing teleodendrimer, the improved drug While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A compound of formula (I):

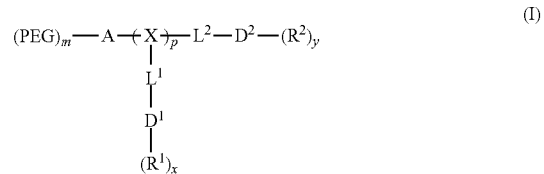

wherein
PEG is a polyethylene glycol moiety, wherein PEG has a molecular weight of 44 Da to 100 kDa;
A is optional and is a monomer or oligomer;
X is a branched monomer unit;
each $L^1$ is independently optional and is a linker group;
each $L^2$ is independently optional and a linker group, wherein at least one of $L^1$ and/or at least one of $L^2$ are present;

D$^1$ is a dendritic polymer moiety having one or more branched monomer units (X), a plurality of end groups, and optionally, one or more linker groups $L^1$;

D$^2$ is a dendritic polymer having one or more branched monomer units (X), a plurality of end groups, and optionally, one or more linker groups ($L^3$);

each $L^3$ is independently optional or a linker group linked to the focal point group of the dendritic polymer and monomer unit (X);

R$^1$ is an end group of the dendritic polymer and is independently at each occurrence in the compound selected from the group consisting of a cholic acid moiety or derivative or analog thereof, a coumarin moiety or derivative or analog thereof, a riboflavin moiety or derivative or analog thereof, and a chlorogenic acid moiety or derivative or analog thereof and R$^2$ is an end group of the dendritic polymer and is independently at each occurrence in the compound selected from the group consisting of a rhein moiety or derivative or analog thereof, a bile acid moiety or derivative or analog thereof, a cholesterol moiety or derivative or analog thereof, a coumarin moiety or derivative or analog thereof, a curcumine moiety or derivative or analog thereof, a flavin moiety or derivative or analog thereof, a isoflavin moiety or derivative or analog thereof, a riboflavin moiety or derivative or analog thereof, a retinol moiety or derivative or analog thereof, a retinoic acid moiety or derivative or analog thereof, a chlorogenic acid moiety or derivative or analog thereof, an anthraquinone moiety or derivative or analog thereof, a xanthenone moiety or derivative or analog thereof, a Vitamin E moiety or derivative or analog thereof, a D-α-tocopherol succinate moiety or derivative or analog thereof, a quercetin moiety or derivative or analog thereof, a chenodeoxylcholic acid moiety or derivative or analog thereof, terpenoids, steroids, vitamins, lipids, and fatty acids, wherein R$^1$ and R$^2$ are not the same, and when R$^1$ and/or R$^2$ are not end groups each R$^1$ and/or R$^2$ is linked to one of the end groups;

subscript x is an integer from 2 to 64, wherein subscript x is equal to the number of end groups on the dendritic polymer;

subscript y is an integer from 2 to 64, wherein subscript y is equal to the number of end groups on the dendritic polymer;

subscript p is an integer from 1 to 32; and subscript m is an integer from 1 to 32.

2. The compound of claim 1, wherein at each occurrence in the compound the branched monomer unit (X) is independently selected from the group consisting of a diamino carboxylic acid moiety, a dihydroxy carboxylic acid moiety, and a hydroxyl amino carboxylic acid moiety.

3. The compound of claim 2, wherein at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid.

4. The compound of claim 2, wherein the diamino carboxylic acid moiety is an amino acid moiety.

5. The compound of claim 2, wherein each branched monomer unit X is lysine moiety.

6. The compound of claim 1, wherein the compound is selected from the group consisting of:

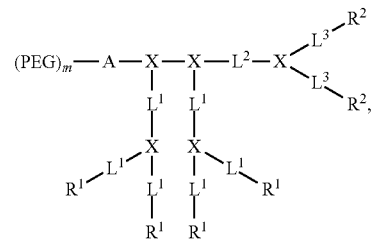

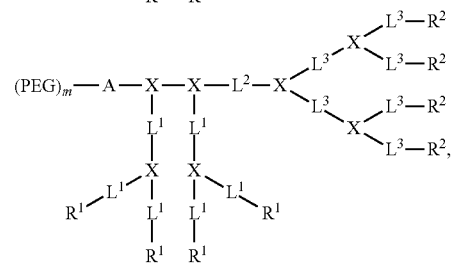

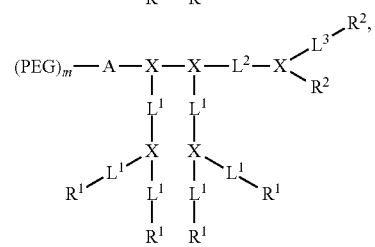

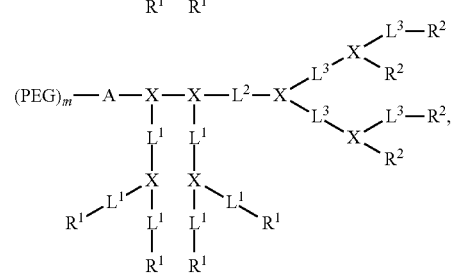

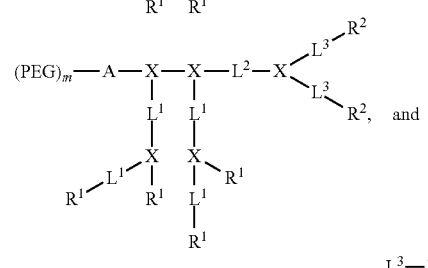

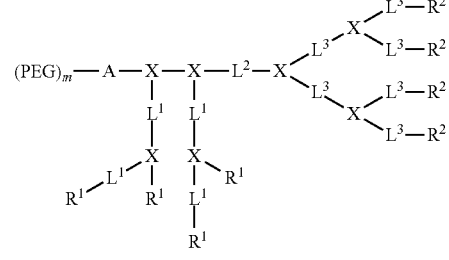

wherein each branched monomer unit is lysine moiety.

7. The compound of claim 1, wherein at each occurrence in the compound the linker $L^1$, $L^2$, and $L^3$ each are independently selected from the group consisting of a polyethylene glycol moiety, polyserine moiety, enzyme cleavable peptide moiety, disulfide bond moiety and acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety.

8. The compound of claim 1, wherein at each occurrence in the compound the linker $L^1$, $L^2$, and $L^3$ are independently selected from the group consisting of:

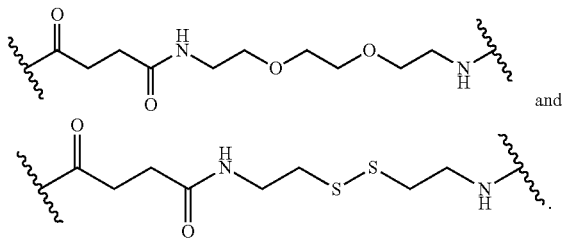

and

9. The compound of claim 1, wherein the linker $L^1$, $L^2$, $L^3$, or a combination thereof comprises a cleavable group.

10. The compound of claim 9, wherein the cleavable group is a disulfide cleavable moiety.

11. The compound of claim 1, wherein the $(PEG)_m$-A-portion of the compound is selected from the group consisting of:

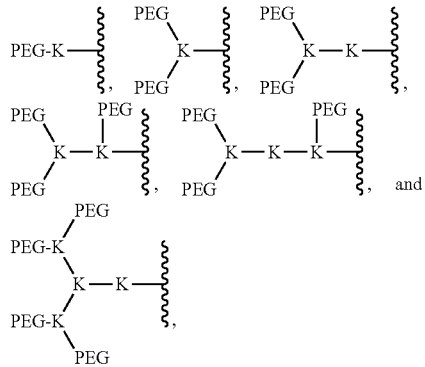

wherein each K is lysine.

12. The compound of claim 1, wherein a portion of or each $R^1$ is a reversible photocrosslinking group.

13. The compound of claim 12, wherein the reversible photocrosslinking group is coumarin moiety, 4-methylcoumarin moiety, chlorogenic acid moiety or derivative or analog thereof, or a combination thereof.

14. The compound of claim 6, wherein x=4; y=4, m=1, PEG is 5 kDa; $R^1$ is a coumarin moiety; each $R^2$ is independently selected from the group consisting of cholic acid moiety or derivative or analog thereof, cholesterol moiety or derivative or analog thereof, rhein moiety or derivative or analog thereof, Vitamin E moiety or derivative or analog thereof, coumarin moiety or derivative or analog thereof, curcumine moiety or derivative or analog thereof, and riboflavin moiety or derivative or analog thereof; $L^1$ is optional or a disulfide bond moiety; $L^2$ is an ethylene glycol linker; and $L^3$ is optional or an ethylene glycol linker.

15. The compound of claim 1, wherein x=2 to 16; y=2 to 64, m=1 to 8, PEG is 1 to 40 kDa; each $R^1$ is independently selected from a coumarin moiety or derivative or analog thereof, a cinnamic acid moiety or derivative or analog thereof, and a chlorogenic acid moiety or derivative or analog thereof; each $R^2$ is independently selected from the group consisting of cholic acid moiety or derivative or analog thereof, cholesterol moiety or derivative or analog thereof, rhein moiety or derivative or analog thereof, Vitamin E moiety or derivative or analog thereof, coumarin moiety or derivative or analog thereof, curcumine moiety or derivative or analog thereof, and riboflavin moiety or derivative or analog thereof; $L^1$ is optional or a disulfide bond moiety; $L^2$ is an ethylene glycol linker; and $L^3$ is optional or an ethylene glycol linker.

16. The compound of claim 6, wherein x=4; y=4, m=1, PEG is 5 kDa; $R^1$ is a cholic acid moiety or derivative or analog thereof; each $R^2$ is independently selected from the group consisting of cholesterol moiety or derivative or analog thereof, rhein moiety or derivative or analog thereof, Vitamin E moiety or derivative or analog thereof, coumarin moiety or derivative or analog thereof, curcumine moiety or derivative or analog thereof, riboflavin moiety or derivative or analog thereof, retinoic acid moiety or derivative or analog thereof, and a chlorogenic acid moiety or derivative or analog thereof; $L^1$ is optional or a disulfide bond moiety; $L^2$ is an ethylene glycol linker; and $L^3$ is optional or an ethylene glycol linker.

17. The compound of claim 1, wherein x=2 to 16; y=2 to 64, m=1 to 8, PEG is 1 to 40 kDa; each $R^1$ is independently selected from the group consisting of a cholic acid moiety or derivative or analog thereof moiety, riboflavin moiety or derivative or analog thereof, and a chlorogenic acid moiety or derivative or analog thereof; each $R^2$ is independently selected from the group consisting of cholic acid moiety or derivative or analog thereof, cholesterol moiety or derivative or analog thereof, rhein moiety or derivative or analog thereof, Vitamin E moiety or derivative or analog thereof, coumarin moiety or derivative or analog thereof, curcumine moiety or derivative or analog thereof, riboflavin moiety or derivative or analog thereof, and retinoic acid moiety or derivative or analog thereof; $L^1$ is optional or a disulfide bond moiety; $L^2$ is an ethylene glycol linker; and $L^3$ is optional or an ethylene glycol linker.

18. A nanocarrier comprising a plurality of compounds of claim 1.

19. The nanocarrier of claim 18, wherein the nanocarrier further comprises a hydrophobic drug or an imaging agent.

20. The compound of claim 1, wherein x=4 and y=2 or 4.

21. The compound of claim 1, wherein p=1 and x=4.

22. The compound of claim 1, wherein p=2 and x=4.

23. The compound of claim 1, wherein $R^2$ is a rhein moiety or group or derivative or analog thereof, bile acid moiety or group or derivative or analog thereof, flavin moiety or group or derivative or analog thereof, isoflavin moiety or group or derivative or analog thereof, riboflavin moiety or group or derivative or analog thereof, retinol moiety or group or derivative or analog thereof, retinoic acid moiety or group or derivative or analog thereof, Vitamin E moiety or group or derivative or analog thereof, cholesterol moiety or derivative or analog thereof, coumarin moiety or derivative or analog thereof, curcumine moiety or derivative or analog thereof, heptadecanoic acid and other fatty acid derivative or analog thereof.

24. The compound of claim 1, wherein $R^1$ is a cholic acid moiety or derivative or analog thereof.

25. The compound of claim 1, wherein $R^1$ is 4-methylcoumarin moiety or derivative or analog thereof.

26. The compound of claim 1, wherein the compound forms an intermediate layer comprising $R^1$ end groups.

* * * * *